US011807905B2

(12) United States Patent
Hess et al.

(10) Patent No.: US 11,807,905 B2
(45) Date of Patent: *Nov. 7, 2023

(54) GROWTH DIFFERENTIATION FACTOR 15 AS BIOMARKER FOR METFORMIN

(71) Applicants: Sanofi-Aventis Deutschland GmbH, Frankfurt am Main (DE); McMaster University, Hamilton (CA)

(72) Inventors: Sibylle Hess, Frankfurt am Main (DE); Thorsten Sadowski, Frankfurt am Main (DE); Hertzel Gerstein, Toronto (CA); Guillaume Pare, Puslinch (CA); Gregory Steinberg, Ancaster (CA)

(73) Assignees: Sanofi-Aventis Deutschland GmbH, Frankfurt am Main (DE); McMaster University

(*) Notice: Subject to any disclaimer, the term of this patent is extended or adjusted under 35 U.S.C. 154(b) by 149 days.

This patent is subject to a terminal disclaimer.

(21) Appl. No.: 17/198,781

(22) Filed: Mar. 11, 2021

(65) Prior Publication Data
US 2021/0254156 A1 Aug. 19, 2021

Related U.S. Application Data

(62) Division of application No. 16/064,341, filed as application No. PCT/EP2016/082163 on Dec. 21, 2016, now Pat. No. 10,975,434.

(30) Foreign Application Priority Data
Dec. 23, 2015 (EP) .................................... 15202424

(51) Int. Cl.
*A61K 31/155* (2006.01)
*C12Q 1/6876* (2018.01)

(52) U.S. Cl.
CPC .......... *C12Q 1/6876* (2013.01); *A61K 31/155* (2013.01); *C12Q 2600/106* (2013.01); *C12Q 2600/158* (2013.01)

(58) Field of Classification Search
CPC ....... A61K 31/155; A61P 3/10; C12Q 1/6876; C12Q 2600/106; C12Q 2600/158
See application file for complete search history.

(56) References Cited

U.S. PATENT DOCUMENTS

2017/0327560 A1* 11/2017 Armstrong ............. C12N 15/11

FOREIGN PATENT DOCUMENTS

| EP | 2383571 A1 | 11/2011 |
| EP | 2439535 A1 | 4/2012 |
| JP | 2002529417 A | 9/2002 |
| WO | 2000027401 A1 | 5/2000 |
| WO | 2013012648 A1 | 1/2013 |

OTHER PUBLICATIONS

Wang et al., "GDF15: Emerging biology and therapeutic applications for obesity and cardiometabolic disease", Nature Reviews—Endocrinology, 2021, vol. 17, pp. 592-607.
Adela and Banerjee, "GDF-15 as a target and biomarker for diabetes and cardiovascular diseases: A translational prospective". Journal of Diabetes Research, vol. 12, No. 6, Jan. 1, 2015 (Jan. 1, 2015), pp. 461-14.
Altschul et al., "Basic local alignment search tool", J. Mol. Biol., 1990, 215, 403-410.
Altschul et al., "Gapped BLAST and PSI-BLAST: a new generation of protein database search programs", Nucleic Acids Research, 1997, vol. 25, No. 17, 3389-3402.
Bannister et al., "Can people with type 2 diabetes live longer than those without? A comparison of mortality in people initiated with metformin or sulphonylurea monotherapy and matched, non-diabetic controls", Diabetes, Obesity and Metabolism, 2014, 16: 1165-1173.
Bosch et al., "n-3 Fatty Acids and cardiovascular outcomes in patients with dysglycemia", N Engl J Med, 2012, 367:309-18.
Breit et al.,"The TGF-β superfamily cytokine, MIC-1/GDF15: A pleotrophic cytokine with roles in inflammation, cancer and metabolism", Growth Factors, 2011, 29(5):187-195.
Brudno et al., "Glocal alignment: finding rearrangements during alignment", Bioinformatics, 2003, vol. 19, Suppl 1, i54-i62.
Castillo-Quan et al., "Genetics and pharmacology of longevity: The road to therapeutics for healthy aging", Adv Genetics, 2015, 90, 1-73.
Cool et al., "Identification and characterization of a small molecule AMPK activator that treats key components of type 2 diabetes and the metabolic syndrome", Cell Metab, 2006, 3, 403-416.
De Jager et al., "Growth differentiation factor 15 deficiency protects against atherosclerosis by attenuating CCR2-mediated macrophage chemotaxis", JEM, 2011, vol. 208, No. 2, 217-225.
Ding et al., "Identification of macrophage inhibitory cytokine-1 in adipose tissue and its secretion as an adipokine by human adipocytes", Endocrinology, 2009, 150(4):1688-1696.
Extended European Search Report dated Jun. 10, 2016 issued in European patent appl. No. 15 202 424.6.
Fonseca et al., Curr. Med. Res. & Opin., 2003, Taylor & Francis, vol. 19(7), pp. 635-641.

(Continued)

*Primary Examiner* — Sarah Pihonak
(74) *Attorney, Agent, or Firm* — McNeill Baur PLLC

(57) ABSTRACT

The present invention relates to metformin for use in treating a patient, wherein the patient exhibits an increased level of GDF15 in response to metformin treatment; to methods of identifying a patient who will benefit or who will not benefit from metformin treatment; methods of treating a patient at risk of developing or suffering from a disease or disorder comprising administering therapeutically effective amount of metformin; methods of adapting the dosage of metformin; the usage of GDF15 as biomarker for identifying a patient who will benefit or who will not benefit from metformin treatment, kits for use in identifying a patient who will benefit from metformin treatment and the use of the kits, as well as methods of treating a patient or who will not benefit from metformin treatment.

12 Claims, 5 Drawing Sheets

Figure 1:
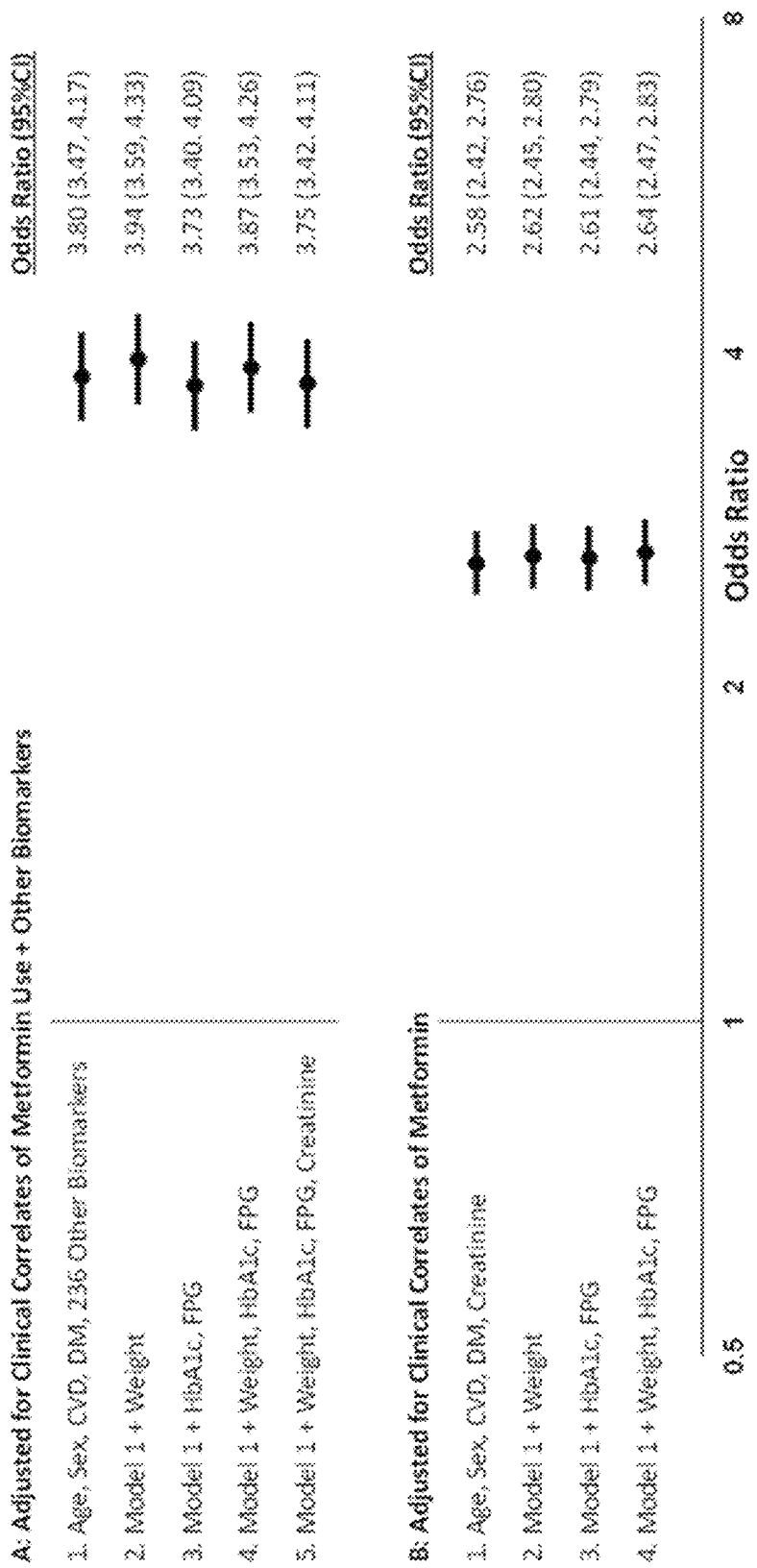

Specification includes a Sequence Listing.

(56) References Cited

OTHER PUBLICATIONS

Ford et al., "Metformin and salicylate synergistically activate liver AMPK, inhibit lipogenesis and improve insulin sensitivity", Biochem. J., 2015, 468, 125-132.
Fujita et al., "GDF15 is a novel biomarker to evaluate efficacy of pyruvate therapy for mitochondrial diseases", Mitochondrion, 2015, 20, 34-42.
Fullerton et al., "Immunometabolism of AMPK in insulin resistance and atherosclerosis", Molecular and Cellular Endocrinology 2013, 366, 224-234.
Fullerton et al., "Single phosphorylation sites in Acc1 and Acc2 regulate lipid homeostasis and the insulin-sensitizing effects of metformin", Nature Medicine, 2013, vol. 19, No. 12.
Gandini et al., "Metformin and cancer risk and mortality: A systematic review and meta-analysis taking into account biases and confounders", Cancer Prev Res, 2014, 7(9), 867-885.
Gerstein et al., "Basal Insulin and cardiovascular and other outcomes in dysglycemia", N Engl J Med, 2012, 367:319-28.
Gerstein et al., "Identifying novel biomarkers for cardiovascular events or death in people with dysglycemia", Circulation, 2015.
Ho et al., "Clinical and genetic correlates of growth differentiation factor 15 in the community", Clinical Chemistry, 2012, 58:11 1582-1591.
Holman et al., "10-year follow-up of intensive glucose control in type 2 diabetes", N Engl J Med, 2008, 359:1577-89.
Hong et al., "GDF15 is a novel biomarker for impaired fasting glucose", Diabetes Metab J, 2014, 38:472-479.
International Search Report and Written Opinion dated Mar. 24, 2017 issued in International patent application No. PCT/EP2016/082163.
Kalko et al., "Transcriptomic profiling of TK2 deficient human skeletal muscle suggests a role for the p53 signalling pathway and identifies growth and differentiation factor-15 as a potential novel biomarker for mitochondrial myopathies", BMC Genomics, 2014, 15:91.
Karlin and Altschul, "Applications and statistics for multiple high-scoring segments in molecular sequences", Proc. Natl. Acad. Sci., 1993, vol. 90, pp. 5873-5877.
Knowler et al., "Reduction in the incidence of type 2 diabetes with lifestyle intervention or metformin", The New England Journal of Medicine, 2002, 346, 393-103.
Koene et al., "Serum GDF15 levels correlate to mitochondrial disease severity and myocardial strain, but not to disease progression in adult m.3243A>G carriers", JIMD Reports, 2015.
Madiraju et al., "Metformin suppresses gluconeogenesis by inhibiting mitochondrial glycerophosphate dehydrogenase", Nature, 2014, 510, 542-6.
Martin-Montalvo et al., "Metformin improves healthspan and lifespan in mice", Nature Communications, 2013, 4:2192.
Matthews et al., "Homeostasis model assessment: insulin resistance and β-cell function from fasting plasma glucose and insulin concentrations in man", Diabetologia, 1985, 28:412-419.
Mazagova et al., "Genetic deletion of growth differentiation factor 15 augments renal damage in both type 1 and type 2 models of diabetes", Am J Physiol Renal Physiol, 2013, 305:F1249-F1264.
Miller et al., "Biguanides suppress hepatic glucagon signalling by decreasing production of cyclic AMP", Nature, 2013, 494, 256-260.

Natali and Ferrannini, "Effects of metformin and thiazolidinediones on suppression of hepatic glucose production and stimulation of glucose uptake in type 2 diabetes: a systematic review", Diabetologia, 2006, 49:434-441.
Owen et al., "Evidence that metformin exerts its anti-diabetic effects through inhibition of complex 1 of the mitochondrial respiratory chain", Biochem. J., 2000, 348, 607-614.
Plancade et al., "Generalization of the normal-exponential model: exploration of a more accurate parametrisation for the signal distribution on Illumina BeadArrays", BMC Bioinformatics, 2012, 13:329.
Preusch et al., "GDF-15 protects from macrophage accumulation in a mouse model of advanced atherosclerosis", European Journal of Medical Research, 2013, 18:19.
Ramachandran et al., "The Indian Diabetes Prevention Programme shows that lifestyle modification and metformin prevent type 2 diabetes in Asian Indian subjects with impaired glucose tolerance (IDPP-1)", 2006, Diabetologia, 49:289-297.
Schlittenhardt et al., "Involvement of growth differentiation factor—15/macrophage inhibitory cytokine-1 (GDF-15/MIC-1) in oxLDL-induced apoptosis of human macrophages in vitro and in arteriosclerotic lesions", Cell Tissue Res, 2004, 318:325-333.
Schmid et al., "Comparison of normalization methods for Illumina BeadChip HumanHT-12 v3", BMC Genomics, 2010, 11:349.
Scott et al., "Thienopyridone drugs are selective activators of AMP-activated protein kinase β1-containing complexes", Chemistry & Biology, 2008, 15, 1220-1230.
Steinberg, "AMPK and the endocrine control of energy metabolism", Molecular and Cellular Endocrinology, 2013, 366, 125-126.
Stevens et al., "Cancer outcomes and all-cause mortality in adults allocated to metformin: systematic review and collaborative meta-analysis of randomised clinical trials", Diabetologia, 2012, 55:2593-2603.
Su et al., Di-San Junyi, Daxue Xuebao Bianjibu, 2013, vol. 35(17), pp. 1862-1865 and English translation.
Su et al., Di-San Junyi, Daxue Xuebao Bianjibu, 2013, vol. 35(17), pp. 1862-1865, Abstract Only.
Thompson et al., "Clustal W: improving the sensitivity of progressive multiple sequence alignment through sequence weighting, position-specific gap penalties and weight matrix choice", Nucleic Acids Research, 1994, vol. 22, No. 22, 4673-4680.
Tomova et al., "Anti-Müllerian hormone in women with polycystic ovary syndrome before and after therapy with metformin", Hormone and Metabolic Research, 2011, vol. 43, No. 10, 723-727.
Tsai et al., "TGF-b superfamily cytokine MIC-1/GDF15 is a physiological appetite and body weight regulator", PLoS One, 2013, vol. 8, issue 2, e55174.
Wilcock and Bailey, "Accumulation of metformin by tissues of the normal and diabetic mouse", Xenobiotica, 1994, vol. 24, No. 1, 49-57.
Williams et al., "Metformin induces a senescence-associated gene signature in breast cancer cells", J Health Care Poor Underserved., 2013,24(10): 93-103.
Doll, A.P. et al., "GDF15 mediates the effects of metformin on body weight and energy balance" Nature, 578:444-448 (2000).
Zhang et al., "CGRRF1 as a novel biomarker of tissue response to metformin in the context of obesity", Gynecologic Oncology, 2014, vol. 133, No. 1, 83-89, and abstract.
Zhou et al., "Heritability of variation in glycaemic response to metformin: a genome-wide complex trait analysis", Diabetes-endocrinology, 2014, vol. 2, 481-487.

* cited by examiner

SEQUENCE LISTING

<160> NUMBER OF SEQ ID NOS: 1

<210> SEQ ID NO 1
<211> LENGTH: 308
<212> TYPE: PRT
<213> ORGANISM: Homo sapiens

```
<400> SEQUENCE: 1

Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
                20                  25                  30

Ala Glu Ala Ser Arg Ala Ser Phe Pro Gly Pro Ser Glu Leu His Ser
            35                  40                  45

Glu Asp Ser Arg Phe Arg Glu Leu Arg Lys Arg Tyr Glu Asp Leu Leu
        50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
                100                 105                 110

Gly Leu Pro Glu Ala Ser Arg Leu His Arg Ala Leu Phe Arg Leu Ser
            115                 120                 125

Pro Thr Ala Ser Arg Ser Trp Asp Val Thr Arg Pro Leu Arg Arg Gln
130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
            195                 200                 205

Arg Cys Cys Arg Leu His Thr Val Arg Ala Ser Leu Glu Asp Leu Gly
        210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300

Cys His Cys Ile
305
```

GROWTH DIFFERENTIATION FACTOR 15 AS BIOMARKER FOR METFORMIN

This application is a Divisional application of U.S. application Ser. No. 16/064,341, filed on Jun. 20, 2018, which is a 371 application of International Application No. PCT/EP2016/082163, filed on Dec. 21, 2016, and claims priority to European Application No. EP 15202424.6, filed on Dec. 23, 2015, all of which are incorporated by reference in their entirety.

The present invention relates to metformin for use in treating a patient, wherein the patient exhibits an increased level of GDF15 in response to metformin treatment; to methods of identifying a patient who will benefit or who will not benefit from metformin treatment; methods of treating a patient at risk of developing or suffering from a disease or disorder comprising administering therapeutically effective amount of metformin; methods of adapting the dosage of metformin; the usage of GDF15 as biomarker for identifying a patient who will benefit or who will not benefit from metformin treatment, kits for use in identifying a patient who will benefit from metformin treatment and the use of the kits, as well as methods of treating a patient or who will not benefit from metformin treatment.

BACKGROUND

Metformin is currently the most widely used glucose lowering agent in the world. It has been studied extensively in both animal models and humans and has a number of clinical and biochemical properties. Clinical trials have clearly and reproducibly shown that it effectively lowers glucose levels and it has been used for that purpose since 1957. They have also shown that its metabolic effect is not limited to people with diabetes. Thus several trials have shown that it modestly reduces weight, and effectively reduces progression of dysglycemia from impaired glucose tolerance to diabetes[1,2]. Other research has strongly suggested that it may reduce the incidence of ischemic heart disease and mortality both in ambulatory participants and in those with other illnesses, and has raised the possibility that it may reduce the development or progression of a variety of malignancies[3,4], as well as increase in lifespan[37,38,39]. Indeed, more than 1500 clinical trials involving metformin are currently underway in many different types of diseases (www.clinicaltrials.gov).

The foregoing clinical properties of the drug have fueled intense interest for more than 70 years. It is therefore remarkable that much of its mechanism of action remains unknown. Clinical studies have shown the primary mechanism by which metformin lowers blood sugar is through reductions in hepatic glucose production either directly or by potentiating the effects of insulin[5]. Biochemically, there is growing evidence that metformin elicits its therapeutic effects through disruption of mitochondrial function[6-8] and activation of the AMP-activated protein kinase—a crucial molecule that regulates cellular energy balance and also inhibits inflammation and improves insulin action[9,10]. Despite this body of research, it is particularly interesting that other than glucose and glycated hemoglobin, no reliable biomarker for metformin's presence or dose has been identified. This clearly limits the ability to assess the effects of metformin in people with normal glucose homeostasis. Furthermore, at present it takes months to find out (e.g. via HbA1c reduction) whether treatment with metformin is actually beneficial to a patient, i.e. to determine whether a patient is a metformin responder. Due to the low-turn-over rate of erythrocytes, which are the basis of the HbA1c measurements, it takes 3-6 months to determine whether metformin treatment is successful or not in a particular patient. During this time frame of whether a patient is responsive to metformin treatment, the patient not responding to metformin treatment basically remains without treatment. During this long period of not being treated, further detrimental effects may occur in the patient such as microvascular complications including diabetic nephropathy, retinopathy, and foot ulcers, as well as macrovascular complications including myocardial infarction and cardiovascular death. It would thus be highly desirable to decrease the diagnostic timeframe of the efficacy of metformin treatment to ensure that those patients not responding to metformin treatment may obtain an alternate, more suitable treatment as soon as possible. Furthermore, such decrease in the diagnostic timeframe of the efficacy of metformin treatment also reduce healthcare costs as patients not responding to metformin treatment do not need to be treated with metformin for months without effect, resulting in reduced cost of metformin treatment and in reduced costs for the treatment of follow-up complications due to a belated therapy with an alternate, more suitable treatment.

SUMMARY OF THE INVENTION

In a first aspect, the present invention relates to metformin for use in treating a patient, wherein the patient exhibits an increased level of GDF15 in response to metformin treatment, and wherein the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease or reduced longevity.

In a second aspect, the present invention relates to a method of identifying a patient or a group of patients who will benefit from metformin treatment, comprising the steps of
  (i) administering an effective amount of metformin to a patient,
  (ii) determining the level of GDF15 in a patient's sample, and
  (iii) comparing the GDF15 level determined in step (ii) to that of a reference, wherein an increased level of GDF15 is indicative of a response of the patient to metformin administration.

In a third aspect, the present invention relates to a pharmaceutical composition comprising metformin and at least one pharmaceutically acceptable carrier, adjuvant and/or excipient for use in treating diabetes, in particular diabetes I or II, in a patient, wherein the patient exhibits an increased level of GDF15 in response to metformin treatment.

In a fourth aspect, the present invention relates to a method of adapting the dosage of metformin comprising
  (i) administering metformin to a patient,
  (ii) determining the level of GDF15 in a patient's sample
  (iii) comparing the GDF15 level determined in step (ii) to a reference, and (iv) adjusting the dosage of metformin in that the treatment with metformin is stopped in case the level of GDF15 is not increased, and the dosage of metformin is maintained or increased in case the level of GDF15 is increased.

In a fifth aspect, the present invention relates to the use of GDF15 as biomarker for identifying a patient or a group of patients who will benefit from metformin treatment.

In a sixth aspect, the present invention relates to a kit for use in identifying a patient or a group of patients who will benefit from metformin treatment, comprising means for detecting the expression level of GDF15

In a seventh aspect, the present invention relates to the use of the kit of the sixth aspect in the method of the second or fourth aspect.

In an eighth aspect, the present invention relates to a method of treating a patient at risk of developing or suffering from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease and reduced longevity, comprising the step of administering to said patient a therapeutically effective amount of metformin, wherein said patient exhibits an increased level of GDF15 in response to (an initial) metformin treatment.

In a ninth aspect, the present invention relates to a method of treating a patient or a group of patients who will benefit from metformin treatment, comprising the steps of
  (i) administering an effective amount of metformin to a patient,
  (ii) determining the level of GDF15 in a patient's sample, and
  (iii) comparing the GDF15 level determined in step (ii) to that of a reference,
  (iv) continuing administration of metformin to those patients exhibiting an increased level of GDF15.

In a tenth aspect, the present invention relates to a method of treating a patient or a group of patients who will not benefit from metformin treatment, comprising the steps of
  (i) administering an effective amount of metformin to a patient,
  (ii) determining the level of GDF15 in a patient's sample, and
  (iii) comparing the GDF15 level determined in step (ii) to that of a reference,
  (iv) discontinuing administration of metformin to those patients exhibiting an unaltered or decreased level of GDF15,
and optionally
  (v) administering an alternative treatment to those patients exhibiting an unaltered or decreased level of GDF15.

In an eleventh aspect, the present invention relates to a method of identifying a patient or a group of patients who will not benefit from metformin treatment, comprising the steps of
  (i) administering an effective amount of metformin to a patient,
  (ii) determining the level of GDF15 in a patient's sample, and
  (iii) comparing the GDF15 level determined in step (ii) to that of a reference, wherein an unaltered or decreased level of GDF15 is indicative of a patient not responding to metformin administration.

In a twelfth aspect, the present invention relates to sulfonylureas, dopamine agonist, DPP-4 inhibitors, glucagon-like peptides, meglitinides, amylinomimetic, alpha-glucosidase inhibitors, SGLT2 inhibitors, and/or thiazolidinediones for use in treating a patient, wherein the patient exhibits an unaltered or decreased level of GDF15 in response to metformin treatment, and wherein the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease or reduced longevity.

In a thirteenth aspect, the present invention relates to a method of shortening the time for determining whether a patient responds to metformin administration, comprising the steps of
  (i) administering an effective amount of metformin to a patient,
  (ii) determining the level of GDF15 in a patient's sample, and
  (iii) comparing the GDF15 level determined in step (ii) to that of a reference,
  wherein an increased level of GDF15 is indicative of a patient responding to metformin administration, and wherein an unaltered or decreased level of GDF15 is indicative of a patient not responding to metformin administration.

In a fourteenth aspect, the present invention relates to a method of preventing, delaying, and/or treating diabetes associated complications in a patient, comprising the steps of
  (i) administering an effective amount of metformin to a patient
  (ii) determining the level of GDF15 in a patient's sample, and
  (iii) comparing the GDF15 level determined in step (ii) to that of a reference,
  (iv) continuing metformin administration to those patients exhibiting an increased level of GDF15, and discontinuing administration of metformin to those patients exhibiting an unaltered or decreased level of GDF15,
and optionally
  (v) administering an alternative treatment to those patients exhibiting an unaltered or decreased level of GDF15.

In a fifteenth aspect, the present invention relates to a method of preventing, delaying, and/or treating diabetes associated complications in a patient, comprising the steps of
  (i) administering an effective amount of metformin to a patient,
  (ii) determining the level of GDF15 in a patient's sample, and
  (iii) comparing the GDF15 level determined in step (ii) to that of a reference, wherein an increased level of GDF15 is indicative of the patient responding to metformin treatment, and an unaltered or decreased level of GDF15, is indicative of the patient not responding to metformin treatment, and optionally (iv) considering an alternative treatment for those patients exhibiting an unaltered or decreased level of GDF15 in order to reduce diabetes associated complications in said patient.

LIST OF FIGURES

FIG. 1: Relationship Between GDF15 levels and Metformin Use. Models 1-5 in Panel A display the odds of being on metformin for every 1 standard deviation higher natural logarithm-transformed GDF15 level, after accounting for the clinical factors associated with metformin use plus all of the 237 available biomarkers. Models 1-4 in Panel B display the odds of being on metformin for every 1 standard deviation higher natural logarithm-transformed GDF15 level, after accounting for just the clinical factors associated with metformin use.

Figure 2:
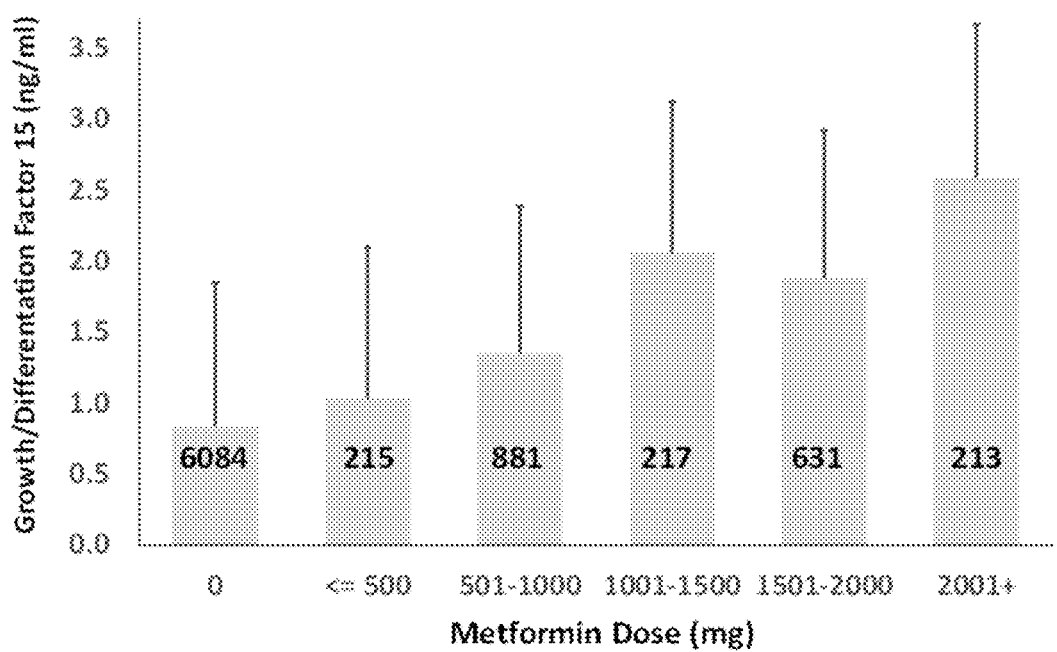

FIG. 2: Relationship Between Metformin Dose and GDF15 Levels. The concentration of GDF15 in people taking varying doses of metformin is shown. The means and the upper standard errors of the mean are shown.

Figure 3:
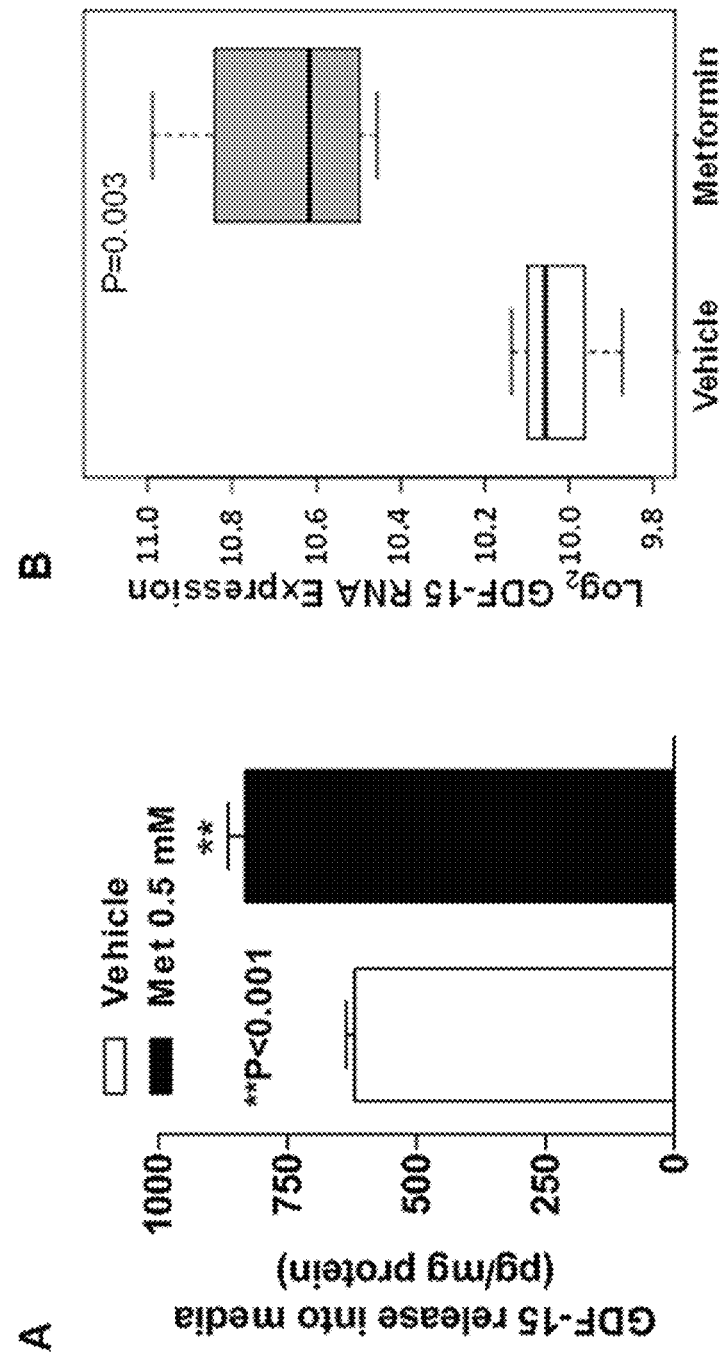

FIG. 3: GDF15 Response to Metformin. Panel A displays the mean concentration of GDF15 and the SEM in the media of cultured primary hepatocytes (based on 4 independent experiments assayed in triplicate) from 4 male C57Bl6 wild-type mice exposed to either vehicle or metformin (0.5 mmol/L) for 24 hours is shown. Panel B displays the relative GDF15 messenger RNA expression (in logarithm base 2 units) in response to either vehicle or metformin (0.5 mM).

Figure 4:
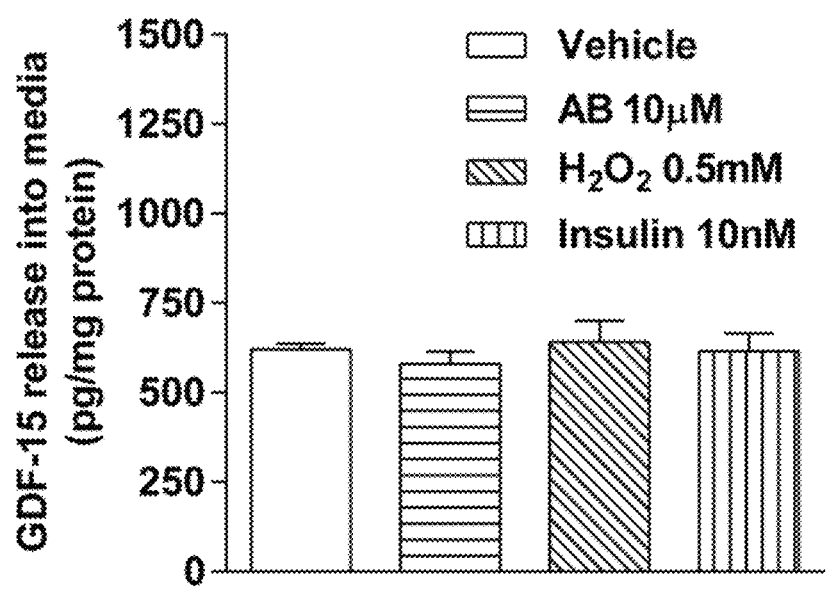

FIG. 4: Effect of AMPK activator A769662 (AB-10 μM), hydrogen peroxide ($H_2O_2$-0.5 mM) and insulin (10 nM) on GDF15 release. After 24 hours of exposure of primary hepatocytes from 4 C57Bl6 wild-type mice, none of these substances affected the concentration of GDF15 (based on 2 independent experiments assayed in triplicate) in the media versus no exposure. Data are expressed as mean (SEM).

Figure 5:
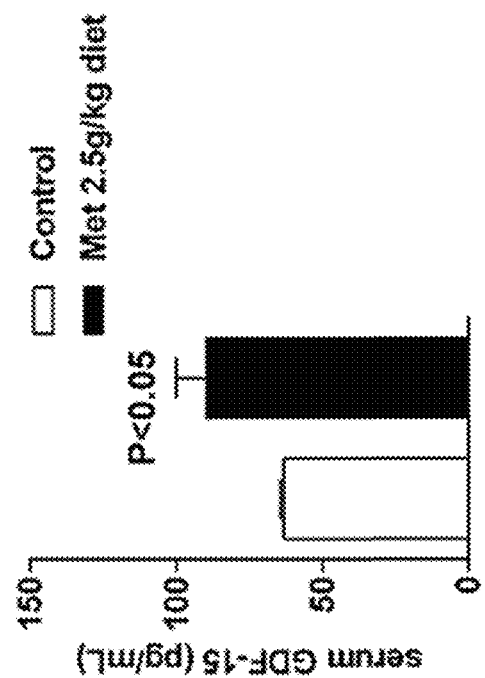
Figure 5:
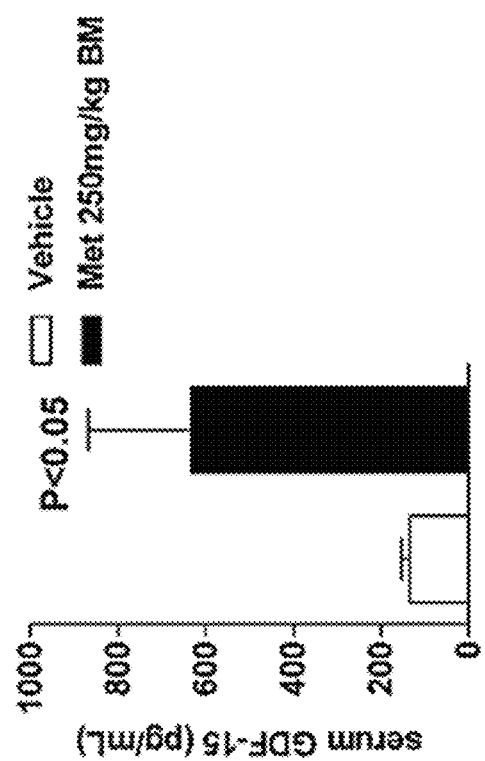

FIG. 5: Effect of Metformin on Serum GDF15 Concentrations in Wild Type Mice. GDF15 concentrations measured in tail vein samples obtained 90 minutes after injection with either metformin 250 mg/kg body weight (N=6) or vehicle (N=6) are shown in Panel A. Concentrations measured in tail vein samples obtained in wild-type mice fed a 60% high-fat diet for 5 weeks followed by 60% high-fat diet containing either no drug (N=4) or 2.5 g/kg metformin (N=4) for an additional 5 weeks are shown in Panel B.

---

List of Sequences amino acid sequence of human GDF15
(UniProtKB/Swiss-Prot: Q99988.3):
SEQ ID NO: 1
MPGQELRTVNGSQMLLVLLVLSWLPHGGALSLAEASRASFPGPSEL

HSEDSRFRELRKRYEDLLTRLRANQSWEDSNTDLVPAPAVRILTPEV

RLGSGGHLHLRISRAALPEGLPEASRLHRALFRLSPTASRSWDVTRP

LRRQLSLARPQAPALHLRLSPPPSQSDQLLAESSSARPQLELHLRPQ

AARGRRRARARNGDHCPLGPGRCCRLHTVRASLEDLGWADWVLSP

---

List of Sequences

REVQVTMCIGACPSQFRAANMHAQIKTSLHRLKPDTVPAPCCVPASY

NPMVLIQKTDTGVSLQTYDDLLAKDCHCI

---

LIST OF REFERENCES

1. Knowler W C, Barrett-Connor E, Fowler S E, et al. Reduction in the incidence of type 2 diabetes with lifestyle intervention or metformin. N Engl J Med 2002; 346:393-403.
2. Ramachandran A, Snehalatha C, Mary S, Mukesh B, Bhaskar A D, Vijay V. The Indian Diabetes Prevention Programme shows that lifestyle modification and metformin prevent type 2 diabetes in Asian Indian subjects with impaired glucose tolerance (IDPP-1). Diabetologia 2006; 49:289-97.
3. Gandini S, Puntoni M, Heckman-Stoddard B M, et al. Metformin and cancer risk and mortality: a systematic review and meta-analysis taking into account biases and confounders. Cancer Prev Res (Phila) 2014 September; 7 (9):867-85 doi: 10 1158/1940-6207 CAPR-13-0424 Epub 2014 Jul. 1; 7:867-85.
4. Stevens R J, Ali R, Bankhead C R, et al. Cancer outcomes and all-cause mortality in adults allocated to metformin: systematic review and collaborative meta-analysis of randomised clinical trials. Diabetologia 2012; 55:2593-603.
5. Natali A, Ferrannini E. Effects of metformin and thiazolidinediones on suppression of hepatic glucose production and stimulation of glucose uptake in type 2 diabetes: a systematic review. Diabetologia 2006; 49:434-41.
6. Owen M R, Doran E, Halestrap A P. Evidence that metformin exerts its anti-diabetic effects through inhibition of complex 1 of the mitochondrial respiratory chain. Biochem J 2000; 348 Pt 3:607-14.
7. Miller R A, Chu Q, Xie J, Foretz M, Viollet B, Birnbaum M J. Biguanides suppress hepatic glucagon signalling by decreasing production of cyclic AMP. Nature 2013; 494: 256-60.
8. Madiraju A K, Erion D M, Rahimi Y, et al. Metformin suppresses gluconeogenesis by inhibiting mitochondrial glycerophosphate dehydrogenase. Nature 2014; 510:542-6.
9. Steinberg G R. AMPK and the endocrine control of energy metabolism. Mol Cell Endocrinol 2013; 366:125-6.
10. Fullerton M D, Steinberg G R, Schertzer J D. Immunometabolism of AMPK in insulin resistance and atherosclerosis. Mol Cell Endocrinol 2013; 366:224-34.
11. Gerstein H C, Bosch J, Dagenais G R, et al. Basal insulin and cardiovascular and other outcomes in dysglycemia. N Engl J Med 2012; 367:319-28.
12. Bosch J, Gerstein H C, Dagenais G R, et al. n-3 fatty acids and cardiovascular outcomes in patients with dysglycemia. N Engl J Med 2012; 367:309-18.
13. Gerstein H C, Pare G, McQueen M J, et al. Identifying Novel Biomarkers for Cardiovascular Events or Death in People With Dysglycemia. Circulation 2015.
14. Fullerton M D, Galic S, Marcinko K, et al. Single phosphorylation sites in Acc1 and Acc2 regulate lipid homeostasis and the insulin-sensitizing effects of metformin. Nat Med 2013; 19:1649-54.

15. Plancade S, Rozenholc Y, Lund E. Generalization of the normal-exponential model: exploration of a more accurate parametrisation for the signal distribution on Illumina BeadArrays. BMC Bioinformatics 2012; 13:329.
16. Schmid R, Baum P, Ittrich C, et al. Comparison of normalization methods for Illumina BeadChip HumanHT-12 v3. BMC Genomics 2010; 11:349.
17. Ford R J, Fullerton M D, Pinkosky S L, et al. Metformin and salicylate synergistically activate liver AMPK, inhibit lipogenesis and improve insulin sensitivity. Biochem J 2015; 468:125-32.
18. Wilcock C, Bailey C J. Accumulation of metformin by tissues of the normal and diabetic mouse. Xenobiotica 1994; 24:49-57.
19. Cool B, Zinker B, Chiou W, et al. Identification and characterization of a small molecule AMPK activator that treats key components of type 2 diabetes and the metabolic syndrome. Cell Metab 2006; 3:403-16.
20. Scott J W, van Denderen B J, Jorgensen S B, et al. Thienopyridone drugs are selective activators of AMP-activated protein kinase beta1-containing complexes. Chem Biol 2008; 15:1220-30.
21. Ding Q, Mracek T, Gonzalez-Muniesa P, et al. Identification of macrophage inhibitory cytokine-1 in adipose tissue and its secretion as an adipokine by human adipocytes. Endocrinology 2009; 150:1688-96.
22. Schlittenhardt D, Schober A, Strelau J, et al. Involvement of growth differentiation factor-15/macrophage inhibitory cytokine-1 (GDF-15/MIC-1) in oxLDL-induced apoptosis of human macrophages in vitro and in arteriosclerotic lesions. Cell Tissue Res 2004; 318:325-33.
23. Williams C C, Singleton B A, Llopis S D, Skripnikova E V. Metformin induces a senescence-associated gene signature in breast cancer cells. J Health Care Poor Underserved 2013; 24:93-103.
24. Breit S N, Johnen H, Cook A D, et al. The TGF-beta superfamily cytokine, MIC-1/GDF15: a pleotrophic cytokine with roles in inflammation, cancer and metabolism. Growth Factors 2011; 29:187-95.
25. Kalko S G, Paco S, Jou C, et al. Transcriptomic profiling of TK2 deficient human skeletal muscle suggests a role for the p53 signalling pathway and identifies growth and differentiation factor-15 as a potential novel biomarker for mitochondrial myopathies. BMC Genomics 2014; 15:91.
26. Fujita Y, Ito M, Kojima T, Yatsuga S, Koga Y, Tanaka M. GDF15 is a novel biomarker to evaluate efficacy of pyruvate therapy for mitochondrial diseases. Mitochondrion 2015; 20:34-42.
27. Koene S, de L P, van Tienoven D H, et al. Serum GDF15 Levels Correlate to Mitochondrial Disease Severity and Myocardial Strain, but Not to Disease Progression in Adult m.3243A>G Carriers. JIMD Rep 2015.
28. Preusch M R, Baeuerle M, Albrecht C, et al. GDF-15 protects from macrophage accumulation in a mousemodel of advanced atherosclerosis. Eur J Med Res 2013; 18:19.
29. de Jager S C, Bermudez B, Bot I, et al. Growth differentiation factor 15 deficiency protects against atherosclerosis by attenuating CCR2-mediated macrophage chemotaxis. J Exp Med 2011; 208:217-25.
30. Mazagova M, Buikema H, van B A, et al. Genetic deletion of growth differentiation factor 15 augments renal damage in both type 1 and type 2 models of diabetes. Am J Physiol Renal Physiol 2013; 305:F1249-F64.
31. Tsai V W, Macia L, Johnen H, et al. TGF-b superfamily cytokine MIC-1/GDF15 is a physiological appetite and body weight regulator. PLoS ONE 2013; 8:e55174.
32. Holman R R, Paul S K, Bethel M A, Matthews D R, Neil H A. 10-Year Follow-up of Intensive Glucose Control in Type 2 Diabetes. N Engl J Med 2008; 359:1577-89.
33. Martin-Montalvo A, Mercken E M, Mitchell S J, et al. Metformin improves healthspan and lifespan in mice. Nat Commun 2013; 4:2192.
34. Ho J E, Mahajan A, Chen M H, et al. Clinical and genetic correlates of growth differentiation factor 15 in the community. Clin Chem 2012; 58:1582-91.
35. Adela R, Banerjee S K. GDF-15 as a Target and Biomarker for Diabetes and Cardiovascular Diseases: A Translational Prospective. J Diabetes Res 2015; 2015: 490842.
36. Hong J H, Chung H K, Park H Y, et al. GDF15 Is a Novel Biomarker for Impaired Fasting Glucose. Diabetes Metab J 2014; 38:472-9.
37. Castillo-Quan J J, Kinghorn K J, Bjedov Genetics and Pharmacology of Longevity: The Road to Therapeutics for Healthy Aging. Adv Genetics 2015; 90, 1-73.
38. Martin-Montalvo A, Mercken E M, Mitchell S J et al. Metformin improves healthspan and lifespan in mice. Nature Communic. 2013; 4: 2192, 1-9.
39. Bannister C A, Holden S E, Jenkins-Jones S et al. Can people with type 2 diabetes live longer than those without? A comparison of mortality in people initiated with metformin or sulphonylurea monotherapy and matched, non-diabetic controls. Diabetes, Obesity and Metabolism 2014; 16: 1165-1173.
40. Gerstein H C, Pare G, McQueen M J, Heinz Haenel, et al. Identifying Novel Biomarkers for Cardiovascular Events or Death in People With Dysglycemia. Circulation. published online before print Oct. 30, 2015

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used in this specification and the appended claims, the singular forms "a", "an", and "the" include plural referents, unless the content clearly dictates otherwise.

The term "about" when used in connection with a numerical value is meant to encompass numerical values within a range having a lower limit that is 5% smaller than the indicated numerical value and having an upper limit that is 5% larger than the indicated numerical value.

Amino acids are organic compounds composed of amine (—NH2) and carboxylic acid (—COOH) functional groups, along with a side-chain specific to each amino acid. Typically, amino acids are classified by the properties of their side-chain into four groups: the side-chain can make an amino acid a weak acid or a weak base, a hydrophile if the side-chain is polar or a hydrophobe if it is nonpolar.

In the context of the different aspects of present invention, the term "peptide" refers to a short polymer of amino acids linked by peptide bonds. It has the same chemical (peptide) bonds as proteins, but is commonly shorter in length. The shortest peptide is a dipeptide, consisting of two amino acids joined by a single peptide bond. There can also be a tripeptide, tetrapeptide, pentapeptide, etc. Preferably, the peptide has a length of up to 8, 10, 12, 15, 18 or 20 amino acids. A peptide has an amino end and a carboxyl end, unless it is a cyclic peptide.

In the context of the different aspects of present invention, the term "polypeptide" refers to a single linear chain of amino acids bonded together by peptide bonds and preferably comprises at least about 21 amino acids. A polypeptide can be one chain of a protein that is composed of more than one chain or it can be the protein itself if the protein is composed of one chain.

In the context of the different aspects of present invention, the term "protein" refers to a molecule comprising one or more polypeptides that resume a secondary and tertiary structure and additionally refers to a protein that is made up of several polypeptides, i.e. several subunits, forming quaternary structures. In the context of present invention, the primary structure of a protein or polypeptide is the sequence of amino acids in the polypeptide chain. The secondary structure in a protein is the general three-dimensional form of local segments of the protein. It does not, however, describe specific atomic positions in three-dimensional space, which are considered to be tertiary structure. In proteins, the secondary structure is defined by patterns of hydrogen bonds between backbone amide and carboxyl groups. The tertiary structure of a protein is the three-dimensional structure of the protein determined by the atomic coordinates. The quaternary structure is the arrangement of multiple folded or coiled protein or polypeptide molecules molecules in a multi-subunit complex. The terms "amino acid chain" and "polypeptide chain" are used synonymously in the context of present invention.

Proteins and polypeptide of the present invention (including protein derivatives, protein variants, protein fragments, protein segments, protein epitops and protein domains) can be further modified by chemical modification. This means such a chemically modified polypeptide comprises other chemical groups than the 20 naturally occurring amino acids. Examples of such other chemical groups include without limitation glycosylated amino acids and phosphorylated amino acids. Chemical modifications of a polypeptide may provide advantageous properties as compared to the parent polypeptide, e.g. one or more of enhanced stability, increased biological half-life, or increased water solubility. Chemical modifications applicable to the variants usable in the present invention include without limitation: PEGylation, glycosylation of non-glycosylated parent polypeptides, or the modification of the glycosylation pattern present in the parent polypeptide. The protein may also have non-peptide groups attached, such as e.g. prosthetic groups or cofactors.

Growth differentiation factor 15 (GDF15) is a protein belonging to the transforming growth factor beta superfamily and plays a role in regulating inflammatory and apoptotic pathways in injured tissues as well as during disease processes (UniProtKB/Swiss-Prot. Accession number: Q99988.3). GDF15 is also known as TGF-PL, macrophage inhibitory cytokine-1 (MIC-1), PDF, placental bone morphogenetic protein B (PLAB), and placental transforming growth factor β (PTGFB). GDF15 mRNA is most abundant in the liver, with lower levels seen in some other tissues. Its expression in liver can be significantly up-regulated in during injury of organs such as liver, kidney, heart, and the lung. The GDF15 gene (also known as nonsteroidal anti-inflammatory drug-activated gene-1 (NAG-1)) is localized on chromosome 19p 12-13.1, and GDF15 is expressed as a 40-kDa propeptide that is cleaved in the endoplasmic reticulum to release a 25-kDa active circulating dimeric protein. Deletion of the GDF15 gene in mice results in increased atherosclerosis[28,29], diabetic kidney injury[30] and obesity due to increased appetite[31], suggest that GDF15 may counteract these effects, perhaps by suppressing inflammation[28-30]. These observations are also consistent with the literature suggesting that metformin is cardioprotective and may even increase longevity[32,33]. It is therefore notable that human studies have reported high GDF15 levels with cardiovascular disease, diabetes and impaired kidney function[34-36].

As used herein, the term "variant" is to be understood as a polypeptide or protein which differs in comparison to the polypeptide or protein from which it is derived by one or more changes in its length or sequence. The polypeptide or protein from which a polypeptide variant or protein variant is derived is also known as the parent polypeptide or protein. The term "variant" comprises "fragments" or "derivatives" of the parent molecule. Typically, "fragments" are smaller in length or size than the parent molecule, whilst "derivatives" exhibit one or more differences in their sequence in comparison to the parent molecule. Also encompassed modified molecules such as but not limited to post-translationally modified proteins (e.g. glycosylated, biotinylated, phosphorylated, ubiquitinated, palmitoylated, or proteolytically cleaved proteins). A variant may be constructed artificially, preferably by gene-technological means whilst the parent polypeptide or protein is a wild-type polypeptide or protein. However, also naturally occurring variants are to be understood to be encompassed by the term "variant" as used herein. Further, the variants usable in the present invention may also be derived from homologs, orthologs, or paralogs of the parent molecule or from artificially constructed variants, provided that the variant exhibits at least one biological activity of the parent molecule, i.e. is functionally active.

A "variant" as used herein, can be characterized by a certain degree of sequence identity to the parent polypeptide or parent protein from which it is derived. More precisely, a protein variant in the context of the present invention exhibits at least 80% sequence identity to its parent polypeptide. The term "at least 80% sequence identity" is used throughout the specification with regard to polypeptide sequence comparisons. This expression preferably refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide. Preferably, the polypeptide in question and the reference polypeptide exhibit the indicated sequence identity over a continuous stretch of 20, 30, 40, 45, 50, 60, 70, 80, 90, 100 or more amino acids or over the entire length of the reference polypeptide.

A derivative of the present invention may exhibit a total number of up to 100 (up to 1, 2, 3, 4, 5, 6, 7, 8, 9, 10, 15, 20, 25, 30, 35, 40, 45, or 50) changes in the amino acid sequence (i.e. exchanges, insertions, deletions, N-terminal truncations, and/or C-terminal truncations). The amino acid exchanges may be conservative and/or non-conservative. In preferred embodiments, a derivative of the present invention differs from the polypeptide or protein or domain from which it is derived by up to 1, 2, 3, 4, 5, 6, 7, 8, 9, 10, 15, 20, 25, 30, 35, 40, 45, or 50 amino acid exchanges, preferably conservative amino acid changes.

The terms "deletion variant" and "fragment" are used interchangeably herein. Such variants comprise N-terminal truncations, C-terminal truncations and/or internal deletions. A fragment may be naturally occurring (e.g. splice variants) or it may be constructed artificially, preferably by gene-technological means. Preferably, a fragment (or deletion variant) has a deletion of up to 1, 2, 3, 4, 5, 6, 7, 8, 9, 10, 15, 20, 25, 30, 35, 40, 45, 50, 55, 60, 65, 70, 75, 80, 85, 90, 95, or 100 amino acids at its N-terminus and/or at its C-terminus and/or internally as compared to the parent polypeptide, preferably at its N-terminus, at its N- and C-terminus, or at its C-terminus.

In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by SEQ ID, if not specifically indicated otherwise. The similarity of the amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90: 5873-5877), with hmmalign (HMMER package, http://hmmer.wustl.edu/) or with the CLUSTAL algorithm (Thompson, J. D., Higgins, D. G. & Gibson, T. J. (1994) Nucleic Acids Res. 22, 4673-80) available e.g. on http://www.ebi.ac.uk/Tools/clustalw/ or on http://www.ebi.ac.uk/Tools/clustalw2/index.html or on http://npsa-pbil.ibcp.fr/cgi-bin/npsa_automat.pl?page=/NPSA/npsa_clustalw.html. Preferred parameters used are the default parameters as they are set on http://www.ebi.ac.uk/Tools/clustalw/ or http://www.ebi.ac.uk/Tools/clustalw2/index.html. The grade of sequence identity (sequence matching) may be calculated using e.g. BLAST, BLAT or BlastZ (or BlastX). A similar algorithm is incorporated into the BLASTN and BLASTP programs of Altschul et al. (1990) J. Mol. Biol. 215: 403-410. BLAST protein searches are performed with the BLASTP program, score=50, word length=3, to obtain amino acid sequences homologous to the parent polypeptide. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields. When percentages of sequence identity are referred to in the present application, these percentages are calculated in relation to the full length of the longer sequence, if not specifically indicated otherwise.

Additionally or alternatively, a deletion variant may occur not due to structural deletions of the respective amino acids as described above, but due to these amino acids being inhibited or otherwise not able to fulfil their biological function. Typically, such functional deletion occurs due to the insertions to or exchanges in the amino acid sequence that changes the functional properties of the resultant protein, such as but not limited to alterations in the chemical properties of the resultant protein (i.e. exchange of hydrophobic amino acids to hydrophilic amino acids), alterations in the post-translational modifications of the resultant protein (e.g. post-translational cleavage or glycosylation pattern), or alterations in the secondary or tertiary protein structure. Additionally or alternatively, a functional deletion may also occur due to transcriptional or post-transcriptional gene silencing (e.g. via siRNA) or the presence or absence of inhibitory molecules such as but not limited to protein inhibitors or inhibitory antibodies.

Semi-conservative and especially conservative amino acid substitutions, wherein an amino acid is substituted with a chemically related amino acid, are preferred. Typical substitutions are among the aliphatic amino acids, among the amino acids having aliphatic hydroxyl side chain, among the amino acids having acidic residues, among the amide derivatives, among the amino acids with basic residues, or the amino acids having aromatic residues. Changing from A, F, H, I, L, M, P, V, W or Y to C is semi-conservative if the new cysteine remains as a free thiol. Furthermore, the skilled person will appreciate that glycines at sterically demanding positions should not be substituted and that P should not be introduced into parts of the protein which have an alpha-helical or a beta-sheet structure.

The term "sample" or "sample of interest" are used interchangeably herein, referring to a part or piece of a tissue, organ or individual, typically being smaller than such tissue, organ or individual, intended to represent the whole of the tissue, organ or individual. Upon analysis a sample provides information about the tissue status or the health or diseased status of an organ or individual. Examples of samples include but are not limited to fluid samples such as blood, serum, plasma, synovial fluid, urine, saliva, and lymphatic fluid, or solid samples such as tissue extracts, cartilage, bone, synovium, and connective tissue. Analysis of a sample may be accomplished on a visual or chemical basis. Visual analysis includes but is not limited to microscopic imaging or radiographic scanning of a tissue, organ or individual allowing for morphological evaluation of a sample. Chemical analysis includes but is not limited to the detection of the presence or absence of specific indicators or alterations in their amount or level.

The term "reference sample" as used herein, refers to a sample which is analysed in a substantially identical manner as the sample of interest and whose information is compared to that of the sample of interest. A reference sample thereby provides a standard allowing for the evaluation of the information obtained from the sample of interest. A reference sample may be identical to the sample of interest except for one component which may be exchanged, missing or added.

The term "reference value" as used herein, refers to a value which is known to be indicative for a certain status. The reference value may represent an amount or a concentration of the biomarker(s) disclosed herein. The term "the level of said biomarker is altered, in particular increased or decreased, compared to a reference value", as used herein, means that the amount or concentration of said biomarker is by at least 5%, by at least 10%, by at least 20%, by at least 30%, by at least 40%, by at least 50%, by at least 60%, by at least 70%, by at least 80%, by at least 90%, by at least 100%, by at least 110%, by at least 120%, by at least 130%, by at least 140%, by at least at least 150%, by at least 200%, by at least 250%, by at least 300%, by at least 400%, or by at least 500% altered, in particular increased or decreased, compared to a reference value. The reference value is the level of said biomarker determined by measuring one or more reference samples isolated from one or more healthy individual. The reference value may be determined by measuring one or more reference samples, such as at least 1, at least 2, at least 5, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 1500, or at least 2000 reference samples, from one or more healthy subjects, such as at least 1, at least 2, at least 5, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 1500, or at least 2000 healthy subjects. Typically, one reference sample per subject is measured. It may be advantageous that at least two subjects are tested.

The reference value refers a threshold level with an upper value of the 95% confidence interval and belonging to the mean value calculated from healthy individuals. The 95% confidence interval and the mean value may be determined by techniques known in the art. For the determination of the mean value, at least two healthy subjects, in particular at least 5, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 1500, or at least 2000 healthy subjects, are tested. When the control is a threshold level, the term "the level of said at least one biomarker is increased (decreased) compared to a threshold level" is to be understood that "the level of said at least one biomarker is above (below) a threshold level".

The terms "lowered" or "decreased" level of protein refer to the level of such protein in the sample being reduced in comparison to the reference, in particular the reference sample or reference value. The terms "elevated" or "increased" level of a protein refers to the level of such protein in the sample being higher in comparison to the reference value or reference sample.

The term "disease" and "disorder" are used interchangeably herein, referring to an abnormal condition, especially an abnormal medical condition such as an illness or injury, wherein a tissue, an organ or an individual is not able to efficiently fulfil its function anymore. Typically, but not necessarily, a disease is associated with specific symptoms or signs indicating the presence of such disease. The presence of such symptoms or signs may thus, be indicative for a tissue, an organ or an individual suffering from a disease. An alteration of these symptoms or signs may be indicative for the progression of such a disease. A progression of a disease is typically characterised by an increase or decrease of such symptoms or signs which may indicate a "worsening" or "bettering" of the disease. The "worsening" of a disease is characterised by a decreasing ability of a tissue, organ or organism to fulfil its function efficiently, whereas the "bettering" of a disease is typically characterised by an increase in the ability of a tissue, an organ or an individual to fulfil its function efficiently. A tissue, an organ or an individual being at "risk of developing" a disease is in a healthy state but shows potential of a disease emerging. Typically, the risk of developing a disease is associated with early or weak signs or symptoms of such disease. In such case, the onset of the disease may still be prevented by treatment. Examples of a disease include but are not limited to traumatic diseases, inflammatory diseases, infectious diseases, cutaneous conditions, endocrine diseases, intestinal diseases, neurological disorders, joint diseases, genetic disorders, autoimmune diseases, and various types of cancer.

Typically, but not necessarily, a disease or injury is associated with specific "symptoms" or "signs" indicating the presence of such disease or injury. The presence of such symptoms or signs may thus, be indicative for a tissue, an organ or an individual suffering from a disease or injury. An alteration of these symptoms or signs may be indicative for the progression of such a disease or injury. A progression of a disease or injury is typically characterised by an increase or decrease of such symptoms or signs which may indicate a "worsening" or "bettering" of the disease or injury. The "worsening" of a disease or injury is characterised by a decreasing ability of a tissue, organ or organism to fulfil its function efficiently, whereas the "bettering" of a disease or injury is typically characterised by an increase in the ability of a tissue, an organ or an individual to fulfil its function efficiently. A tissue, an organ or an individual being at "risk of developing" a disease or injury is in a healthy state but shows potential of a disease or injury emerging. Typically, the risk of developing a disease or injury is associated with early or weak signs or symptoms of such disease. In such case, the onset and/or progression of the disease or injury may still be prevented by treatment.

"Symptoms" of a disease are implication of the disease noticeable by the tissue, organ or organism having such disease and include but are not limited to pain, weakness, tenderness, strain, stiffness, and spasm of the tissue, an organ or an individual. "Signs" or "signals" of a disease include but are not limited to the change or alteration such as the presence, absence, increase or elevation, decrease or decline, of specific indicators such as biomarkers or molecular markers, or the development, presence, or worsening of symptoms. Symptoms of pain include, but are not limited to an unpleasant sensation that may be felt as a persistent or varying burning, throbbing, itching or stinging ache.

The term "indicator" as used herein, refers to a sign or signal for a condition or is used to monitor a condition. Such a "condition" refers to the biological status of a cell, tissue or organ or to the health and/or disease status of an individual. An indicator may be the presence or absence of a molecule, including but not limited to peptide, protein, and nucleic acid, or may be a change in the expression level or pattern of such molecule in a cell, or tissue, organ or individual. An indicator may be a sign for the onset, development or presence of a disease in an individual or for the further progression of such disease. An indicator may also be a sign for the risk of developing a disease in an individual. The terms "lowered" or "decreased" level of an indicator refer to the level of such indicator in the sample being reduced in comparison to the reference or reference sample. The terms "elevated" or "increased" level of an indicator refer to the level of such indicator in the sample being higher in comparison to the reference or reference sample.

Diabetes mellitus (DM) is a serious chronic disease characterized by an elevated blood sugar. Symptoms of a high blood sugar include but are not limited to frequent urination, increased thirst and increased hunger. If left untreated diabetes can cause both acute and long-term complications. Acute complications include but are not limited to diabetic ketoacidosis and non-ketotic hyperosmolar states. Long-term consequences include but are not limited to heart attacks, strokes, peripheral vascular disease, TIA's, renal insufficiency, renal failure, chronic neuropathic pain, foot ulceration, amputations, blindness, retinal damage, cataracts, fractures, cognitive decline, non-alcoholic steatohepatitis, cirrhosis and a variety of cancers. Diabetes occurs because the pancreas is unable to make sufficient insulin to keep glucose levels normal in both the fasting and the fed state and many people with diabetes also have cells that are not responding properly to the insulin that is produced. Diabetes can be classified into the following general categories: 1. Type 1 diabetes; 2. Type 2 diabetes; 3. Gestational diabetes mellitus (GDM); and 4. Specific types of diabetes due to other causes.

Type 1 diabetes mellitus results from the pancreas's failure to produce enough insulin. This form was previously referred to as "insulin-dependent diabetes mellitus" (IDDM) or "juvenile diabetes". Type 1 diabetes mellitus is characterized by loss of the insulin-producing beta cells of the islets of Langerhans in the pancreas, leading to insulin deficiency. This type can be further classified as immune-mediated or idiopathic. The majority of type 1 diabetes is of the immune-mediated nature, in which a T-cell-mediated autoimmune attack leads to the loss of beta cells and thus insulin.

Type 2 diabetes occurs when the pancreas is not able to make enough insulin to overcome resistance to the action of insulin. This form was previously referred to as "non insulin-dependent diabetes mellitus" (NIDDM) or "adult-onset diabetes". The primary cause is excessive body weight and not enough exercise. Type 2 diabetes mellitus is characterized by insulin resistance, which may be combined with relatively reduced insulin secretion. The defective responsiveness of body tissues to insulin is believed to involve the insulin receptor. However, the specific defects are not known. Type 2 diabetes mellitus is the most common type of diabetes mellitus. In the early stage of type 2, the predominant abnormality is reduced insulin sensitivity. At this stage, high blood sugar can be reversed by a variety of measures and medications that improve insulin sensitivity or reduce the liver's glucose production.

Gestational diabetes is the third main form and occurs when pregnant women without a previous history of diabetes develop a high blood-sugar level. Gestational diabetes mellitus (GDM) resembles type 2 diabetes mellitus in several respects, involving a combination of relatively inadequate insulin secretion and responsiveness. It occurs in about 2-10% of all pregnancies and may improve or disappear after delivery. However, after pregnancy approximately 5-10% of women with gestational diabetes are found to have diabetes mellitus, most commonly type 2. Gestational diabetes is fully treatable, but requires careful medical supervision throughout the pregnancy.

Other types of diabetes include but are not limited to monogenic diabetes syndromes (such as neonatal diabetes and maturity-onset diabetes of the young [MODY]), diseases of the exocrine pancreas (such as cystic fibrosis), and drug- or chemical-induced diabetes (such as in the treatment of HIV/AIDS or after organ transplantation).

Prediabetes indicates a condition that occurs when a person's blood glucose levels are higher than normal but not high enough for a diagnosis of type 2 diabetes. Many people destined to develop type 2 diabetes mellitus spend many years in a state of prediabetes.

Besides the administration of insulin, several other diabetes treatments are known including but not limited to the administration of metformin, sulfonylureas, dopamine agonist, DPP-4 inhibitors, glucagon-like peptides, meglitinides, amylinomimetic, alpha-glucosidase inhibitors, SGLT2 inhibitors, and/or thiazolidinediones.

Low-density lipoprotein (LDL) and high-density lipoprotein (HDL) belong to the group of lipoproteins. Lipoproteins transfer fats around the body in the extracellular fluid, can be sampled from blood and allow fats to be taken up by the cells of the body by receptor-mediated endocytosis. Lipoproteins are complex particles composed of multiple proteins which transport all fat molecules (lipids) around the body within the water outside cells. They are typically composed of 80-100 proteins/particle (organized by a single apolipoprotein B for LDL and the larger particles). The fats carried include cholesterol, phospholipids, and triglycerides; amounts of each vary considerably. LDL particles pose a risk for cardiovascular disease when they invade the endothelium and become oxidized, since the oxidized forms are more easily retained by the proteoglycans. A complex set of biochemical reactions regulates the oxidation of LDL particles, chiefly stimulated by presence of necrotic cell debris and free radicals in the endothelium. Increasing concentrations of LDL particles are strongly associated with increasing rates of accumulation of atherosclerosis within the walls of arteries over time, eventually resulting in sudden plaque ruptures and triggering clots within the artery opening, or a narrowing or closing of the opening, i.e. cardiovascular disease, stroke, and other vascular disease complications. LDL particles are sometimes referred to as bad cholesterol because they can transport their content of fat molecules into artery walls, attract macrophages, and thus drive atherosclerosis. In contrast, HDL particles are often called good cholesterol or healthy cholesterol because they can remove fat molecules from macrophages in the wall of arteries.

Serum creatinine (a blood measurement) is an important indicator of renal health because it is an easily measured byproduct of muscle metabolism that is excreted unchanged by the kidneys. Creatinine itself is produced via a biological system involving creatine, phosphocreatine (also known as creatine phosphate), and adenosine triphosphate (ATP, the body's immediate energy supply). Creatine is synthesized primarily in the liver from the methylation of glycocyamine (guanidino acetate, synthesized in the kidney from the amino acids arginine and glycine) by S-adenosyl methionine. It is then transported through blood to the other organs, muscle, and brain, where, through phosphorylation, it becomes the high-energy compound phosphocreatine. During the reaction, creatine and phosphocreatine are catalyzed by creatine kinase, and a spontaneous conversion to creatinine may occur. Creatinine is removed from the blood chiefly by the kidneys, primarily by glomerular filtration, but also by proximal tubular secretion. Little or no tubular reabsorption of creatinine occurs. If the filtration in the kidney is deficient, creatinine blood levels rise. Therefore, creatinine levels in blood and urine may be used to calculate the creatinine clearance (CrCl), which correlates with the glomerular filtration rate (GFR). Blood creatinine levels may also be used alone to calculate the estimated GFR (eGFR). The GFR is clinically important because it is a measurement of renal function. An alternate estimation of renal function can be made when interpreting the blood (plasma) concentration of creatinine along with that of urea. BUN-to-creatinine ratio (the ratio of blood urea nitrogen to creatinine) can indicate other problems besides those intrinsic to the kidney; for example, a urea level raised out of proportion to the creatinine may indicate a prerenal problem such as volume depletion.

As noted above diabetes is associated with a large variety of serious long-term consequences. These include ischemic heart disease and its sequelae, cerebrovascular disease, cerebral hemorrhage, peripheral vascular disease, polyneuropathy or mononeuropathy, painful neuropathy, renal insufficiency, albuminuria, renal failure, cataracts, reduced vision, blindness, retinopathy, foot ulceration, lower limb amputations, cognitive decline, dementia, falls, fractures, frailty, sexual dysfunction, erectile dysfunction, cancers, depression, sleep apnea, gut problems and others. Some of these consequences may in turn promote the progression of the severity of diabetes. Others such as NAFLD may be present before diabetes occurs and may contribute to its pathogenesis.

Albuminuria is a pathological condition wherein the protein albumin is present in the urine. It is a type of proteinuria. The kidneys normally do not filter large molecules into the urine, so albuminuria can be an indicator of damage to the kidneys or excessive salt intake. It can also occur in patients with long-standing diabetes, especially type 1 diabetes.

Polycystic ovary syndrome (PCOS), also called hyperandrogenic anovulation (HA) or Stein-Leventhal syndrome, refers to a set of symptoms due to a hormone imbalance in women. Signs and symptoms of PCOS include irregular or no menstrual periods, heavy periods, excess body and facial hair, acne, pelvic pain, trouble getting pregnant, and patches of thick, darker, velvety skin. Associated conditions include type 2 diabetes, obesity, obstructive sleep apnea, heart disease, mood disorders, and endometrial cancer. PCOS is due to a combination of genetic and environmental factors. Risk factors include obesity, not enough physical exercise, and a family history of someone with the condition. Diagnosis is based on two of the following three findings: no ovulation, high androgen levels, and ovarian cysts. PCOS has no cure. Treatment may involve lifestyle changes such as weight loss and exercise. Birth control pills may help with improving the regularity of periods, excess hair, and acne. Metformin and anti-androgens may also help.

Nonalkoholic fatty liver disease (NAFLD) is one of the causes of fatty liver, occurring when fat is deposited (steatosis) in the liver due to causes other than excessive alcohol use. NAFLD is the most common liver disorder in developed countries. NAFLD is related to insulin resistance and the metabolic syndrome and may respond to treatments originally developed for other insulin-resistant states (e.g. diabetes mellitus type 2) such as weight loss, metformin, and thiazolidinediones. Non-alcoholic steatohepatitis (NASH) is the most extreme form of NAFLD, and is regarded as a major cause of cirrhosis of the liver of unknown cause.

As used herein the term "hirsutism" refers to the excessive hairiness on women in those parts of the body where terminal hair does not normally occur or is minimal including but not limited to a beard or chest hair.

Amenorrhea refers to the absence of a menstrual period in a woman of reproductive age.

Infertility is the inability of a person, animal or plant to reproduce by natural means. It is usually not the natural state of a healthy adult, Obesity is a medical condition in which excess body fat has accumulated to the extent that it may have a negative effect on health, leading to reduced life expectancy and/or increased health problems. In Western countries, people are considered obese when their body mass index (BMI) is over 30 kg/m2, with the range 25-30 kg/m2 defined as overweight. Some East Asian countries use stricter criteria. Obesity increases the likelihood of various diseases, particularly heart disease, type 2 diabetes, obstructive sleep apnea, certain types of cancer, and osteoarthritis. Obesity is most commonly caused by a combination of excessive food energy intake, lack of physical activity, and genetic susceptibility, although a few cases are caused primarily by genes, endocrine disorders, medications, or psychiatric illness. Evidence to support the view that some obese people eat little yet gain weight due to a slow metabolism is limited Vitamin $B_{12}$ deficiency, also known as hypocobalaminemia, refers to low blood levels of vitamin $B_{12}$. A wide variety of signs and symptoms may occur including a decreased ability to think and changes in personality such as depression, irritability, and psychosis. Abnormal sensations, changes in reflexes, and poor muscle function can also occur as may inflammation of the tongue, decreased taste, low red blood cells, reduced heart function, and decreased fertility. In young children symptoms include poor growth, poor development, and difficulties with movement. Without early treatment some of the changes may be permanent. Common causes include poor absorption from the stomach or intestines, decreased intake, and increased requirements. Decreased absorption may be due to pernicious anemia, surgical removal of the stomach, chronic inflammation of the pancreas, intestinal parasites, certain medications, and some genetic disorders. Decreased intake may occur in those who eat a vegan diet or have malnutrition. Increased requirements occur in HIV/AIDS and in those with rapid red blood cell breakdown. Diagnosis is typically based on vitamin $B_{12}$ blood levels below 120-180 picomol/L (170-250 pg/mL) in adults. Elevated methylmalonic acid levels (values >0.4 micromol/L) may also indicated deficiency. A type of low red blood cells known as megaloblastic anemia is often but not always present. Supplementation is recommended to prevent deficiency in vegetarians who are pregnant. Once identified it is easily treated with supplementation by mouth or injection. There are no concerns from excess Vitamin $B_{12}$ among those who are otherwise healthy. Some cases may also be helped by treating the underlying cause. Other cases may require ongoing supplementation as the underlying cause is not curable. Vitamin $B_{12}$ deficiency is common. It is estimated to occur in about 6% of those under the age of 60 and 20% of those over the age of 60.

Cardiovascular disease (CVD) is a class of diseases that involve the heart or blood vessels. Cardiovascular disease include but are not limited to coronary artery diseases (CAD) such as angina and myocardial infarction (commonly known as a heart attack), stroke, hypertensive heart disease, rheumatic heart disease, cardiomyopathy, atrial fibrillation, congenital heart disease, endocarditis, aortic aneurysms, peripheral artery disease, and venous thrombosis.

One of the most common cardiovascular diseases is coronary artery disease (CAD), also known as ischemic heart disease (IHD), is a group of diseases including but not limited to stable angina, unstable angina, myocardial infarction, dyslipidemia, hypertension, and sudden coronary death. A common symptom is chest pain or discomfort which may travel into the shoulder, arm, back, neck, or jaw. Occasionally it may feel like heartburn. Usually symptoms occur with exercise or emotional stress, last less than a few minutes, and gets better with rest. Shortness of breath may also occur and sometimes no symptoms are present. The first sign is occasionally a heart attack. Other complications include heart failure or an irregular heartbeat. Risk factors include but are not limited to high blood pressure, smoking, diabetes, lack of exercise, obesity, high blood cholesterol, poor diet, and excessive alcohol, as well as depression. The underlying mechanism involves atherosclerosis of the arteries of the heart. A number of tests may help with diagnoses including but not limited to electrocardiogram, cardiac stress testing, coronary computed tomographic angiography, and coronary angiogram. In 2013 CAD was the most common cause of death globally, resulting in 8.14 million deaths (16.8%) up from 5.74 million deaths (12%) in 1990. The risk of death from CAD for a given age has decreased between 1980 and 2010 especially in the developed world. The number of cases of CAD for a given age has also decreased between 1990 and 2010. In the United States in 2010 about 20% of those over 65 had CAD, while it was present in 7% of those 45 to 64, and 1.3% of those 18 to 45. Rates are higher among men than women of a given age.

Myocardial infarction (MI) or acute myocardial infarction (AMI) occurs when blood flow stops to a part of the heart causing damage to the heart muscle. The most common symptom is chest pain or discomfort which may travel into the shoulder, arm, back, neck, or jaw. Often it is in the center or left side of the chest and lasts for more than a few minutes. The discomfort may occasionally feel like heartburn. Other symptoms may include shortness of breath, nausea, feeling faint, a cold sweat, or feeling tired. About 30% of people have atypical symptoms, with women more likely than men to present atypically. Among those over 75 years old, about 5% have had an MI with little or no history of symptoms. An MI may cause heart failure, an irregular heartbeat, or cardiac arrest. Most MIs occur due to coronary artery disease. Risk factors include but are not limited to high blood pressure, smoking, diabetes, lack of exercise, obesity, high blood cholesterol, poor diet, and excessive alcohol intake. The mechanism of an MI often involves the rupture of an atherosclerotic plaque, leading to complete blockage of a coronary artery. A number of tests are useful to help with diagnosis, including but not limited to electrocardiograms (ECGs), blood tests, and coronary angiography.

The terms "cancer" and "cancerous" refer to or describe the physiological condition in mammals that is typically characterized by unregulated cell proliferation. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including, e.g., gastrointestinal cancer), pancreatic cancer (including, e.g., metastatic pancreatic cancer), glioblastoma, cervical cancer, ovarian cancer, liver cancer, bladder cancer, hepatoma, breast cancer (including locally advanced, recurrent or metastatic HER-2 negative breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

Dementia, also known as senility, is a broad category of brain diseases that cause a long term and often gradual decrease in the ability to think and remember that is great enough to affect a person's daily functioning. Other common symptoms include emotional problems, problems with language, and a decrease in motivation. A person's consciousness is not affected. A dementia diagnosis requires a change from a person's usual mental functioning and a greater decline than one would expect due to aging. The most common type of dementia is Alzheimer's disease, which makes up 50% to 70% of cases. Other common types include vascular dementia (25%), Lewy body dementia (15%), and frontotemporal dementia. Less common causes include normal pressure hydrocephalus, Parkinson's disease, syphilis, and Creutzfeldt-Jakob disease among others. More than one type of dementia may exist in the same person.

The term "frailty" refers to a common geriatric syndrome that embodies an elevated risk of catastrophic declines in health and function among older adults. Frailty is a condition associated with ageing, which has been recognized for centuries.

The term "foot ulceration" refers to a major complication of diabetes mellitus, and probably the major component of the diabetic foot. Wound healing is an innate mechanism of action that works reliably most of the time. A key feature of wound healing is stepwise repair of lost extracellular matrix (ECM) that forms the largest component of the dermal skin layer. In diabetes mellitus the normal steps of the wound healing process are impeded. Many studies show a prolonged inflammatory phase in diabetic wounds, which causes a delay in the formation of mature granulation tissue and a parallel reduction in wound tensile strength.

The term "retinal disease" refers to any diseases and disorder of the retina and includes but is not limited to age-related macular degeneration, diabetic retinopathy, macular hole/pucker, retinoblastoma, retinal detachment, river blindness/onchocerciasis, and retinitis pigmentosa.

The terms "renal disease" and "kidney failure" refer to any diseases and disorder of the kidney and includes but is not limited to acute kidney failure and chronic kidney disease. Renal disease is mainly determined by a decrease in glomerular filtration rate, which is the rate at which blood is filtered in the glomeruli of the kidney. The condition is detected by a decrease in or absence of urine production or determination of waste products (creatinine or urea) in the blood. Depending on the cause, hematuria (blood loss in the urine) and proteinuria (protein loss in the urine) may be noted. There may be problems with increased fluid in the body (leading to swelling), increased acid levels, raised levels of potassium, decreased levels of calcium, increased levels of phosphate, and in later stages anemia. Bone health may also be affected. Long-term kidney problems are associated with an increased risk of cardiovascular disease.

Acute kidney injury (AKI), previously called acute renal failure (ARF), is a rapidly progressive loss of renal function, generally characterized by oliguria (decreased urine production, quantified as less than 400 mL per day in adults, less than 0.5 mL/kg/h in children or less than 1 mL/kg/h in infants); and fluid and electrolyte imbalance. AKI can result from a variety of causes, generally classified as prerenal, intrinsic, and postrenal. The underlying cause must be identified and treated to arrest the progress, and dialysis may be necessary to bridge the time gap required for treating these fundamental causes.

Chronic kidney disease (CKD), also known as chronic renal disease, is a progressive loss in kidney function over a period of months or years. The symptoms of worsening kidney function are not specific, and might include feeling generally unwell and experiencing a reduced appetite. Often, chronic kidney disease is diagnosed as a result of screening of people known to be at risk of kidney problems, such as those with high blood pressure or diabetes and those with a blood relative with CKD. This disease may also be identified when it leads to one of its recognized complications, such as cardiovascular disease, anemia, or pericarditis. It is differentiated from acute kidney disease in that the reduction in kidney function must be present for over 3 months. Chronic kidney disease is identified by a blood test for creatinine, which is a breakdown product of muscle metabolism. Higher levels of creatinine indicate a lower glomerular filtration rate and as a result a decreased capability of the kidneys to excrete waste products. Creatinine levels may be normal in the early stages of CKD, and the condition is discovered if urinalysis (testing of a urine sample) shows the kidney is allowing the loss of protein or red blood cells into the urine. To fully investigate the underlying cause of kidney damage, various forms of medical imaging, blood tests, and sometimes a kidney biopsy (removing a small sample of kidney tissue) are employed to find out if a reversible cause for the kidney malfunction is present.

Glycated hemoglobin (hemoglobin A1c, HbA1c, A1C, or Hb1c; sometimes also HbA1c or HGBA1C) is a form of hemoglobin that is measured primarily to identify the average plasma glucose concentration over prolonged periods. It is formed in a non-enzymatic glycation pathway by hemoglobin's exposure to plasma glucose. HbA1c is a measure of the beta-N-1-deoxy fructosyl component of hemoglobin. Normal levels of glucose produce a normal amount of glycated hemoglobin. As the average amount of plasma glucose increases, the fraction of glycated haemoglobin also increases predictablly. Thus, HbA1c may serve as a marker for average blood glucose levels over the previous months prior to the measurement as this is the lifespan of red blood cells. In diabetes mellitus, higher amounts of glycated hemoglobin, indicating poorer control of blood glucose levels, have been associated complications such as cardiovascular disease, nephropathy, and retinopathy. Monitoring HbA1c in type 1 diabetic patients may improve outcomes.

Using glucose test allow to determine the amount of glucose in the blood. These are mainly used in screening for prediabetes or diabetes. Patients are instructed not to consume anything but water during the fasting period. Caffeine will also distort the results. In people already having diabetes, blood glucose monitoring is used with frequent intervals in the management of the condition. There are several different kinds of glucose tests: Fasting blood sugar (FBS), fasting plasma glucose (FPG), wherein glucose level are measured 8 or 12 or 14 hours after eating.

The homeostatic model assessment (HOMA) is a method used to quantify insulin resistance and beta-cell function. It was first described under the name HOMA by Matthews et al. in 1985.

Glycated albumin (GA) is a ketoamine formed via a non-enzymatic glycation reaction of serum albumin and it reflects mean glycemia over two to three weeks. GA can be used for patients with anemia or hemoglobinopathies for whom the clinically measured hemoglobin A1c level may be inaccurate. As both serum and plasma samples can be used, GA can be analyzed from the same samples as common biological markers. GA is a useful marker for the screening of diabetes in a medical evaluation. It can be also used to determine the effectiveness of treatment before initiating or changing medications for diabetic patients.

Blood pressure (BP) is the pressure exerted by circulating blood upon the walls of blood vessels. When used without further specification, "blood pressure" usually refers to the arterial pressure in the systemic circulation. It is usually measured at a person's upper arm. Blood pressure is usually expressed in terms of the systolic (maximum) pressure over diastolic (minimum) pressure and is measured in millimeters of mercury (mm Hg). It is one of the vital signs along with respiratory rate, heart rate, oxygen saturation, and body temperature. Normal resting blood pressure in an adult is approximately 120/80 mm Hg.

The body mass index (BMI) or Quetelet index is a value derived from the mass (weight) and height of an individual. The BMI is defined as the body mass divided by the square of the body height, and is universally expressed in units of $kg/m^2$, resulting from mass in kilograms and height in metres. The BMI is an attempt to quantify the amount of tissue mass (muscle, fat, and bone) in an individual, and then categorize that person as underweight, normal weight, overweight, or obese based on that value. Commonly accepted BMI ranges are underweight: under 18.5; normal weight: 18.5 to 25; overweight: 25 to 30; obese: over 30.

As used herein, "treat", "treating" or "treatment" of a disease or injury means accomplishing one or more of the following: (a) reducing the severity of the disease or injury; (b) limiting or preventing development of symptoms characteristic of the disease or injury being treated; (c) inhibiting worsening of symptoms characteristic of the disease or injury being treated; (d) limiting or preventing recurrence of the disease or injury in an individual who has previously had the disease or injury; and (e) limiting or preventing recurrence of symptoms in individuals who were previously symptomatic for the disease or injury.

As used herein, "prevent", "preventing", "prevention", or "prophylaxis" of a disease or injury means preventing that such disease or injury occurs in patient.

The term "delay" or "delaying" a disease refers to a decrease in the progression of disease or disorder, i.e. delaying a disease refers to prolonging the time frame in which the symptoms or signs or cause of the disease worsen.

The terms "pharmaceutical", "pharmaceutical composition", "medicament" and "drug" are used interchangeably herein referring to a substance and/or a combination of substances being used for the identification, prevention or treatment of a disease or injury.

Biguanide is the organic compound with the formula $HN(C(NH)NH_2)_2$. A variety of derivatives of biguanide are used as pharmaceutical drugs including but not limited to metformin and its functional derivatives. Metformin is a biguanide hypoglycemic agent used e.g. in the treatment of non-insulin-dependent diabetes mellitus (diabetes mellitus type 2) in patients not responding to dietary modification.

The chemical structure of metformin is the following:

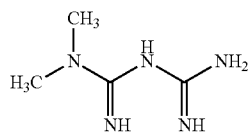

Metformin improves glycemic control by improving insulin sensitivity and decreasing intestinal absorption of glucose, as well as suppressing glucose production by the liver. It is the first-line drug of choice for the treatment of type 2 diabetes, in particular, in overweight and obese people and those with normal kidney function. Its use in gestational diabetes has been limited by safety concerns. It is also used in the treatment of polycystic ovary syndrome, and has been investigated for other diseases where insulin resistance may be an important factor such as nonalcoholic fatty liver disease and premature puberty. It helps reduce LDL cholesterol and triglyceride levels and is not associated with weight gain; in some people, it promotes weight loss. Metformin is one of only two oral antidiabetics in the World Health Organization Model List of Essential Medicines (the other being glibenclamide). Metformin causes few adverse effects when prescribed appropriately (the most common is gastrointestinal upset) and has been associated with a low risk of having a low blood sugar. Lactic acidosis (a buildup of lactate in the blood) can be a serious concern in overdose and when it is prescribed to people with contraindications, but otherwise, no significant risk exists. The term "metformin" also includes derivatives thereof.

Western blotting allows determining specific proteins (native or denatured) from extracts made from cells or tissues, before or after any purification steps. Proteins are generally separated by size using gel electrophoresis before being transferred to a synthetic membrane (typically nitrocellulose or PVDF) via dry, semi-dry, or wet blotting methods. The membrane can then be probed using antibodies using methods similar to immunohistochemistry, but without a need for fixation. Detection is typically performed using peroxidase linked antibodies to catalyze a chemiluminescent reaction. Western blotting is a routine molecular biology method that can be used to semi quantitatively or quantitatively compare protein levels between extracts. The size separation prior to blotting allows the protein molecular weight to be gauged as compared with known molecular weight markers. Western blotting is an analytical technique used to detect specific proteins in a given sample of tissue homogenate or extract. It uses gel electrophoresis to separate proteins by the length of the polypeptide (denaturing conditions) or by the 3-D structure of the protein (native/non-denaturing conditions).

The term "enzyme-linked immunosorbent assay" or "ELISA" refers to a diagnostic method for quantitatively or semi-quantitatively determining protein concentrations from blood plasma, serum or cell/tissue extracts in a multi-well plate format (usually 96-wells per plate). Broadly, proteins in solution are adsorbed to ELISA plates. Antibodies specific for the protein of interest are used to probe the plate. Background is minimized by optimizing blocking and washing methods (as for IHC), and specificity is ensured via the presence of positive and negative controls. Detection methods are usually colorimetric or chemiluminescence based.

Immunoprecipitation (IP) is the technique of precipitating a protein antigen out of solution using an antibody that specifically binds to that particular protein. This process can be used to isolate and concentrate a particular protein from a sample containing many thousands of different proteins. Immunoprecipitation requires that the antibody be coupled to a solid substrate at some point in the procedure.

A protein microarray (or protein chip) is a high-throughput method used to determine the presence and activities of proteins, and to analyse their function, in particular on a large scale. The chip consists of a support surface such as a glass slide, nitrocellulose membrane, bead, or microtitre plate, to which an array of capture proteins is bound. Probe molecules, typically labeled with a fluorescent dye, are added to the array. Any reaction between the probe and the immobilised protein emits a fluorescent signal that is read by a laser scanner. Protein microarrays are rapid, automated, economical, and highly sensitive, consuming small quantities of samples and reagents.

Antibody-based immunoassays such as a single plex immunoassay which quantifies one analyte per assay and n analytes would require n independent assays. In comparison to the ELISA for a single analyte, multiplex assays offer the possibility of obtaining more reliable quantitative information in a highly parallel analysis. These quantitative multiplex immunoassays couple the basic principle of antigen-antibody interactions to a wide variety of detection methods giving quantitative readouts.

Protein sequencing is a technique to determine the amino acid sequence of a protein, as well as which conformation the protein adopts and the extent to which it is complexed with any non-peptide molecules. The two major direct methods of protein sequencing are mass spectrometry and the Edman degradation reaction.

The term "mass spectrometry (MS)" refers to an analytical chemistry technique that allows to identify the amount and type of chemicals present in a sample by measuring the mass-to-charge ratio and abundance of gas-phase ions. The mass spectrum (plural spectra) is a plot of the ion signal as a function of the mass-to-charge ratio. The spectra are used to determine the elemental or isotopic signature of a sample, the masses of particles and of molecules, and to elucidate the chemical structures of molecules, such as peptides and other chemical compounds. Mass spectrometry works by ionizing chemical compounds to generate charged molecules or molecule fragments and measuring their mass-to-charge ratios. In a typical MS procedure, a sample, which may be solid, liquid, or gas, is ionized, for example by bombarding it with electrons. This may cause some of the sample's molecules to break into charged fragments. These ions are then separated according to their mass-to-charge ratio, typically by accelerating them and subjecting them to an electric or magnetic field: ions of the same mass-to-charge ratio will undergo the same amount of deflection. The ions are detected by a mechanism capable of detecting charged particles, such as an electron multiplier. Results are displayed as spectra of the relative abundance of detected ions as a function of the mass-to-charge ratio. The atoms or molecules in the sample can be identified by correlating known masses to the identified masses or through a characteristic fragmentation pattern.

The term "chromatography" refers to a mass transfer process involving adsorption. High-performance liquid chromatography (HPLC) relies on pumps to pass a pressurized liquid and a sample mixture through a column filled with a sorbent, leading to the separation of the sample components. The active component of the column, the sorbent, is typically a granular material made of solid particles (e.g. silica, polymers, etc.), 2-50 micrometers in size. The components of the sample mixture are separated from each other due to their different degrees of interaction with the sorbent particles. The pressurized liquid is typically a mixture of solvents (e.g. water, acetonitrile and/or methanol) and is referred to as a "mobile phase". Its composition and temperature play a major role in the separation process by influencing the interactions taking place between sample components and sorbent. These interactions are physical in nature, such as hydrophobic (dispersive), dipole-dipole and ionic, most often a combination. HPLC is distinguished from traditional ("low pressure") liquid chromatography because operational pressures are significantly higher (50-350 bar), while ordinary liquid chromatography typically relies on the force of gravity to pass the mobile phase through the column. Due to the small sample amount separated in analytical HPLC, typical column dimensions are 2.1-4.6 mm diameter, and 30-250 mm length. Also HPLC columns are made with smaller sorbent particles (2-50 micrometer in average particle size). This gives HPLC superior resolving power (the ability to distinguish between compounds) when separating mixtures, which makes it a popular chromatographic technique.

As used herein, "administering" includes in vivo administration, as well as administration directly to tissue ex vivo, such as vein grafts.

An "effective amount" is an amount of an agent sufficient to achieve the intended purpose. The effective amount of a given agent may vary due to factors such as the nature of the agent, the route of administration, the size and species of the subject to receive the agent, and the purpose of the administration. The effective amount in each individual case may be determined empirically by a skilled artisan according to established methods in the art.

The term "therapeutically effective amount" is an amount of a therapeutic agent sufficient to achieve the intended preventive or therapeutic effect, i.e. the amount of said therapeutic agent which is considered to achieve a bettering of the signs of symptoms of the disorder or disease to be treated, or to prevent the onset of the signs of symptoms of a disorder or disease to be prevented. The effective amount of a given therapeutic agent may vary due to factors such as the nature of the agent, the route of administration, the size and species of the animal to receive the therapeutic agent, and the purpose of the administration. The therapeutically effective amount in each individual case may be determined empirically by a skilled artisan according to established methods in the art.

"Pharmaceutically acceptable" means approved by a regulatory agency of the Federal or a state government or listed in the U.S. Pharmacopeia or other generally recognized pharmacopeia for use in animals, and more particularly in humans.

The term "active ingredient" refers to the substance in a pharmaceutical composition or formulation that is biologically active, i.e. that provides pharmaceutical value. A pharmaceutical composition may comprise one or more active ingredients which may act in conjunction with or independently of each other. The active ingredient can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as but not limited to those derived from sodium, potassium, ammonium, calcium, ferric hydroxides, isopropylamine, triethylamine, 2-ethylamino ethanol, histidine, procaine, and the like.

The terms "preparation" and "composition" are intended to include the formulation of the active compound with encapsulating material as a carrier providing a capsule in which the active component with or without other carriers, is surrounded by a carrier, which is thus in association with it.

The term "carrier", as used herein, refers to a pharmacologically inactive substance such as but not limited to a diluent, excipient, or vehicle with which the therapeutically active ingredient is administered. Such pharmaceutical carriers can be liquid or solid. Liquid carrier include but are not limited to sterile liquids, such as saline solutions in water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. A saline solution is a preferred carrier when the pharmaceutical composition is administered intravenously. Examples of suitable pharmaceutical carriers are described in "Remington's Pharmaceutical Sciences" by E. W. Martin.

Suitable pharmaceutical "excipients" include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The term "adjuvant" refers to agents that augment, stimulate, activate, potentiate, or modulate the therapeutic effect of the active ingredient. Examples of such adjuvants include but are not limited to inorganic adjuvants (e.g. inorganic metal salts such as aluminium phosphate or aluminium hydroxide), organic adjuvants (e.g. saponins or squalene), oil-based adjuvants (e.g. Freund's complete adjuvant and Freund's incomplete adjuvant), cytokines (e.g. IL-1β, IL-2, IL-7, IL-12, IL-18, GM-CFS, and INF-γ) particulate adjuvants (e.g. immuno-stimulatory complexes (ISCOMS), liposomes, or biodegradable microspheres), virosomes, bacterial adjuvants (e.g. monophosphoryl lipid A, or muramyl peptides), synthetic adjuvants (e.g. non-ionic block copolymers, muramyl peptide analogues, or synthetic lipid A), or synthetic polynucleotides adjuvants (e.g polyarginine or polylysine).

As used herein, a "patient" means any mammal, reptile or bird that may benefit from the present invention. Preferably, a patient is selected from the group consisting of laboratory animals (e.g. mouse, rat or rabbit), domestic animals (including e.g. guinea pig, rabbit, horse, donkey, cow, sheep, goat, pig, chicken, duck, camel, cat, dog, turtle, tortoise, snake, or lizard), or primates including chimpanzees, bonobos, gorillas and human beings. It is particularly preferred that the "patient" is a human being.

Embodiments

To identify candidate biomarkers allowing to evaluate or predict the effects of metformin, a large panel of 237 biochemical markers was screened. These were assayed in baseline serum samples collected in 8,401 participants (approximately 25% of whom were on various doses of metformin), and by exploring key findings using tissue and animal models. GDF15 levels was identified as a suitable biomarker indicating the response to metformin's use in people with dysglycemia and additional cardiovascular risk factors. Furthermore, it was found that the concentration of GDF15 closely reflects metformin's dose.

In a first aspect, the present invention relates to metformin for use in treating a patient, wherein the patient exhibits an increased level of GDF15 or a functional variant thereof, in response to metformin treatment.

In embodiments, said patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease, or reduced longevity.

In particular embodiments, the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, and hypertension.

In further embodiments, the patient is at risk of developing or suffers from a disease or disorder selected from the group consisting of cancer, cognitive decline, dementia, frailty, falls, unsteadiness, erectile dysfunction, sexual dysfunction, chronic pain, foot ulceration, retinal disease, decreased vision, renal disease or reduced longevity.

In particular embodiments, the disease or disorder is diabetes. In particular, the disease or disorder is diabetes Type I, diabetes Type II, or gestational diabetes.

In particular embodiments, GDF15 comprises an amino acid sequence as given in SEQ ID NO: 1. In embodiments, the functional variant exhibits the same functional properties as native GDF15. In particular, the functional variant exhibits at least 80% sequence identity to GDF15 according to SEQ ID NO: 1. In particular, the functional variant exhibits at least 85%, 90%, 95%, 97% or 99% sequence identity to GDF15 according to SEQ ID NO: 1. In particular embodiments, the functional variant exhibits 80%, 90%, or 99% sequence identity to GDF15 according to SEQ ID NO: 1.

In particular embodiments, the level of GDF15 is increased by at least 25%, i.e. the level of GDF15 or a variant thereof, is increased by 25, 30, 35, 40, 45, 50, 55, 60, 65, 70, 75, 80, 85, 90, 95, 100, 110, 120, 130, 140, 150, 160, 170, 180, 190, or 200%. In particular embodiments, the level of GDF15 is increased by at least 50%, in particular by at least 75% or at least 100%. In particular embodiments, the level of GDF15 is increased by 25% to 200%, in particular by 30% to 150%, in particular by 50 to 100%.

In embodiments, the patient exhibits an increased expression level of GDF15 or a functional variant thereof.

In particular embodiments, the level of GDF15 is increased in comparison to a reference. The reference may be the GDF15 level measured in a reference sample of the patient before metformin administration, in particular in a reference sample of the patient taken at a time point prior to Metformin administration. The reference may be a representative reference value, in particular a reference value which is representative of the level of GDF-15 in a subject who has not obtained metformin administration. The reference value may be adjusted for factors associated with the propensity to prescribe metformin. In particular these factors are selected from the group consisting of age, sex, weight, prior cardiovascular event, a prior diagnosis of diabetes, serum creatinine, HbA1c, and fasting plasma glucose.

In particular embodiments, the patient is an individual who may benefit from the present invention. In particular, a patient is selected from the group consisting of mammal, reptile or bird that. In particular embodiments the patient is selected from the group consisting of laboratory animals (e.g. mouse, rat or rabbit), domestic animals (including e.g. guinea pig, rabbit, horse, donkey, cow, sheep, goat, pig, chicken, duck, camel, cat, dog, turtle, tortoise, snake, or lizard), or primates including chimpanzees, bonobos, gorillas and human beings. In particular, the patient is a human being.

In a second aspect, the present invention provides a method of identifying a patient or a group of patients who will benefit from metformin treatment, comprising the steps of (i) administering an effective amount of metformin to a patient, (ii) determining the level of GDF15 or a functional variant thereof, in a patient's sample, and (iii) comparing the GDF15 level determined in step (ii) to that of a reference, wherein an increased level of GDF15 is indicative of a response of the patient to metformin administration.

In particular embodiments, the effective amount of metformin administered in step (i) is sufficient to achieve the intended purpose, i.e. is sufficient to induce a response in a subject responding to metformin treatment. Accordingly, the effective amount of metformin administered in step (i) is an amount that induces a response to metformin treatment in a subject responding to metformin. In particular embodiments, metformin is administered in step (i) in an amount of 500-2000 mg, in particular in an amount of 500, 550, 600, 650, 700, 750, 800, 850, 900, 950, 1000, 1100, 1200, 1300, 1400, 1500, 1600, 1700, 1800, 1900, or 2000 mg. It is well-known to the person skilled in the art how to determine the amount of metformin sufficient to induce a response to metformin treatment in an individual responding to metformin.

In particular embodiments, GDF15 determined in step (ii) comprises an amino acid sequence as given in SEQ ID NO: 1. In embodiments, the functional variant exhibits the same functional properties as native GDF15. In particular, the functional variant exhibits at least 80% sequence identity to GDF15 according to SEQ ID NO: 1. In particular, the functional variant exhibits at least 85%, 90%, 95%, 97% or 99% sequence identity to GDF15 according to SEQ ID NO: 1. In particular embodiments, the functional variant exhibits 80%, 90%, or 99% sequence identity to GDF15 according to SEQ ID NO: 1.

In particular embodiments, the level of GDF15 or the functional variant thereof, is determined in step (ii) via any method well-known in the art. In particular, the level of GDF15 or the functional variant thereof, is determined in step (ii) via a method selected from the group consisting of ELISA, Western Blot, immunoprecipitation, HPLC, microarrays, mass spectroscopy, and sequencing. In particular embodiments, the level of GDF15 is determined using an immuno-detection assay, in particular via ELISA.

In particular embodiments, the level of GDF15 or the functional variant thereof, is determined in step (ii) directly or indirectly using a GDF15-binding molecule. In particular, the level of GDF15 is determined using an antibody specific for GDF15. In particular, the level of GDF15 is determined using a monoclonal antibody specific for GDF15. In particular, the antibody competes with an antibody which recognizes a peptide comprising amino acids 197-308 of GDF-15 according to SEQ ID NO: 1. In particular, the antibody recognizes an antigen comprising amino acids 197-308 of GDF-15 according to SEQ ID NO: 1.

In particular embodiments, the level of GDF15 or the functional variant thereof, in a patients sample is determined within hours after metformin administration. In particular, the level of GDF15 or a functional variant thereof, is determined within 1, 2, 3, 4, 5, 6, 7, 8, 9, 10, 11, 12, 13, 14, 15, 16, 17, 18, 19, 20, 21, 22, 23, or 24 hours after metformin administration. In particular, the level of GDF15 or a functional variant thereof, is determined within 12 hours after metformin administration, in particular within 6 hours after metformin administration. In particular, the level of GDF15 or a functional variant thereof, is determined within 1 to 12 hours, 2 to 10 hours, or 4 to 8 hours after metformin administration.

In particular embodiments, the level of GDF15 or the functional variant thereof, in a patient's sample is determined within days after metformin administration. In particular, the level of GDF15 or a functional variant thereof, is determined within 1, 2, 3, 4, 5, 6, or 7 days after metformin administration. In particular, the level of GDF15 or a functional variant thereof, is determined within 1 to 7 days, in particular within 1 to 5 days, in particular within 1 to 2 days after metformin administration.

In particular embodiments, the patient's sample is selected from the group consisting of bodily fluid and tissue sample. In particular, the body liquid sample is selected from the group consisting of whole blood, serum, plasma, sputum, saliva, and urine.

In particular embodiments, the level of GDF15 or the functional variant thereof, in particular the expression level, is increased by at least 25%, i.e. the level of GDF15 or a variant thereof, is increased by 25, 30, 35, 40, 45, 50, 55, 60, 65, 70, 75, 80, 85, 90, 95, 100, 110, 120, 130, 140, 150, 160, 170, 180, 190, or 200%. In particular embodiments, the level of GDF15 is increased by at least 50%, in particular by at least 75% or at least 100%. In particular embodiments, the level of GDF15 or a functional variant thereof, is increased by 25% to 200%, in particular by 30% to 150%, in particular by 50 to 100%.

In particular embodiments, the level of GDF15 or a functional variant thereof, is increased in comparison to a reference. The reference may be the level of GDF15 or a functional variant thereof, measured in a reference sample of the patient taken before metformin administration. In particular in a reference sample of the patient taken at a time point prior to metformin administration. The reference may be a representative reference value, in particular a reference value which is representative of the level of GDF-15 or a functional variant thereof, in a subject who has not obtained metformin administration. The reference value may be adjusted for factors associated with the propensity to prescribe metformin. In particular these factors are selected from the group consisting of age, sex, weight, prior cardiovascular event, a prior diagnosis of diabetes, serum creatinine, HbA1c, and fasting plasma glucose.

In further embodiments, one or more factors are determined in addition to GDF-15 in an optional step (iv). In particular, the additional one or more factors are selected from the list consisting of:
(a) Fasting glucose levels,
(b) Post-prandial glucose levels
(c) Fructosamine levels
(d) Glycated albumin In particular embodiments, one or more of the factors selected from the list consisting of
(a) HbA1c
(b) Random glucose levels
(c) Fasting insulin levels
(d) Hemeostatic model assessment of insulin resistance (HOMAIR)
(e) Other measures of insulin resistance
(f) Lipid levels, in particular selected from the group consisting of HDL, LDL, total cholesterol, triglycerides, apolipoprotein B,
(g) Albuminuria, in particular microalbuminuria or macroalbuminuria
(h) Creatinine or estimated GFR,
(i) ALT level
(j) Vitamin $B_{12}$ level
(k) Cotinine level
(l) Telomere length
(m) one or more of the biomarker selected from the group consisting of NT-proBNP, Trefoil Factor 3, Apolipoprotein B, Angiopoietin-2, Osteoprotegerin, Alpha-2-Macroglobulin, Hepatocyte Growth Factor Receptor, Glutathione S Transferase alpha, Chromogranin A, IGF Binding Protein 4, Tenascin-C, Selenoprotein P, Macrophage Derived Chemokine, YKL-40, IGF Binding Protein 2
(n) one or more of the factors selected from the group consisting of blood pressure, weight, BMI, waist to hip ratio, waist circumference, diabetes duration, smoking status, imaging evidence of fatty liver, troponin levels, LV dysfunction, cardiovascular risk, other diabetes complications, retinal imaging, and nerve conduction studies, may be detected in an optional step (v), in particular in order to confirm results obtained by the method of steps (i) to (iii) or (i) to (iv).

In particular embodiments, the patient is an individual who may benefit from the present invention. In particular, a patient is selected from the group consisting of mammal, reptile or bird that. In particular embodiments the patient is selected from the group consisting of laboratory animals (e.g. mouse, rat or rabbit), domestic animals (including e.g. guinea pig, rabbit, horse, donkey, cow, sheep, goat, pig, chicken, duck, camel, cat, dog, turtle, tortoise, snake, or lizard), or primates including chimpanzees, bonobos, gorillas and human beings. In particular, the patient is a human being.

In particular embodiments, the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, and hypertension.

In particular embodiments, the patient is at risk of developing or suffers from a disease or disorder selected from the group consisting of cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, the disease or disorder is diabetes. In particular, the disease or disorder is diabetes Type I, diabetes Type II, or gestational diabetes.

In a third aspect, the present invention provides a pharmaceutical composition comprising metformin and at least one pharmaceutically acceptable carrier, adjuvant and/or excipient for use in treating a disease or disorder, wherein the patient exhibits an increased level of GDF15 or a functional variant thereof, in response to metformin treatment.

In embodiments, the disease or disorder is selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease, or reduced longevity In particular embodiments, the disease or disorder is selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, and hypertension.

In further embodiments, the disease or disorder is selected from the group consisting of cancer, cognitive decline, dementia, frailty, falls, unsteadiness, erectile dysfunction, sexual dysfunction, chronic pain, foot ulceration, retinal disease, decreased vision, renal disease or reduced longevity.

In particular embodiments, the disease or disorder is diabetes. In particular embodiments, the disease or disorder is diabetes Type I, diabetes Type II, or gestational diabetes.

In particular embodiments, the level of GDF15 or the functional variant thereof, in particular the expression level, is increased by at least 25%, i.e. the level of GDF15 or a variant thereof, is increased by 25, 30, 35, 40, 45, 50, 55, 60, 65, 70, 75, 80, 85, 90, 95, 100, 110, 120, 130, 140, 150, 160, 170, 180, 190, or 200%. In particular embodiments, the level of GDF15 is increased by at least 50%, in particular by at least 75% or at least 100%. In particular embodiments, the level of GDF15 or a functional variant thereof, is increased by 25% to 200%, in particular by 30% to 150%, in particular by 50 to 100%.

In particular embodiments, GDF15 comprises an amino acid sequence as given in SEQ ID NO: 1. In embodiments, the functional variant exhibits the same functional properties as native GDF15. In particular, the functional variant exhibits at least 80% sequence identity to GDF15 according to SEQ ID NO: 1. In particular, the functional variant exhibits at least 85%, 90%, 95%, 97% or 99% sequence identity to GDF15 according to SEQ ID NO: 1. In particular embodiments, the functional variant exhibits 80%, 90%, or 99% sequence identity to GDF15 according to SEQ ID NO: 1.

In particular embodiments, the patient is an individual who may benefit from the present invention. In particular, a patient is selected from the group consisting of mammal, reptile or bird that. In particular embodiments the patient is selected from the group consisting of laboratory animals (e.g. mouse, rat or rabbit), domestic animals (including e.g. guinea pig, rabbit, horse, donkey, cow, sheep, goat, pig, chicken, duck, camel, cat, dog, turtle, tortoise, snake, or lizard), or primates including chimpanzees, bonobos, gorillas and human beings. In particular, the patient is a human being.

In particular embodiments, the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, and hypertension.

In particular embodiments, the patient is at risk of developing or suffers from a disease or disorder selected from the group consisting of cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, the disease or disorder is diabetes. In particular, the disease or disorder is diabetes Type I, diabetes Type II, or gestational diabetes.

In a fourth aspect, the present invention provides a method of adapting the dosage of metformin comprising
(i) administering metformin to a patient,
(ii) determining the level of GDF15 in a patient's sample
(iii) comparing the GDF15 level determined in step (ii) to a reference, and
(iv) adjusting the dosage of metformin in that the treatment with metformin is stopped in case the level of GDF15 is not increased, and the dosage of metformin is maintained or increased in case the level of GDF15 is increased.

In particular embodiments, metformin is administered in step (i) in an amount sufficient to achieve the intended purpose, i.e. is sufficient to induce a response in a subject responding to metformin treatment. Accordingly, the effective amount of metformin administered in step (i) is an amount that induces a response to metformin treatment in a subject responding to metformin. In particular embodiments, metformin is administered in step (i) in an amount of 500-2000 mg, in particular in an amount of 500, 550, 600, 650, 700, 750, 800, 850, 900, 950, 1000, 1100, 1200, 1300, 1400, 1500, 1600, 1700, 1800, 1900, or 2000 mg. It is well-known to the person skilled in the art how to determine the amount of metformin sufficient to induce a response to metformin treatment in an individual responding to metformin.

In particular embodiments, the level of GDF15 or the functional variant thereof, in particular the expression level of GDF15 or the functional variant thereof, determined in step (ii) is increased by at least 25%, i.e. the level of GDF15 or a variant thereof, is increased by 25, 30, 35, 40, 45, 50, 55, 60, 65, 70, 75, 80, 85, 90, 95, 100, 110, 120, 130, 140, 150, 160, 170, 180, 190, or 200%. In particular embodiments, the level of GDF15 is increased by at least 50%, in particular by at least 75% or at least 100%. In particular embodiments, the level of GDF15 or a functional variant thereof, is increased by 25% to 200%, in particular by 30% to 150%, in particular by 50 to 100%.

In particular embodiments, GDF15 determined in step (ii) comprises an amino acid sequence as given in SEQ ID NO: 1. In embodiments, the functional variant exhibits the same functional properties as native GDF15. In particular, the functional variant exhibits at least 80% sequence identity to GDF15 according to SEQ ID NO: 1. In particular, the functional variant exhibits at least 85%, 90%, 95%, 97% or 99% sequence identity to GDF15 according to SEQ ID NO: 1. In particular embodiments, the functional variant exhibits 80%, 90%, or 99% sequence identity to GDF15 according to SEQ ID NO: 1.

In particular embodiments, the level of GDF15 or the functional variant thereof, is determined in step (ii) via any method well-known in the art. In particular, the level of GDF15 or the functional variant thereof, is determined in step (ii) via a method selected from the group consisting of ELISA, Western Blot, immunoprecipitation, HPLC, microarrays, mass spectroscopy, and sequencing. In particular embodiments, the level of GDF15 is determined using an immuno-detection assay.

In particular embodiments, the level of GDF15 or the functional variant thereof, is determined in step (ii) directly or indirectly using a GDF15-binding molecule. In particular, the level of GDF15 is determined using an antibody specific for GDF15. In particular, the level of GDF15 is determined using a monoclonal antibody specific for GDF15. In embodiments, the antibody competes with an antibody which recognizes a peptide comprising amino acids 197-308 of GDF-15. In particular, the antibody competes with an antibody which recognizes a peptide comprising amino acids 197-308 of GDF-15 according to SEQ ID NO: 1. In particular, the antibody recognizes a peptide comprising amino acids 197-308 of GDF-15 according to SEQ ID NO: 1.

In particular embodiments, the level of GDF15 or the functional variant thereof, in a patients sample is determined in step (ii) within hours after metformin administration. In particular, the level of GDF15 or a functional variant thereof, is determined within 1, 2, 3, 4, 5, 6, 7, 8, 9, 10, 11, 12, 13, 14, 15, 16, 17, 18, 19, 20, 21, 22, 23, or 24 hours after metformin administration. In particular, the level of GDF15 or a functional variant thereof, is determined within 12 hours after metformin administration, in particular within 6 hours after metformin administration. In particular, the level of GDF15 or a functional variant thereof, is determined within 1 to 12 hours, 2 to 10 hours, or 4 to 8 hours after metformin administration.

In particular embodiments, the level of GDF15 or the functional variant thereof, in a patient's sample is determined in step (ii) within days after metformin administration. In particular, the level of GDF15 or a functional variant thereof, is determined within 1, 2, 3, 4, 5, 6, or 7 days after metformin administration. In particular, the level of GDF15 or a functional variant thereof, is determined within 1 to 7 days, in particular within 1 to 5 days, in particular within 1 to 2 days after metformin administration.

In particular embodiments, the patient's sample is selected from the group consisting of bodily fluid and tissue sample. In particular, the body liquid sample is selected from the group consisting of whole blood, serum, plasma, sputum, saliva, and urine.

In particular embodiments, the level of GDF15 or a functional variant thereof, is increased in comparison to a reference. The reference may be the level of GDF15 or a functional variant thereof, measured in a reference sample of the patient taken before metformin administration. In particular in a reference sample of the patient taken at a time point prior to metformin administration. The reference may be a representative reference value, in particular a reference value which is representative of the level of GDF-15 or a functional variant thereof, in a subject who has not obtained metformin administration. The reference value may be adjusted for factors associated with the propensity to prescribe metformin. In particular these factors are selected from the group consisting of age, sex, weight, prior cardiovascular event, a prior diagnosis of diabetes, serum creatinine, HbA1c, and fasting plasma glucose.

In embodiments, the dosage of metformin is increased in step (iv) by 10, 20, 30, 40, 50, 60, 70, 80, 90, 100, 150, or 200% in case the level of GDF15 is increased, in particular in response to the initial metformin administration.

In particular embodiments, the patient is an individual who may benefit from the present invention. In particular, a patient is selected from the group consisting of mammal, reptile or bird that. In particular embodiments the patient is selected from the group consisting of laboratory animals (e.g. mouse, rat or rabbit), domestic animals (including e.g. guinea pig, rabbit, horse, donkey, cow, sheep, goat, pig, chicken, duck, camel, cat, dog, turtle, tortoise, snake, or lizard), or primates including chimpanzees, bonobos, gorillas and human beings. In particular, the patient is a human being.

In particular embodiments, the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, and hypertension.

In particular embodiments, the patient is at risk of developing or suffers from a disease or disorder selected from the group consisting of cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, the disease or disorder is diabetes. In particular, the disease or disorder is diabetes Type I, diabetes Type II, or gestational diabetes.

In further embodiments, one or more factors are determined in addition to GDF-15 in an optional step (v). In particular, the additional one or more factors are selected from the list consisting of:
  (a) Fasting glucose levels,
  (b) Post-prandial glucose levels
  (c) Fructosamine levels
  (d) Glycated albumin In particular embodiments, one or more of the factors selected from the list consisting of
  (a) HbA1c
  (b) Random glucose levels
  (c) Fasting insulin levels
  (d) Hemeostatic model assessment of insulin resistance (HOMAIR)
  (e) Other measures of insulin resistance
  (f) Lipid levels, in particular selected from the group consisting of HDL, LDL, total cholesterol, triglycerides, apolipoprotein B,
  (g) Albuminuria, in particular microalbuminuria or macroalbuminuria
  (h) Creatinine or estimated GFR,
  (i) ALT level
  (j) Vitamin $B_{12}$ level
  (k) Cotinine level
  (l) Telomere length
  (m) one or more of the biomarker selected from the group consisting of NT-proBNP, Trefoil Factor 3, Apolipoprotein B, Angiopoietin-2, Osteoprotegerin, Alpha-2-Macroglobulin, Hepatocyte Growth Factor Receptor, Glutathione S Transferase alpha, Chromogranin A, IGF Binding Protein 4, Tenascin-C, Selenoprotein P, Macrophage Derived Chemokine, YKL-40, IGF Binding Protein 2
  (n) one or more of the factors selected from the group consisting of blood pressure, weight, BMI, waist to hip ratio, waist circumference, diabetes duration, smoking status, imaging evidence of fatty liver, troponin levels, LV dysfunction, cardiovascular risk, other diabetes complications, retinal imaging, and nerve conduction studies, may be detected in an optional step (vi), in particular in order to confirm results obtained by the method of steps (i) to (iii) or (v).

Any of these additional factors determined in optional step (v) or (vi) is determined subsequent to step (iii) and prior to step (iv).

In a fifth aspect, the present invention provides for the use of GDF15 or a functional variant thereof, as biomarker for identifying a patient who will benefit from metformin treatment.

In a sixth aspect, the present invention provides kit for use in identifying a patient who will benefit or who will not benefit from metformin treatment, comprising means for detecting the level of GDF15 or a functional variant thereof.

In particular embodiments, the means for detecting the level of GDF15 or the functional variant thereof, are suitable to detect the level of GDF15 or the functional variant thereof, via any method well-known in the art. In particular, the means for detecting the level of GDF15 or the functional variant thereof are suitable to detect GDF15 or the functional variant thereof, via a method selected from the group consisting of ELISA, Western Blot, immunoprecipitation, HPLC, microarrays, mass spectroscopy, and sequencing. In particular embodiments, the means for detecting the level of GDF15 or the functional variant thereof are suitable to detect GDF15 or the functional variant thereof, via an immuno-detection assay.

In particular embodiments, the means for detecting the expression level of GDF15 or the functional variant thereof, are suitable to directly or indirectly determine the level of GDF15 or the functional variant thereof. In particular embodiments, the means for detecting the level of GDF15 or the functional variant thereof comprise a GDF15-binding molecule. In particular, the means for detecting the level of GDF15 or the functional variant thereof comprise an antibody specific for GDF15. In particular, the means for detecting the level of GDF15 or the functional variant thereof comprise monoclonal antibody specific for GDF15. In particular, the antibody competes with an antibody which recognizes a peptide comprising amino acids 197-308 of GDF-15 according to SEQ ID NO: 1. In particular, the antibody recognizes a peptide comprising amino acids 197-308 of GDF-15 according to SEQ ID NO: 1.

In particular embodiments, the kit further comprises reagents required to perform the desired detection method.

In particular embodiments, the reagents may be selected from the group consisting of buffers, diluents, and solvents.

In particular embodiments, the kit further comprises one or more of the following
  (a) a container,
  (b) suitable control, and/or
  (c) a data carrier, wherein the data carrier comprises information such as
    (i) instructions concerning methods identifying a patient who has a high likelihood of responding to Metformin treatment
    (ii) instructions for use of the means for detecting GDF15 level,
    (iii) quality information such as information about the lot/batch number of the means for detecting GDF15 level and/or of the kit, the manufacturing or assembly site or the expiry or sell-by date, information concerning the correct storage or handling of the kit,
    (iv) information concerning the composition of the buffer(s), diluent(s), reagent(s) for detecting level of GDF15,
    (v) information concerning the interpretation of information obtained when performing the above-mentioned methods of identifying a patient who has a high likelihood of responding to Metformin treatment,
    (vi) a warning concerning possible misinterpretations or wrong results when applying unsuitable methods and/or unsuitable means, and/or
    (vii) a warning concerning possible misinterpretations or wrong results when using unsuitable reagent(s) and/or buffer(s).

In a seventh aspect, the present invention provides the use of the kit of the sixth aspect in a method of the second aspect. Accordingly, the kit disclosed above is for use in a method of identifying a patient who will benefit or who will not benefit from metformin treatment by detecting the level of GDF-15 in a sample from said patient.

In a eighth aspect, the present invention provides a method of treating a patient at risk of developing or suffering from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease and reduced longevity comprising the step of administering to said patient a therapeutically effective amount of metformin, wherein said patient exhibits an increased level of GDF15 or a functional variant thereof, in response to (an initial) metformin administration.

In particular embodiments, a method is provided for treating a patient at risk of developing or suffering from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, and hypertension.

In particular embodiments, a method is provided for treating a patient at risk of developing or suffering from a disease or disorder selected from the group consisting of cancer, cognitive decline, dementia, frailty, falls, unsteadiness, erectile dysfunction, sexual dysfunction, chronic pain, foot ulceration, retinal disease, decreased vision, renal disease and reduced longevity, comprising the step of administering to said patient a therapeutically effective amount of metformin, wherein said patient exhibits an increased level of GDF15 in response to (an initial) metformin treatment.

In particular embodiments, the level of GDF15 or the functional variant thereof, in particular the expression level of GDF15 or the functional variant thereof, is increased by at least 25%, i.e. the level of GDF15 or a variant thereof, is increased by 25, 30, 35, 40, 45, 50, 55, 60, 65, 70, 75, 80, 85, 90, 95, 100, 110, 120, 130, 140, 150, 160, 170, 180, 190, or 200%. In particular embodiments, the level of GDF15 is increased by at least 50%, in particular by at least 75% or at least 100%. In particular embodiments, the level of GDF15 or a functional variant thereof, is increased by 25% to 200%, in particular by 30% to 150%, in particular by 50 to 100%.

In particular embodiments, GDF15 comprises an amino acid sequence as given in SEQ ID NO: 1. In embodiments, the functional variant exhibits the same functional properties as native GDF15. In particular, the functional variant exhibits at least 80% sequence identity to GDF15 according to SEQ ID NO: 1. In particular, the functional variant exhibits at least 85%, 90%, 95%, 97% or 99% sequence identity to GDF15 according to SEQ ID NO: 1. In particular embodiments, the functional variant exhibits 80%, 90%, or 99% sequence identity to GDF15 according to SEQ ID NO: 1. The method of any of claims 25 to 28, wherein the level of GDF-15 is measured in a sample of the patient, in particular wherein the level of GDF-15 is measured in a sample of the patient prior to treatment.

In particular embodiments, prior to administering metformin treatment, the level of GDF-15 is (i) determined in a sample of the patient and is (ii) compared to a reference, in particular in accordance with a method of aspect 2 or 4 disclosed herein.

In particular embodiments, the level of GDF15 or the functional variant thereof, is determined via any method well-known in the art. In particular, the level of GDF15 or the functional variant thereof, is determined in step (ii) via a method selected from the group consisting of ELISA, Western Blot, immunoprecipitation, HPLC, microarrays, mass spectroscopy, and sequencing. In particular embodiments, the level of GDF15 is determined using an immunodetection assay.

In particular embodiments, the level of GDF15 or the functional variant thereof, is determined directly or indirectly using a GDF15-binding molecule. In particular, the level of GDF15 is determined using an antibody specific for GDF15. In particular, the level of GDF15 is determined using a monoclonal antibody specific for GDF15. In embodiments, the antibody competes with an antibody which recognizes a peptide comprising amino acids 197-308 of GDF-15. In particular, the antibody competes with an antibody which which recognizes a peptide comprising amino acids 197-308 of GDF-15 according to SEQ ID NO: 1. In particular, the antibody recognizes a peptide comprising amino acids 197-308 of GDF-15 according to SEQ ID NO: 1.

In particular embodiments, the level of GDF15 or the functional variant thereof, in a patients sample is determined within hours after metformin administration. In particular, the level of GDF15 or a functional variant thereof, is determined within 1, 2, 3, 4, 5, 6, 7, 8, 9, 10, 11, 12, 13, 14, 15, 16, 17, 18, 19, 20, 21, 22, 23, or 24 hours after metformin administration. In particular, the level of GDF15 or a functional variant thereof, is determined within 12 hours after metformin administration, in particular within 6 hours after metformin administration. In particular, the level of GDF15 or a functional variant thereof, is determined within 1 to 12 hours, 2 to 10 hours, or 4 to 8 hours after metformin administration.

In particular embodiments, the level of GDF15 or the functional variant thereof, in a patient's sample is determined within days after metformin administration. In particular, the level of GDF15 or a functional variant thereof, is determined within 1, 2, 3, 4, 5, 6, or 7 days after metformin administration. In particular, the level of GDF15 or a functional variant thereof, is determined within 1 to 7 days, in particular within 1 to 5 days, in particular within 1 to 2 days after metformin administration.

In particular embodiments, the patient's sample is selected from the group consisting of bodily fluid and tissue sample. In particular, the body liquid sample is selected from the group consisting of whole blood, serum, plasma, sputum, saliva, and urine.

In particular embodiments, the level of GDF15 or a functional variant thereof, is increased in comparison to a reference. The reference may be the level of GDF15 or a functional variant thereof, measured in a reference sample of the patient taken before metformin administration. In particular in a reference sample of the patient taken at a time point prior to metformin administration. The reference may be a representative reference value, in particular a reference value which is representative of the level of GDF-15 or a functional variant thereof, in a subject who has not obtained metformin administration. The reference value may be adjusted for factors associated with the propensity to prescribe metformin. In particular these factors are selected from the group consisting of age, sex, weight, prior cardiovascular event, a prior diagnosis of diabetes, serum creatinine, HbA1c, and fasting plasma glucose.

In further embodiments, one or more factors are determined in addition to GDF-15. In particular, the additional one or more factors are selected from the list consisting of:
(a) Fasting glucose levels,
(b) Post-prandial glucose levels
(c) Fructosamine levels
(d) Glycated albumin In particular embodiments, one or more of the factors selected from the list consisting of
(a) HbA1c
(b) Random glucose levels
(c) Fasting insulin levels
(d) Hemeostatic model assessment of insulin resistance (HOMAIR)
(e) Other measures of insulin resistance
(f) Lipid levels, in particular selected from the group consisting of HDL, LDL, total cholesterol, triglycerides, apolipoprotein B,
(g) Albuminuria, in particular microalbuminuria or macroalbuminuria
(h) Creatinine or estimated GFR,
(i) ALT level
(j) Vitamin $B_{12}$ level
(k) Cotinine level
(l) Telomere length
(m) one or more of the biomarker selected from the group consisting of NT-proBNP, Trefoil Factor 3, Apolipoprotein B, Angiopoietin-2, Osteoprotegerin, Alpha-2-Macroglobulin, Hepatocyte Growth Factor Receptor, Glutathione S Transferase alpha, Chromogranin A, IGF Binding Protein 4, Tenascin-C, Selenoprotein P, Macrophage Derived Chemokine, YKL-40, IGF Binding Protein 2
(n) one or more of the factors selected from the group consisting of blood pressure, weight, BMI, waist to hip ratio, waist circumference, diabetes duration, smoking status, imaging evidence of fatty liver, troponin levels, LV dysfunction, cardiovascular risk, other diabetes complications, retinal imaging, and nerve conduction studies, may further be detected.

In a ninth aspect, the present invention relates to a method of treating a group of patients who will benefit from metformin treatment, comprising the steps of
(i) administering an effective amount of metformin to a patient,
(ii) determining the level of GDF15 in a patient's sample, and
(iii) comparing the GDF15 level determined in step (ii) to that of a reference,
(iv) continuing administration of metformin to those patients exhibiting an increased level of GDF15.

In particular embodiments, the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, and hypertension.

In particular embodiments, the patient is at risk of developing or suffers from a disease or disorder selected from the group consisting of cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, the disease or disorder is diabetes. In particular, the disease or disorder is diabetes Type I, diabetes Type II, or gestational diabetes.

In particular embodiments, the effective amount of metformin administered in step (i) is sufficient to achieve the intended purpose, i.e. is sufficient to induce a response in a subject responding to metformin treatment. Accordingly, the effective amount of metformin administered in step (i) is an amount that induces a response to metformin treatment in a subject responding to metformin. In particular embodiments, metformin is administered in step (i) in an amount of 500-2000 mg, in particular in an amount of 500, 550, 600, 650, 700, 750, 800, 850, 900, 950, 1000, 1100, 1200, 1300, 1400, 1500, 1600, 1700, 1800, 1900, or 2000 mg. It is well-known to the person skilled in the art how to determine the amount of metformin sufficient to induce a response to metformin treatment in an individual responding to metformin.

In particular embodiments, GDF15 determined in step (ii) comprises an amino acid sequence as given in SEQ ID NO: 1. In embodiments, the functional variant exhibits the same functional properties as native GDF15. In particular, the functional variant exhibits at least 80% sequence identity to GDF15 according to SEQ ID NO: 1. In particular, the functional variant exhibits at least 85%, 90%, 95%, 97% or 99% sequence identity to GDF15 according to SEQ ID NO: 1. In particular embodiments, the functional variant exhibits 80%, 90%, or 99% sequence identity to GDF15 according to SEQ ID NO: 1.

In particular embodiments, the level of GDF15 or the functional variant thereof, is determined in step (ii) via any method well-known in the art. In particular, the level of GDF15 or the functional variant thereof, is determined in step (ii) via a method selected from the group consisting of ELISA, Western Blot, immunoprecipitation, HPLC, microarrays, mass spectroscopy, and sequencing. In particular embodiments, the level of GDF15 is determined using an immuno-detection assay.

In particular embodiments, the level of GDF15 or the functional variant thereof, is determined in step (ii) directly or indirectly using a GDF15-binding molecule. In particular, the level of GDF15 is determined using an antibody specific for GDF15. In particular, the level of GDF15 is determined using a monoclonal antibody specific for GDF15. In embodiments, the antibody competes with an antibody which recognizes a peptide comprising amino acids 197-308 of GDF-15. In particular, the antibody competes with an antibody which recognizes a peptide comprising amino acids 197-308 of GDF-15 according to SEQ ID NO: 1. In particular, the antibody recognizes a peptide comprising amino acids 197-308 of GDF-15 according to SEQ ID NO: 1.

In particular embodiments, the level of GDF15 or the functional variant thereof, in a patients sample is determined within hours after metformin administration. In particular, the level of GDF15 or a functional variant thereof, is determined within 1, 2, 3, 4, 5, 6, 7, 8, 9, 10, 11, 12, 13, 14, 15, 16, 17, 18, 19, 20, 21, 22, 23, or 24 hours after metformin administration. In particular, the level of GDF15 or a functional variant thereof, is determined within 12 hours after metformin administration, in particular within 6 hours after metformin administration. In particular, the level of GDF15 or a functional variant thereof, is determined within 1 to 12 hours, 2 to 10 hours, or 4 to 8 hours after metformin administration.

In particular embodiments, the level of GDF15 or the functional variant thereof, in a patient's sample is determined within days after metformin administration. In particular, the level of GDF15 or a functional variant thereof, is determined within 1, 2, 3, 4, 5, 6, or 7 days after metformin administration. In particular, the level of GDF15 or a functional variant thereof, is determined within 1 to 7 days, in particular within 1 to 5 days, in particular within 1 to 2 days after metformin administration.

In particular embodiments, the patient's sample is selected from the group consisting of bodily fluid and tissue sample. In particular, the body liquid sample is selected from the group consisting of whole blood, serum, plasma, sputum, saliva, and urine.

In further embodiments, one or more factors are determined in addition to GDF-15 in an optional step (v). In particular, the additional one or more factors are selected from the list consisting of:
(a) Fasting glucose levels,
(b) Post-prandial glucose levels
(c) Fructosamine levels
(d) Glycated albumin In particular embodiments, one or more of the factors selected from the list consisting of
(a) HbA1c
(b) Random glucose levels
(c) Fasting insulin levels
(d) Hemeostatic model assessment of insulin resistance (HOMAIR)
(e) Other measures of insulin resistance
(f) Lipid levels, in particular selected from the group consisting of HDL, LDL, total cholesterol, triglycerides, apolipoprotein B,
(g) Albuminuria, in particular microalbuminuria or macroalbuminuria
(h) Creatinine or estimated GFR,
(i) ALT level
(j) Vitamin $B_{12}$ level
(k) Cotinine level
(l) Telomere length
(m) one or more of the biomarker selected from the group consisting of NT-proBNP, Trefoil Factor 3, Apolipoprotein B, Angiopoietin-2, Osteoprotegerin, Alpha-2-Macroglobulin, Hepatocyte Growth Factor Receptor, Glutathione S Transferase alpha, Chromogranin A, IGF Binding Protein 4, Tenascin-C, Selenoprotein P, Macrophage Derived Chemokine, YKL-40, IGF Binding Protein 2
(n) one or more of the factors selected from the group consisting of blood pressure, weight, BMI, waist to hip ratio, waist circumference, diabetes duration, smoking status, imaging evidence of fatty liver, troponin levels, LV dysfunction, cardiovascular risk, other diabetes complications, retinal imaging, and nerve conduction studies, may be detected in an optional step (vi), in particular in order to confirm results obtained by the method of steps (i) to (iii) or (v).

Any of these additional factors determined in optional step (v) or (vi) is determined subsequent to step (iii) and prior to step (iv).

In particular embodiments, in step (iv) a therapeutically effective amount of metformin is administered to those patients who exhibit an increased level of GDF15. In particular embodiments, the level of GDF15 or the functional variant thereof, in particular the expression level, is increased by at least 25%, i.e. the level of GDF15 or a variant thereof, is increased by 25, 30, 35, 40, 45, 50, 55, 60, 65, 70, 75, 80, 85, 90, 95, 100, 110, 120, 130, 140, 150, 160, 170, 180, 190, or 200%. In particular embodiments, the level of GDF15 is increased by at least 50%, in particular by at least 75% or at least 100%. In particular embodiments, the level of GDF15 or a functional variant thereof, is increased by 25% to 200%, in particular by 30% to 150%, in particular by 50 to 100%.

In particular embodiments, the level of GDF15 or a functional variant thereof, is increased in comparison to a reference. The reference may be the level of GDF15 or a functional variant thereof, measured in a reference sample of the patient taken before metformin administration. In particular in a reference sample of the patient taken at a time point prior to metformin administration. The reference may be a representative reference value, in particular a reference value which is representative of the level of GDF-15 or a functional variant thereof, in a subject who has not obtained metformin administration. The reference value may be adjusted for factors associated with the propensity to prescribe metformin. In particular these factors are selected from the group consisting of age, sex, weight, prior cardiovascular event, a prior diagnosis of diabetes, serum creatinine, HbA1c, and fasting plasma glucose.

In particular embodiments, the patient is an individual who may benefit from the present invention. In particular, a patient is selected from the group consisting of mammal, reptile or bird that. In particular embodiments the patient is selected from the group consisting of laboratory animals (e.g. mouse, rat or rabbit), domestic animals (including e.g. guinea pig, rabbit, horse, donkey, cow, sheep, goat, pig, chicken, duck, camel, cat, dog, turtle, tortoise, snake, or lizard), or primates including chimpanzees, bonobos, gorillas and human beings. In particular, the patient is a human being.

In a tenth aspect, the present invention relates to a method of treating a patient or a group of patients who will not benefit from metformin treatment, comprising the steps of
(i) administering an effective amount of metformin to a patient,
(ii) determining the level of GDF15 in a patient's sample, and
(iii) comparing the GDF15 level determined in step (ii) to that of a reference,
(iv) discontinuing administration of metformin to those patients exhibiting a decreased level of GDF15,
and optionally
(v) administering an alternative treatment to those patients exhibiting a decreased level of GDF15.

In particular embodiments, the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, and hypertension.

In particular embodiments, the patient is at risk of developing or suffers from a disease or disorder selected from the group consisting of cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, the disease or disorder is diabetes. In particular, the disease or disorder is diabetes Type I, diabetes Type II, or gestational diabetes.

In particular embodiments, the effective amount of metformin administered in step (i) is sufficient to achieve the intended purpose, i.e. is sufficient to induce a response in a subject responding to metformin treatment. Accordingly, the effective amount of metformin administered in step (i) is an amount that induces a response to metformin treatment in a subject responding to metformin. In particular embodiments, metformin is administered in step (i) in an amount of 500-2000 mg, in particular in an amount of 500, 550, 600, 650, 700, 750, 800, 850, 900, 950, 1000, 1100, 1200, 1300, 1400, 1500, 1600, 1700, 1800, 1900, or 2000 mg. It is well-known to the person skilled in the art how to determine the amount of metformin sufficient to induce a response to metformin treatment in an individual responding to metformin.

In particular embodiments, GDF15 determined in step (ii) comprises an amino acid sequence as given in SEQ ID NO: 1. In embodiments, the functional variant exhibits the same functional properties as native GDF15. In particular, the functional variant exhibits at least 80% sequence identity to GDF15 according to SEQ ID NO: 1. In particular, the functional variant exhibits at least 85%, 90%, 95%, 97% or 99% sequence identity to GDF15 according to SEQ ID NO: 1. In particular embodiments, the functional variant exhibits 80%, 90%, or 99% sequence identity to GDF15 according to SEQ ID NO: 1.

In particular, the level of GDF15 or the functional variant thereof, is determined in step (ii) via a method selected from the group consisting of ELISA, Western Blot, immunoprecipitation, HPLC, microarrays, mass spectroscopy, and sequencing. In particular embodiments, the level of GDF15 is determined using an immuno-detection assay.

In particular embodiments, the level of GDF15 or the functional variant thereof, is determined in step (ii) directly or indirectly using a GDF15-binding molecule. In particular, the level of GDF15 is determined using an antibody specific for GDF15. In particular, the level of GDF15 is determined using a monoclonal antibody specific for GDF15. In embodiments, the antibody competes with an antibody which recognizes a peptide comprising amino acids 197-308 of GDF-15. In particular, the antibody competes with an antibody which recognizes a peptide comprising amino acids 197-308 of GDF-15 according to SEQ ID NO: 1. In particular, the antibody recognizes a peptide comprising amino acids 197-308 of GDF-15 according to SEQ ID NO: 1.

In particular embodiments, the level of GDF15 or the functional variant thereof, in a patients sample is determined within hours after metformin administration. In particular, the level of GDF15 or a functional variant thereof, is determined within 1, 2, 3, 4, 5, 6, 7, 8, 9, 10, 11, 12, 13, 14, 15, 16, 17, 18, 19, 20, 21, 22, 23, or 24 hours after metformin administration. In particular, the level of GDF15 or a functional variant thereof, is determined within 12 hours after metformin administration, in particular within 6 hours after metformin administration. In particular, the level of GDF15 or a functional variant thereof, is determined within 1 to 12 hours, 2 to 10 hours, or 4 to 8 hours after metformin administration.

In particular embodiments, the level of GDF15 or the functional variant thereof, in a patient's sample is determined within days after metformin administration. In particular, the level of GDF15 or a functional variant thereof, is determined within 1, 2, 3, 4, 5, 6, or 7 days after metformin administration. In particular, the level of GDF15 or a functional variant thereof, is determined within 1 to 7 days, in particular within 1 to 5 days, in particular within 1 to 2 days after metformin administration.

In particular embodiments, the patient's sample is selected from the group consisting of bodily fluid and tissue sample. In particular, the body liquid sample is selected from the group consisting of whole blood, serum, plasma, sputum, saliva, and urine.

In further embodiments, one or more factors are determined in addition to GDF-15 in an optional step (vi). In particular, the additional one or more factors are selected from the list consisting of:
  (e) Fasting glucose levels,
  (f) Post-prandial glucose levels
  (g) Fructosamine levels
  (h) Glycated albumin In particular embodiments, one or more of the factors selected from the list consisting of
  (o) HbA1c
  (p) Random glucose levels
  (q) Fasting insulin levels
  (r) Hemeostatic model assessment of insulin resistance (HOMAIR)
  (s) Other measures of insulin resistance
  (t) Lipid levels, in particular selected from the group consisting of HDL, LDL, total cholesterol, triglycerides, apolipoprotein B,
  (u) Albuminuria, in particular microalbuminuria or macroalbuminuria
  (v) Creatinine or estimated GFR,
  (w) ALT level
  (x) Vitamin $B_{12}$ level
  (y) Cotinine level
  (z) Telomere length
  (aa) one or more of the biomarker selected from the group consisting of NT-proBNP, Trefoil Factor 3, Apolipoprotein B, Angiopoietin-2, Osteoprotegerin, Alpha-2-Macroglobulin, Hepatocyte Growth Factor Receptor, Glutathione S Transferase alpha, Chromogranin A, IGF Binding Protein 4, Tenascin-C, Selenoprotein P, Macrophage Derived Chemokine, YKL-40, IGF Binding Protein 2

(bb) one or more of the factors selected from the group consisting of blood pressure, weight, BMI, waist to hip ratio, waist circumference, diabetes duration, smoking status, imaging evidence of fatty liver, troponin levels, LV dysfunction, cardiovascular risk, other diabetes complications, retinal imaging, and nerve conduction studies, may be detected in an optional step (vii), in particular in order to confirm results obtained by the method of steps (i) to (iv).

In particular embodiments, in step (iv) metformin administration is discontinued in those patients who exhibit no increased level of GDF15, in particular in patients who exhibit an unaltered or a decreased level of GDF15. In particular embodiments, the level of GDF15 or a functional variant thereof, is decreased in comparison to a reference. The reference may be the level of GDF15 or a functional variant thereof, measured in a reference sample of the patient taken before metformin administration. In particular in a reference sample of the patient taken at a time point prior to metformin administration. The reference may be a representative reference value, in particular a reference value which is representative of the level of GDF-15 or a functional variant thereof, in a subject who has not obtained metformin administration. The reference value may be adjusted for factors associated with the propensity to prescribe metformin. In particular these factors are selected from the group consisting of age, sex, weight, prior cardiovascular event, a prior diagnosis of diabetes, serum creatinine, HbA1c, and fasting plasma glucose.

In particular embodiments, a patient is selected from the group consisting of mammal, reptile or bird that. In particular embodiments the patient is selected from the group consisting of laboratory animals (e.g. mouse, rat or rabbit), domestic animals (including e.g. guinea pig, rabbit, horse, donkey, cow, sheep, goat, pig, chicken, duck, camel, cat, dog, turtle, tortoise, snake, or lizard), or primates including chimpanzees, bonobos, gorillas and human beings. In particular, the patient is a human being.

In a particular embodiment, the alternative treatment in optional step (v) is selected from the group consisting of sulfonylureas, dopamine agonist, DPP-4 inhibitors, glucagon-like peptides, meglitinides, amylinomimetic, alpha-glucosidase inhibitors, SGLT2 inhibitors, and thiazolidinediones.

In an eleventh aspect, the present invention relates to a method of identifying a patient who will not benefit from metformin treatment, comprising the steps of (i) administering an effective amount of metformin to a patient, (ii) determining the level of GDF15 in a patient's sample, and (iii) comparing the GDF15 level determined in step (ii) to that of a reference, wherein an unaltered or decreased level of GDF15 is indicative of a patient not responding to metformin administration.

In particular embodiments, the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, and hypertension.

In particular embodiments, the patient is at risk of developing or suffers from a disease or disorder selected from the group consisting of cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, the disease or disorder is diabetes. In particular, the disease or disorder is diabetes Type I, diabetes Type II, or gestational diabetes.

In particular embodiments, the effective amount of metformin administered in step (i) is sufficient to achieve the intended purpose, i.e. is sufficient to induce a response in a subject responding to metformin treatment. Accordingly, the effective amount of metformin administered in step (i) is an amount that induces a response to metformin treatment in a subject responding to metformin. In particular embodiments, metformin is administered in step (i) in an amount of 500-2000 mg, in particular in an amount of 500, 550, 600, 650, 700, 750, 800, 850, 900, 950, 1000, 1100, 1200, 1300, 1400, 1500, 1600, 1700, 1800, 1900, or 2000 mg. It is well-known to the person skilled in the art how to determine the amount of metformin sufficient to induce a response to metformin treatment in an individual responding to metformin.

In particular embodiments, GDF15 determined in step (ii) comprises an amino acid sequence as given in SEQ ID NO: 1. In embodiments, the functional variant exhibits the same functional properties as native GDF15. In particular, the functional variant exhibits at least 80% sequence identity to GDF15 according to SEQ ID NO: 1. In particular, the functional variant exhibits at least 85%, 90%, 95%, 97% or 99% sequence identity to GDF15 according to SEQ ID NO: 1. In particular embodiments, the functional variant exhibits 80%, 90%, or 99% sequence identity to GDF15 according to SEQ ID NO: 1.

In particular, the level of GDF15 or the functional variant thereof, is determined in step (ii) via a method selected from the group consisting of ELISA, Western Blot, immunoprecipitation, HPLC, microarrays, mass spectroscopy, and sequencing. In particular embodiments, the level of GDF15 is determined using an immuno-detection assay.

In particular embodiments, the level of GDF15 or the functional variant thereof, is determined in step (ii) directly or indirectly using a GDF15-binding molecule. In particular, the level of GDF15 is determined using an antibody specific for GDF15. In particular, the level of GDF15 is determined using a monoclonal antibody specific for GDF15. In embodiments, the antibody competes with an antibody which recognizes a peptide comprising amino acids 197-308 of GDF-15. In particular, the antibody competes with an antibody which recognizes a peptide comprising amino acids 197-308 of GDF-15 according to SEQ ID NO: 1. In particular, the antibody recognizes a peptide comprising amino acids 197-308 of GDF-15 according to SEQ ID NO: 1.

In particular embodiments, the level of GDF15 or the functional variant thereof, in a patients sample is determined within hours after metformin administration. In particular, the level of GDF15 or a functional variant thereof, is determined within 1, 2, 3, 4, 5, 6, 7, 8, 9, 10, 11, 12, 13, 14, 15, 16, 17, 18, 19, 20, 21, 22, 23, or 24 hours after metformin administration. In particular, the level of GDF15 or a functional variant thereof, is determined within 12 hours after metformin administration, in particular within 6 hours after metformin administration. In particular, the level of GDF15 or a functional variant thereof, is determined within 1 to 12 hours, 2 to 10 hours, or 4 to 8 hours after metformin administration.

In particular embodiments, the level of GDF15 or the functional variant thereof, in a patient's sample is determined within days after metformin administration. In particular, the level of GDF15 or a functional variant thereof, is determined within 1, 2, 3, 4, 5, 6, or 7 days after metformin administration. In particular, the level of GDF15 or a functional variant thereof, is determined within 1 to 7 days, in particular within 1 to 5 days, in particular within 1 to 2 days after metformin administration.

In particular embodiments, the patient's sample is selected from the group consisting of bodily fluid and tissue sample. In particular, the body liquid sample is selected from the group consisting of whole blood, serum, plasma, sputum, saliva, and urine.

In further embodiments, one or more factors are determined in addition to GDF-15 in an optional step (iv). In particular, the additional one or more factors are selected from the list consisting of:
(i) Fasting glucose levels,
(j) Post-prandial glucose levels
(k) Fructosamine levels
(l) Glycated albumin In particular embodiments, one or more of the factors selected from the list consisting of
(cc) HbA1c
(dd) Random glucose levels
(ee) Fasting insulin levels
(ff) Hemeostatic model assessment of insulin resistance (HOMAIR)
(gg) Other measures of insulin resistance
(hh) Lipid levels, in particular selected from the group consisting of HDL, LDL, total cholesterol, triglycerides, apolipoprotein B,
(ii) Albuminuria, in particular microalbuminuria or macroalbuminuria
(jj) Creatinine or estimated GFR,
(kk) ALT level
(ll) Vitamin $B_{12}$ level
(mm) Cotinine level
(nn) Telomere length
(oo) one or more of the biomarker selected from the group consisting of NT-proBNP, Trefoil Factor 3, Apolipoprotein B, Angiopoietin-2, Osteoprotegerin, Alpha-2-Macroglobulin, Hepatocyte Growth Factor Receptor, Glutathione S Transferase alpha, Chromogranin A, IGF Binding Protein 4, Tenascin-C, Selenoprotein P, Macrophage Derived Chemokine, YKL-40, IGF Binding Protein 2
(pp) one or more of the factors selected from the group consisting of blood pressure, weight, BMI, waist to hip ratio, waist circumference, diabetes duration, smoking status, imaging evidence of fatty liver, troponin levels, LV dysfunction, cardiovascular risk, other diabetes complications, retinal imaging, and nerve conduction studies,
may be detected in an optional step (v), in particular in order to confirm results obtained by the method of steps (i) to (iii).

In particular embodiments, in step (iv) metformin administration is discontinued in those patients who exhibit no increased level of GDF15, in particular in patients who exhibit an unaltered or a decreased level of GDF15. In particular embodiments, the level of GDF15 or a functional variant thereof, is decreased in comparison to a reference. The reference may be the level of GDF15 or a functional variant thereof, measured in a reference sample of the patient taken before metformin administration. In particular in a reference sample of the patient taken at a time point prior to metformin administration. The reference may be a representative reference value, in particular a reference value which is representative of the level of GDF-15 or a functional variant thereof, in a subject who has not obtained metformin administration. The reference value may be adjusted for factors associated with the propensity to prescribe metformin. In particular these factors are selected from the group consisting of age, sex, weight, prior cardiovascular event, a prior diagnosis of diabetes, serum creatinine, HbA1c, and fasting plasma glucose.

In particular embodiments, a patient is selected from the group consisting of mammal, reptile or bird that. In particular embodiments the patient is selected from the group consisting of laboratory animals (e.g. mouse, rat or rabbit), domestic animals (including e.g. guinea pig, rabbit, horse, donkey, cow, sheep, goat, pig, chicken, duck, camel, cat, dog, turtle, tortoise, snake, or lizard), or primates including chimpanzees, bonobos, gorillas and human beings. In particular, the patient is a human being.

In a twelfth aspect, the present invention relates to sulfonylureas, dopamine agonist, DPP-4 inhibitors, glucagon-like peptides, meglitinides, amylinomimetic, alpha-glucosidase inhibitors, SGLT2 inhibitors, and/or thiazolidinediones for use in treating a patient, wherein the patient exhibits an unaltered or decreased level of GDF15 in response to metformin treatment, and wherein the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease or reduced longevity.

In particular embodiments, the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, and hypertension.

In particular embodiments, the patient is at risk of developing or suffers from a disease or disorder selected from the group consisting of cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, the disease or disorder is diabetes. In particular the disease or disorder is diabetes Type I, diabetes Type II, or gestational diabetes.

In particular embodiments, GDF15 comprises an amino acid sequence as given in SEQ ID NO: 1. In embodiments, the functional variant exhibits the same functional properties as native GDF15. In particular, the functional variant exhibits at least 80% sequence identity to GDF15 according to SEQ ID NO: 1. In particular, the functional variant exhibits at least 85%, 90%, 95%, 97% or 99% sequence identity to GDF15 according to SEQ ID NO: 1. In particular embodiments, the functional variant exhibits 80%, 90%, or 99% sequence identity to GDF15 according to SEQ ID NO: 1.

In particular embodiments, the level of GDF15 is not increased by at least 25%. In particular, the level of GDF15 is unaltered or decreased. In embodiments, the patient exhibits an unaltered or decreased expression level of GDF15 or a functional variant thereof.

In particular embodiments, the level of GDF15 is not increased in comparison to a reference. The reference may be the GDF15 level measured in a reference sample of the patient before metformin administration. In particular in a reference sample of the patient taken at a time point prior to metformin administration. The reference may be a representative reference value, in particular a reference value which is representative of the level of GDF-15 in a subject who has not obtained metformin administration. The reference value may be adjusted for factors associated with the propensity to prescribe metformin. In particular these factors are selected from the group consisting of age, sex, weight, prior cardiovascular event, a prior diagnosis of diabetes, serum creatinine, HbA1c, and fasting plasma glucose.

In particular embodiments, the patient is an individual who may benefit from the present invention. In particular, a patient is selected from the group consisting of mammal, reptile or bird that. In particular embodiments the patient is selected from the group consisting of laboratory animals (e.g. mouse, rat or rabbit), domestic animals (including e.g. guinea pig, rabbit, horse, donkey, cow, sheep, goat, pig, chicken, duck, camel, cat, dog, turtle, tortoise, snake, or lizard), or primates including chimpanzees, bonobos, gorillas and human beings. In particular, the patient is a human being.

In a thirteenth aspect, the present invention relates to a method of shortening the time for determining whether a patient responds to metformin administration, comprising the steps of
 (i) administering an effective amount of metformin to a patient,
 (ii) determining the level of GDF15 in a patient's sample, and
 (iii) comparing the GDF15 level determined in step (ii) to that of a reference,
 wherein an increased level of GDF15 is indicative of a patient responding to metformin administration, and wherein an unaltered or decreased level of GDF15 is indicative of a patient not responding to metformin administration.

In particular embodiments, the time for determining whether a patient responds to metformin administration is below 4 weeks. In particular embodiments, the time for determining whether a patient responds to metformin administration is below 1 week. In particular embodiments, the time for determining whether a patient responds to metformin administration is below 1 day. In particular embodiments, the time for determining whether a patient responds to metformin administration is below 12 hours. In particular embodiments, the time for determining whether a patient responds to metformin administration is within 8 hours.

In particular embodiments, the time for determining whether a patient responds to metformin administration is between 4 hours and 4 weeks. In particular embodiments, the time for determining whether a patient responds to metformin administration is between 4 hours and 1 week. In particular embodiments, the time for determining whether a patient responds to metformin administration is between 4 hours and 12 hours. In particular embodiments, the time for determining whether a patient responds to metformin administration is between 4 hours and 8 hours.

In particular embodiments, the time for determining whether a patient responds to metformin administration is reduced to 4 weeks. In particular embodiments, the time for determining whether a patient responds to metformin administration is reduced to 1 week.

In particular embodiments, the time for determining whether a patient responds to metformin administration is reduced to 1 day. In particular embodiments, the time for determining whether a patient responds to metformin administration is reduced to 12 hours. In particular embodiments, the time for determining whether a patient responds to metformin administration is reduced to 8 hours. In particular embodiments, the time for determining whether a patient responds to metformin administration is reduced to 6 hours.

In particular embodiments, the time for determining whether a patient responds to metformin administration is reduced to 4 hours to 4 weeks. In particular embodiments, the time for determining whether a patient responds to metformin administration is reduced to 4 hours to 1 week. In particular embodiments, the time for determining whether a patient responds to metformin administration is reduced to 4 hours to 12 hours. In particular embodiments, the time for determining whether a patient responds to metformin administration is reduced to 4 hours to 8 hours.

In particular embodiments, the time for determining whether a patient responds to metformin administration is reduced in comparison to HbA1c measurements.

In particular embodiments, the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, and hypertension.

In particular embodiments, the patient is at risk of developing or suffers from a disease or disorder selected from the group consisting of cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, the disease or disorder is diabetes. In particular, the disease or disorder is diabetes Type I, diabetes Type II, or gestational diabetes.

In particular embodiments, the effective amount of metformin administered in step (i) is sufficient to achieve the intended purpose, i.e. is sufficient to induce a response in a subject responding to metformin treatment. Accordingly, the effective amount of metformin administered in step (i) is an amount that induces a response to metformin treatment in a subject responding to metformin. In particular embodiments, metformin is administered in step (i) in an amount of 500-2000 mg, in particular in an amount of 500, 550, 600, 650, 700, 750, 800, 850, 900, 950, 1000, 1100, 1200, 1300, 1400, 1500, 1600, 1700, 1800, 1900, or 2000 mg. It is well-known to the person skilled in the art how to determine the amount of metformin sufficient to induce a response to metformin treatment in an individual responding to metformin.

In particular embodiments, GDF15 determined in step (ii) comprises an amino acid sequence as given in SEQ ID NO: 1. In embodiments, the functional variant exhibits the same functional properties as native GDF15. In particular, the functional variant exhibits at least 80% sequence identity to GDF15 according to SEQ ID NO: 1. In particular, the functional variant exhibits at least 85%, 90%, 95%, 97% or 99% sequence identity to GDF15 according to SEQ ID NO: 1. In particular embodiments, the functional variant exhibits 80%, 90%, or 99% sequence identity to GDF15 according to SEQ ID NO: 1.

In particular, the level of GDF15 or the functional variant thereof, is determined in step (ii) via a method selected from the group consisting of ELISA, Western Blot, immunoprecipitation, HPLC, microarrays, mass spectroscopy, and sequencing. In particular embodiments, the level of GDF15 is determined using an immuno-detection assay.

In particular embodiments, the level of GDF15 or the functional variant thereof, is determined in step (ii) directly or indirectly using a GDF15-binding molecule. In particular, the level of GDF15 is determined using an antibody specific for GDF15. In particular, the level of GDF15 is determined using a monoclonal antibody specific for GDF15. In particular, the antibody competes with an antibody which recognizes a peptide comprising amino acids 197-308 of GDF-15 according to SEQ ID NO: 1. In particular, the antibody recognizes a peptide comprising amino acids 197-308 of GDF-15 according to SEQ ID NO: 1.

In particular embodiments, the level of GDF15 or the functional variant thereof, in a patients sample is determined within hours after metformin administration. In particular, the level of GDF15 or a functional variant thereof, is determined within 1, 2, 3, 4, 5, 6, 7, 8, 9, 10, 11, 12, 13, 14, 15, 16, 17, 18, 19, 20, 21, 22, 23, or 24 hours after metformin administration. In particular, the level of GDF15 or a functional variant thereof, is determined within 12 hours after metformin administration, in particular within 6 hours after metformin administration. In particular, the level of GDF15 or a functional variant thereof, is determined within 1 to 12 hours, 2 to 10 hours, or 4 to 8 hours after metformin administration.

In particular embodiments, the level of GDF15 or the functional variant thereof, in a patient's sample is determined within days after metformin administration. In particular, the level of GDF15 or a functional variant thereof, is determined within 1, 2, 3, 4, 5, 6, or 7 days after metformin administration. In particular, the level of GDF15 or a functional variant thereof, is determined within 1 to 7 days, in particular within 1 to 5 days, in particular within 1 to 2 days after metformin administration.

In particular embodiments, the patient's sample is selected from the group consisting of bodily fluid and tissue sample. In particular, the body liquid sample is selected from the group consisting of whole blood, serum, plasma, sputum, saliva, and urine.

In further embodiments, one or more factors are determined in addition to GDF-15 in an optional step (iv). In particular, the additional one or more factors are selected from the list consisting of:
(a) Fasting glucose levels,
(b) Post-prandial glucose levels
(c) Fructosamine levels
(d) Glycated albumin In particular embodiments, one or more of the factors selected from the list consisting of
(a) HbA1c
(b) Random glucose levels
(c) Fasting insulin levels
(d) Hemeostatic model assessment of insulin resistance (HOMAIR)
(e) Other measures of insulin resistance
(f) Lipid levels, in particular selected from the group consisting of HDL, LDL, total cholesterol, triglycerides, apolipoprotein B,
(g) Albuminuria, in particular microalbuminuria or macroalbuminuria
(h) Creatinine or estimated GFR,
(i) ALT level
(j) Vitamin $B_{12}$ level
(k) Cotinine level
(l) Telomere length
(m) one or more of the biomarker selected from the group consisting of NT-proBNP, Trefoil Factor 3, Apolipoprotein B, Angiopoietin-2, Osteoprotegerin, Alpha-2-Macroglobulin, Hepatocyte Growth Factor Receptor, Glutathione S Transferase alpha, Chromogranin A, IGF Binding Protein 4, Tenascin-C, Selenoprotein P, Macrophage Derived Chemokine, YKL-40, IGF Binding Protein 2
(n) one or more of the factors selected from the group consisting of blood pressure, weight, BMI, waist to hip ratio, waist circumference, diabetes duration, smoking status, imaging evidence of fatty liver, troponin levels, LV dysfunction, cardiovascular risk, other diabetes complications, retinal imaging, and nerve conduction studies, may be detected in an optional step (v), in particular in order to confirm results obtained by the method of steps (i) to (iii).

In particular, a patient is selected from the group consisting of mammal, reptile or bird that. In particular embodiments the patient is selected from the group consisting of laboratory animals (e.g. mouse, rat or rabbit), domestic animals (including e.g. guinea pig, rabbit, horse, donkey, cow, sheep, goat, pig, chicken, duck, camel, cat, dog, turtle, tortoise, snake, or lizard), or primates including chimpanzees, bonobos, gorillas and human beings. In particular, the patient is a human being.

In a fourteenth aspect, the present invention relates to a method of preventing, delaying, and/or treating diabetes associated complications in a patient, comprising the steps of
(i) administering an effective amount of metformin to a patient, (ii) determining the level of GDF15 in a patient's sample, and (iii) comparing the GDF15 level determined in step (ii) to that of a reference, (iv) continuing metformin administration to those patients exhibiting an increased level of GDF15, and discontinuing administration of metformin to those patients exhibiting an unaltered or decreased level of GDF15, and optionally (v) administering an alternative treatment to those patients exhibiting an unaltered or decreased level of GDF15.

In particular embodiments, diabetes associated complications are selected from the group consisting of hypoglycemia, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, diabetes associated complications are selected from the group consisting of hypoglycemia, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, and hypertension.

In particular embodiments, diabetes associated complications are selected from the group consisting of cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, the patient is at risk of developing or suffers from diabetes. In particular, the patient is at risk of developing or suffers from diabetes Type I, diabetes Type II, or gestational diabetes.

In particular embodiments, the effective amount of metformin administered in step (i) is sufficient to achieve the intended purpose, i.e. is sufficient to induce a response in a subject responding to metformin treatment. Accordingly, the effective amount of metformin administered in step (i) is an amount that induces a response to metformin treatment in a subject responding to metformin. In particular embodiments, metformin is administered in step (i) in an amount of 500-2000 mg, in particular in an amount of 500, 550, 600, 650, 700, 750, 800, 850, 900, 950, 1000, 1100, 1200, 1300, 1400, 1500, 1600, 1700, 1800, 1900, or 2000 mg. It is well-known to the person skilled in the art how to determine the amount of metformin sufficient to induce a response to metformin treatment in an individual responding to metformin.

In particular embodiments, GDF15 determined in step (ii) comprises an amino acid sequence as given in SEQ ID NO: 1. In embodiments, the functional variant exhibits the same functional properties as native GDF15. In particular, the functional variant exhibits at least 80% sequence identity to GDF15 according to SEQ ID NO: 1. In particular, the functional variant exhibits at least 85%, 90%, 95%, 97% or 99% sequence identity to GDF15 according to SEQ ID NO: 1. In particular embodiments, the functional variant exhibits 80%, 90%, or 99% sequence identity to GDF15 according to SEQ ID NO: 1.

In particular, the level of GDF15 or the functional variant thereof, is determined in step (ii) via a method selected from the group consisting of ELISA, Western Blot, immunoprecipitation, HPLC, microarrays, mass spectroscopy, and sequencing. In particular embodiments, the level of GDF15 is determined using an immuno-detection assay.

In particular embodiments, the level of GDF15 or the functional variant thereof, is determined in step (ii) directly or indirectly using a GDF15-binding molecule. In particular, the level of GDF15 is determined using an antibody specific for GDF15. In particular, the level of GDF15 is determined using a monoclonal antibody specific for GDF15. In particular, the antibody competes with an antibody which recognizes a peptide comprising amino acids 197-308 of GDF-15 according to SEQ ID NO: 1. In particular, the antibody recognizes a peptide comprising amino acids 197-308 of GDF-15 according to SEQ ID NO: 1.

In particular embodiments, the level of GDF15 or the functional variant thereof, in a patients sample is determined within hours after metformin administration. In particular, the level of GDF15 or a functional variant thereof, is determined within 1, 2, 3, 4, 5, 6, 7, 8, 9, 10, 11, 12, 13, 14, 15, 16, 17, 18, 19, 20, 21, 22, 23, or 24 hours after metformin administration. In particular, the level of GDF15 or a functional variant thereof, is determined within 12 hours after metformin administration, in particular within 6 hours after metformin administration. In particular, the level of GDF15 or a functional variant thereof, is determined within 1 to 12 hours, 2 to 10 hours, or 4 to 8 hours after metformin administration.

In particular embodiments, the level of GDF15 or the functional variant thereof, in a patient's sample is determined within days after metformin administration. In particular, the level of GDF15 or a functional variant thereof, is determined within 1, 2, 3, 4, 5, 6, or 7 days after metformin administration. In particular, the level of GDF15 or a functional variant thereof, is determined within 1 to 7 days, in particular within 1 to 5 days, in particular within 1 to 2 days after metformin administration.

In particular embodiments, the patient's sample is selected from the group consisting of bodily fluid and tissue sample. In particular, the body liquid sample is selected from the group consisting of whole blood, serum, plasma, sputum, saliva, and urine.

In further embodiments, one or more factors are determined in addition to GDF-15 in an optional step (vi). In particular, the additional one or more factors are selected from the list consisting of:
(a) Fasting glucose levels,
(b) Post-prandial glucose levels
(c) Fructosamine levels
(d) Glycated albumin In particular embodiments, one or more of the factors selected from the list consisting of
(a) HbA1c
(b) Random glucose levels
(c) Fasting insulin levels
(d) Hemeostatic model assessment of insulin resistance (HOMAIR)
(e) Other measures of insulin resistance
(f) Lipid levels, in particular selected from the group consisting of HDL, LDL, total cholesterol, triglycerides, apolipoprotein B,
(g) Albuminuria, in particular microalbuminuria or macroalbuminuria
(h) Creatinine or estimated GFR,
(i) ALT level (j) Vitamin B$_{12}$ level
(k) Cotinine level
(l) Telomere length
(m) one or more of the biomarker selected from the group consisting of NT-proBNP, Trefoil Factor 3, Apolipoprotein B, Angiopoietin-2, Osteoprotegerin, Alpha-2-Macroglobulin, Hepatocyte Growth Factor Receptor, Glutathione S Transferase alpha, Chromogranin A, IGF Binding Protein 4, Tenascin-C, Selenoprotein P, Macrophage Derived Chemokine, YKL-40, IGF Binding Protein 2
(n) one or more of the factors selected from the group consisting of blood pressure, weight, BMI, waist to hip ratio, waist circumference, diabetes duration, smoking status, imaging evidence of fatty liver, troponin levels, LV dysfunction, cardiovascular risk, other diabetes complications, retinal imaging, and nerve conduction studies, may be detected in an optional step (vii), in particular in order to confirm results obtained by the method of steps (i) to (iii).

Any of these additional factors determined in optional step (vi) or (vii) is determined subsequent to step (iii) and prior to step (iv).

In a particular embodiment, the alternative treatment in optional step (v) is selected from the group consisting of sulfonylureas, dopamine agonist, DPP-4 inhibitors, glucagon-like peptides, meglitinides, amylinomimetic, alpha-glucosidase inhibitors, SGLT2 inhibitors, and thiazolidinediones.

In particular, a patient is selected from the group consisting of mammal, reptile or bird that. In particular embodiments the patient is selected from the group consisting of laboratory animals (e.g. mouse, rat or rabbit), domestic animals (including e.g. guinea pig, rabbit, horse, donkey, cow, sheep, goat, pig, chicken, duck, camel, cat, dog, turtle, tortoise, snake, or lizard), or primates including chimpanzees, bonobos, gorillas and human beings. In particular, the patient is a human being.

In a fifteenth aspect, the present invention relates to a method of preventing, delaying, and/or treating diabetes associated complications in a patient, comprising the steps of (i) administering an effective amount of metformin to a patient,
(ii) determining the level of GDF15 in a patient's sample, and
(iii) comparing the GDF15 level determined in step (ii) to that of a reference, wherein an increased level of GDF15 is indicative of the patient responding to metformin treatment, and an unaltered or decreased level of GDF15, is indicative of the patient not responding to metformin treatment,
and optionally
(iv) considering an alternative treatment for those patients exhibiting an unaltered or decreased level of GDF15 in order to reduce diabetes associated complications in said patient.

In particular embodiments, diabetes associated complications are selected from the group consisting of hypoglycemia, polycystic ovary syndrome, hirsutism, amenorrhea, non-alcoholic fatty liver disease, non-alcoholic steatohepatitis, infertility, obesity, Vitamin B12 deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, diabetes associated complications are selected from the group consisting of hypoglycemia, polycystic ovary syndrome, hirsutism, amenorrhea, non-alcoholic fatty liver disease, non-alcoholic steatohepatitis, infertility, obesity, Vitamin B12 deficiency, insulin resistance, and other risk factors for ischemic heart disease or myocardial infarction such as but not limited to angina, dyslipidemia, and hypertension.

In particular embodiments, diabetes associated complications are selected from the group consisting of cancer, cognitive decline, dementia, frailty, falls, unsteadiness, erectile dysfunction, sexual dysfunction, chronic pain, foot ulceration, retinal disease, decreased vision, renal disease and reduced longevity.

In particular embodiments, the patient is at risk of developing or suffers from diabetes. In particular, the patient is at risk of developing or suffers from diabetes Type I, diabetes Type II, or gestational diabetes.

In particular embodiments, the effective amount of metformin administered in step (i) is sufficient to achieve the intended purpose, i.e. is sufficient to induce a response in a subject responding to metformin treatment. Accordingly, the effective amount of metformin administered in step (i) is an amount that induces a response to metformin treatment in a subject responding to metformin. In particular embodiments, metformin is administered in step (i) in an amount of 500-2000 mg, in particular in an amount of 500, 550, 600, 650, 700, 750, 800, 850, 900, 950, 1000, 1100, 1200, 1300, 1400, 1500, 1600, 1700, 1800, 1900, or 2000 mg. It is well-known to the person skilled in the art how to determine the amount of metformin sufficient to induce a response to metformin treatment in an individual responding to metformin.

In particular embodiments, GDF15 determined in step (ii) comprises an amino acid sequence as given in SEQ ID NO: 1. In embodiments, the functional variant exhibits the same functional properties as native GDF15. In particular, the functional variant exhibits at least 80% sequence identity to GDF15 according to SEQ ID NO: 1. In particular, the functional variant exhibits at least 85%, 90%, 95%, 97% or 99% sequence identity to GDF15 according to SEQ ID NO: 1. In particular embodiments, the functional variant exhibits 80%, 90%, or 99% sequence identity to GDF15 according to SEQ ID NO: 1.

In particular, the level of GDF15 or the functional variant thereof, is determined in step (ii) via a method selected from the group consisting of ELISA, Western Blot, immunoprecipitation, HPLC, microarrays, mass spectroscopy, and sequencing. In particular embodiments, the level of GDF15 is determined using an immuno-detection assay.

In particular embodiments, the level of GDF15 or the functional variant thereof, is determined in step (ii) directly or indirectly using a GDF15-binding molecule. In particular, the level of GDF15 is determined using an antibody specific for GDF15. In particular, the level of GDF15 is determined using a monoclonal antibody specific for GDF15. In embodiments, the antibody competes with an antibody which recognizes a peptide comprising amino acids 197-308 of GDF-15. In particular, the antibody competes with an antibody which recognizes a peptide comprising amino acids 197-308 of GDF-15 according to SEQ ID NO: 1. In particular, the antibody recognizes a peptide comprising amino acids 197-308 of GDF-15 according to SEQ ID NO: 1.

In particular embodiments, the level of GDF15 or the functional variant thereof, in a patients sample is determined within hours after metformin administration. In particular, the level of GDF15 or a functional variant thereof, is determined within 1, 2, 3, 4, 5, 6, 7, 8, 9, 10, 11, 12, 13, 14, 15, 16, 17, 18, 19, 20, 21, 22, 23, or 24 hours after metformin administration. In particular, the level of GDF15 or a functional variant thereof, is determined within 12 hours after metformin administration, in particular within 6 hours after metformin administration. In particular, the level of GDF15 or a functional variant thereof, is determined within 1 to 12 hours, 2 to 10 hours, or 4 to 8 hours after metformin administration.

In particular embodiments, the level of GDF15 or the functional variant thereof, in a patient's sample is determined within days after metformin administration. In particular, the level of GDF15 or a functional variant thereof, is determined within 1, 2, 3, 4, 5, 6, or 7 days after metformin administration. In particular, the level of GDF15 or a functional variant thereof, is determined within 1 to 7 days, in particular within 1 to 5 days, in particular within 1 to 2 days after metformin administration.

In particular embodiments, the patient's sample is selected from the group consisting of bodily fluid and tissue sample. In particular, the body liquid sample is selected from the group consisting of whole blood, serum, plasma, sputum, saliva, and urine.

In further embodiments, one or more factors are determined in addition to GDF-15 in an optional step (v). In particular, the additional one or more factors are selected from the list consisting of:
(e) Fasting glucose levels,
(f) Post-prandial glucose levels
(g) Fructosamine levels
(h) Glycated albumin In particular embodiments, one or more of the factors selected from the list consisting of
(o) HbA1c
(p) Random glucose levels
(q) Fasting insulin levels
(r) Hemeostatic model assessment of insulin resistance (HOMAIR)
(s) Other measures of insulin resistance
(t) Lipid levels, in particular selected from the group consisting of HDL, LDL, total cholesterol, triglycerides, apolipoprotein B,
(u) Albuminuria, in particular microalbuminuria or macroalbuminuria
(v) Creatinine or estimated GFR,
(w) ALT level
(x) Vitamin $B_{12}$ level
(y) Cotinine level
(z) Telomere length
(aa) one or more of the biomarker selected from the group consisting of NT-proBNP, Trefoil Factor 3, Apolipoprotein B, Angiopoietin-2, Osteoprotegerin, Alpha-2-Macroglobulin, Hepatocyte Growth Factor Receptor, Glutathione S Transferase alpha, Chromogranin A, IGF Binding Protein 4, Tenascin-C, Selenoprotein P, Macrophage Derived Chemokine, YKL-40, IGF Binding Protein 2
(bb) one or more of the factors selected from the group consisting of blood pressure, weight, BMI, waist to hip ratio, waist circumference, diabetes duration, smoking status, imaging evidence of fatty liver, troponin levels, LV dysfunction, cardiovascular risk, other diabetes complications, retinal imaging, and nerve conduction studies,
may be detected in an optional step (vi), in particular in order to confirm results obtained by the method of steps (i) to (iii).

Any of these additional factors determined in optional step (v) or (vi) is determined subsequent to step (iii) and prior to step (iv).

In a particular embodiment, the alternative treatment considered in optional step (v) is selected from the group consisting of sulfonylureas, dopamine agonist, DPP-4 inhibitors, glucagon-like peptides, meglitinides, amylinomimetic, alpha-glucosidase inhibitors, SGLT2 inhibitors, and thiazolidinediones.

In particular, a patient is selected from the group consisting of mammal, reptile or bird that. In particular embodiments the patient is selected from the group consisting of laboratory animals (e.g. mouse, rat or rabbit), domestic animals (including e.g. guinea pig, rabbit, horse, donkey, cow, sheep, goat, pig, chicken, duck, camel, cat, dog, turtle, tortoise, snake, or lizard), or primates including chimpanzees, bonobos, gorillas and human beings. In particular, the patient is a human being.

In particular, the present invention relates to the following items:
1. Metformin for use in treating a patient,
    wherein the patient exhibits an increased level of GDF15 in response to metformin treatment, and
    wherein the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease or reduced longevity.
2. Metformin for use according to item 1, wherein the diabetes is diabetes Type I, diabetes Type II, or gestational diabetes.
3. Metformin for use according to item 1,
    wherein the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, and hypertension.
4. Metformin for use according to item 1,
    wherein the patient is at risk of developing or suffers from a disease or disorder selected from the group consisting of cancer, cognitive decline, dementia, frailty, falls, unsteadiness, erectile dysfunction, sexual dysfunction, chronic pain, foot ulceration, retinal disease, decreased vision, renal disease or reduced longevity.
5. Metformin for use according to any of items 1 to 4, wherein the level of GDF15 is increased by at least 25%.

6. Metformin for use according to any of items 1 to 5, wherein the level of GDF15 is increased in comparison to a reference.
7. Metformin for use according to item 6 wherein the reference is
   (i) the GDF15 level in the patient before metformin administration, in particular in a reference sample of the patient taken at a time point prior to Metformin administration, or
   (ii) a representative reference value.
8. A method of identifying a patient who will benefit from metformin treatment, comprising the steps of
   (i) administering an effective amount of metformin to a patient,
   (ii) determining the level of GDF15 in a patient's sample, and
   (iii) comparing the GDF15 level determined in step (ii) to that of a reference, wherein an increased level of GDF15 is indicative of a response of the patient to metformin administration.
9. The method of item 8, wherein the level of GDF15 is increased by at least 25%.
10. The method of item 8 or 9, wherein the reference is representative of GDF15 level before metformin administration, in particular in a reference sample of the patient taken at a time point before Metformin administration or a representative reference value.
11. The method of any of items 8 to 10, wherein the level of GDF15 in a patients sample is determined within hours after metformin administration; in particular within 1, 2, 3, 4, 5, 6, 7, 8, 9, 10, 11, or 12 hours after Metformin administration.
12. The method of any of items 8 to 10, wherein the level of GDF15 in a patient's sample is determined within days after metformin administration, in particular within 1, 2, 3, 4, 5, 6, or 7 days after metformin administration.
13. The method of any of items 8 to 12, wherein the patient's sample is selected from the group consisting of bodily fluid and tissue sample, in particular whole blood, serum, plasma, sputum, saliva, and urine.
14. The method of any of items 8 to 13, wherein the level of GDF15 is determined directly or indirectly using a GDF15-binding molecule.
15. The method of item 14, wherein the level of GDF15 is determined using an antibody specific for GDF15, in particular an antibody which competes with an antibody which recognizes a peptide comprising amino acids 197-308 of GDF-15.
16. The method of any of items 8 to 15, wherein one or more additional factors are determined, wherein the one or more factors are selected from the list consisting of
   (a) HbA1c
   (b) Fasting glucose levels
   (c) Post-prandial glucose levels
   (d) Random glucose levels
   (e) Fructosamine levels
   (f) Fasting insulin levels
   (g) Hemeostatic model assessment of insulin resistance (HOMAIR)
   (h) Other measures of insulin resistance
   (i) Glycated albumin
   (j) Lipid levels (HDL, LDL, total cholesterol, triglycerides, apolipoprotein B),
   (k) Albuminuria (microalbuminuria or macroalbuminuria)
   (l) Creatinine or estimated GFR,
   (m) ALT level
   (n) Vitamin $B_{12}$ level
   (o) Cotinine level
   (p) Telomere length
   (q) one or more of the biomarker selected from the group consisting of NT-proBNP, Trefoil Factor 3, Apolipoprotein B, Angiopoietin-2, Osteoprotegerin, Alpha-2-Macroglobulin, Hepatocyte Growth Factor Receptor, Glutathione S Transferase alpha, Chromogranin A, IGF Binding Protein 4, Tenascin-C, Selenoprotein P, Macrophage Derived Chemokine, YKL-40, IGF Binding Protein 2
   (r) one or more of the factors selected from the group consisting of Blood pressure, Weight, BMI, waist to hip ratio, Waist circumference, Diabetes duration, Smoking status, Imaging evidence of fatty liver, Troponin levels, LV dysfunction, Cardiovascular risk, other diabetes complications, retinal imaging, and nerve conduction studies.
17. Pharmaceutical composition comprising metformin and at least one pharmaceutically acceptable carrier, adjuvant and/or excipient for use in treating diabetes, in particular diabetes I or II, in a patient, wherein the patient exhibits an increased level of GDF15 in response to metformin treatment.
18. A method of adapting the dosage of Metformin comprising
   (i) administering metformin to a patient,
   (ii) determining the level of GDF15 in a patient's sample
   (iv) comparing the GDF15 level determined in step (ii) to a reference, and
   (v) adjusting the dosage of metformin in that the treatment with Metformin is stopped in case the level of GDF15 is not increased, and the dosage of Metformin is maintained or increased in case the level of GDF15 is increased.
19. The method of item 18, wherein in step (i) metformin is administered in an amount of 500-2000 mg, in particular in an amount of 500, 550, 600, 650, 700, 750, 800, 850, 900, 950, 1000, 1100, 1200, 1300, 1400, 1500, 1600, 1700, 1800, 1900, or 2000 mg.
20. The method of item 18 or 19, wherein in step (iii) the dosage of metformin is increased by 10, 20, 30, 40, 50, 60, 70, 80, 90, 100, 150, or 200% in case the level of GDF15 is increased, in particular in response to the initial metformin administration.
21. Use of GDF15 as biomarker for identifying a patient who will benefit from metformin treatment.
22. A kit for use in identifying a patient who will benefit from metformin treatment, comprising means for detecting the expression level of GDF15.
23. The kit for use in identifying a patient who will benefit from Metformin treatment according to item 22, wherein the kit further comprises
   (a) a container,
   (b) suitable control, and/or
   (c) a data carrier, wherein the data carrier comprises information such as
      (i) instructions concerning methods identifying a patient who has a high likelihood of responding to Metformin treatment
      (ii) instructions for use of the means for detecting GDF15 level,
      (iii) quality information such as information about the lot/batch number of the means for detecting GDF15 level and/or of the kit, the manufacturing or assembly site or the expiry or sell-by date, information concerning the correct storage or handling of the kit, (iv) information concerning the composition of the buffer(s), diluent(s), reagent(s) for detecting level of GDF15, (v) information concerning the interpretation of information obtained when performing the above-mentioned methods of identifying a patient who has a high likelihood of responding to Metformin treatment, (vi) a warning concerning possible misinterpretations or wrong results when applying unsuitable methods and/or unsuitable means, and/or (vii) a warning concerning possible misinterpretations or wrong results when using unsuitable reagent(s) and/or buffer(s).

24. Use of the kit of item 22 or 23 in a method according to any of items 8 to 16.

25. Method of treating a patient at risk of developing or suffering from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease and reduced longevity comprising the step of administering to said patient a therapeutically effective amount of metformin, wherein said patient exhibits an increased level of GDF15 in response to (an initial) metformin treatment.

26. Method of treating a patient at risk of developing or suffering from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, and hypertension.

27. Method of treating a patient at risk of developing or suffering from a disease or disorder selected from the group consisting of cancer, cognitive decline, dementia, frailty, falls, unsteadiness, erectile dysfunction, sexual dysfunction, chronic pain, foot ulceration, retinal disease, decreased vision, renal disease and reduced longevity, comprising the step of administering to said patient a therapeutically effective amount of metformin, wherein said patient exhibits an increased level of GDF15 in response to (an initial) metformin treatment.

28. The method of any of items 25 to 27, wherein the level of GDF15 is increased by at least 25%.

29. The method of any of items 25 to 28, wherein the level of GDF-15 is measured in a sample of the patient, in particular wherein the level of GDF-15 is measured in a sample of the patient prior to treatment.

30. The method of any of items 25 to 29, wherein the level of GDF-15 is measured in a sample of the patient and is compared to a reference.

31. The method of item 30, wherein the reference is representative of GDF15 level before metformin administration, in particular in a reference sample of the patient taken at a time point before metformin administration or a representative reference value.

32. The method of any of items 25 to 31, wherein the level of GDF15 is determined in in a patient's sample within hours after an initial metformin administration; in particular within 1, 2, 3, 4, 5, 6, 7, 8, 9, 10, 11, or 12 hours after an initial metformin administration.

33. The method of any of items 25 to 32, wherein the level of GDF15 is determined in in a patient's sample within days after an initial metformin administration, in particular within 1, 2, 3, 4, 5, 6, or 7 days after an initial metformin administration.

34. The method of any of items 25 to 33, wherein the level of GDF-15 is determined in a patient's sample, in particular in a patient's sample selected from the group consisting of bodily fluid and tissue sample, in particular whole blood, serum, plasma, sputum, saliva, and urine.

35. The method of any of items 23 to 30, wherein the level of GDF15 is determined in a patient's sample directly or indirectly using a GDF15-binding molecule.

36. The method of item 35, wherein the level of GDF15 is determined using an antibody specific for GDF15, in particular an antibody which competes with an antibody which recognizes a peptide comprising amino acids 197-308 of GDF-15.

37. The method of any of items 25 to 36, wherein one or more factors are determined, wherein the one or more factors are selected from the list consisting of (a) HbA1c
(b) Fasting glucose levels
(c) Post-prandial glucose levels
(d) Random glucose levels
(e) Fructosamine levels
(f) Fasting insulin levels
(g) Hemeostatic model assessment of insulin resistance (HOMAIR)
(h) Other measures of insulin resistance
(i) Glycated albumin
(j) Lipid levels (HDL, LDL, total cholesterol, triglycerides, apolipoprotein B),
(k) Albuminuria (microalbuminuria or macroalbuminuria)
(l) Creatinine or estimated GFR,
(m) ALT level
(n) Vitamin $B_{12}$ level
(o) Cotinine level
(p) Telomere length
(q) one or more of the biomarker selected from the group consisting of NT-proBNP, Trefoil Factor 3, Apolipoprotein B, Angiopoietin-2, Osteoprotegerin, Alpha-2-Macroglobulin, Hepatocyte Growth Factor Receptor, Glutathione S Transferase alpha, Chromogranin A, IGF Binding Protein 4, Tenascin-C, Selenoprotein P, Macrophage Derived Chemokine, YKL-40, IGF Binding Protein 2, and
(r) one or more of the factors selected from the group consisting of Blood pressure, Weight, BMI, waist to hip ratio, Waist circumference, Diabetes duration, Smoking status, Imaging evidence of fatty liver, Troponin levels, LV dysfunction, Cardiovascular 38. Method of treating a group of patients who will benefit from metformin treatment, comprising the steps of
   (i) administering an effective amount of metformin to a patient,
   (ii) determining the level of GDF15 in a patient's sample, and
   (iii) comparing the GDF15 level determined in step (ii) to that of a reference,
   (iv) continuing administration of metformin to those patients exhibiting an increased level of GDF15.
39. Method of treating a group of patients who will not benefit from metformin treatment, comprising the steps of
   (i) administering an effective amount of metformin to a patient,
   (ii) determining the level of GDF15 in a patient's sample, and
   (iii) comparing the GDF15 level determined in step (ii) to that of a reference,
   (iv) discontinuing administration of metformin to those patients exhibiting a decreased level of GDF15,
   and optionally
   (i) administering an alternative treatment to those patients exhibiting a decreased level of GDF15.
40. The method of item 39, wherein the alternative treatment in optional step (v) is selected from the group consisting of sulfonylureas, dopamine agonist, DPP-4 inhibitors, glucagon-like peptides, meglitinides, amylinomimetic, alpha-glucosidase inhibitors, SGLT2 inhibitors, and thiazolidinediones.
41. Method of identifying a patient who will not benefit from metformin treatment, comprising the steps of
   (i) administering an effective amount of metformin to a patient,
   (ii) determining the level of GDF15 in a patient's sample, and
   (iii) comparing the GDF15 level determined in step (ii) to that of a reference, wherein an unaltered or decreased level of GDF15 is indicative of a patient not responding to metformin administration.
42. Sulfonylureas, dopamine agonist, DPP-4 inhibitors, glucagon-like peptides, meglitinides, amylinomimetic, alpha-glucosidase inhibitors, SGLT2 inhibitors, and/or thiazolidinediones for use in treating a patient, wherein the patient exhibits an unaltered or decreased level of GDF15 in response to metformin treatment, and wherein the patient is at risk of developing or suffers from a disease or disorder selected from the group consisting of prediabetes, diabetes, hypoglycemia in the setting of diabetes, polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease or reduced longevity.
43. Method of shortening the time for determining whether a patient responds to metformin administration, comprising the steps of
   (i) administering an effective amount of metformin to a patient,
   (ii) determining the level of GDF15 in a patient's sample, and
   (iii) comparing the GDF15 level determined in step (ii) to that of a reference,
   wherein an increased level of GDF15 is indicative of a patient responding to metformin administration, and wherein an unaltered or decreased level of GDF15 is indicative of a patient not responding to metformin administration.
44. The method of item 43, wherein the time for determining whether a patient responds to metformin administration is below 4 weeks.
45. Method of preventing, delaying, and/or treating diabetes associated complications in a patient, comprising the steps of
   (i) administering an effective amount of metformin to a patient,
   (ii) determining the level of GDF15 in a patient's sample, and
   (iii) comparing the GDF15 level determined in step (ii) to that of a reference,
   (iv) continuing metformin administration to those patients exhibiting an increased level of GDF15, and discontinuing administration of metformin to those patients exhibiting an unaltered or decreased level of GDF15,
   and optionally
   (v) administering an alternative treatment to those patients exhibiting an unaltered or decreased level of GDF15.
46. Method of preventing, delaying, and/or treating diabetes associated complications in a patient, comprising the steps of
   (i) administering an effective amount of metformin to a patient,
   (ii) determining the level of GDF15 in a patient's sample, and
   (iii) comparing the GDF15 level determined in step (ii) to that of a reference, wherein an increased level of GDF15 is indicative of the patient responding to metformin treatment, and an unaltered or decreased level of GDF15, is indicative of the patient not responding to metformin treatment,
   and optionally
   (iv) considering an alternative treatment for those patients exhibiting an unaltered or decreased level of GDF15 in order to reduce diabetes associated complications in said patient.
47. Method of item 45 or 46, wherein the diabetes associated complications are selected from the list consisting of polycystic ovary syndrome, hirsutism, amenorrhea, non-alcoholic fatty liver disease, non-alcoholic steatohepatitis, infertility, obesity, Vitamin $B_{12}$ deficiency, insulin resistance, and other risk factors for ischemic heart disease or myocardial infarction such as but not limited to angina, dyslipidemia, hypertension, cancer, cognitive decline, dementia, frailty, falls, unsteadiness, erectile dysfunction, sexual dysfunction, chronic pain, foot ulceration, retinal disease, decreased vision, renal disease and reduced longevity.
48. Method of any of items 45-47, wherein the alternative treatment is selected from the group consisting of sulfonylureas, dopamine agonist, DPP-4 inhibitors, glucagon-like peptides, meglitinides, amylinomimetic, alpha-glucosidase inhibitors, SGLT2 inhibitors, and thiazolidinediones.

The invention is described in more detail in the examples and figures that are not to be understood as limiting the scope of present invention.

EXAMPLES 12,537 people with either diabetes, impaired glucose tolerance or impaired fasting glucose who had additional CV risk factors[11,12] were recruited. After being randomly allocated to basal glargine insulin—mediated normoglycemia or standard care, and to omega 3 fatty acid supplements or placebo using a factorial design, they were followed for a median of 6.2 years for cardiovascular events and other health outcomes. Prior to randomization 8,494 (68%) participants provided a baseline blood sample that was spun, separated, aliquotted, frozen (within 2 hours of collection) and transported to the Population Health Research Institute (PHRI) biobank in Hamilton, Canada where it was stored in nitrogen vapor-cooled tanks at −160° Celsius. A subset of these participants (5,078) provided additional consent for the storage and analysis of genetic material from buffy coat samples.

After the trial was completed, a 1 ml serum aliquot was transported to Myriad RBM (Austin, Tex., USA) for the multiplex analysis of 284 biomarkers that prior research had suggested were related to cardiovascular disease or diabetes. At Myriad RBM Inc., the samples were thawed at room temperature (RT), vortexed, spun at 13,000 g for 5 minutes for clarification, and an aliquot was removed into a master microtiter plate for analysis. Using automated pipetting, an aliquot of each sample was introduced into one of the capture microsphere multiplexes of the Human Discovery-MAP. The mixtures of sample and capture microspheres were thoroughly mixed and incubated at RT for 1 hour. Multiplexed cocktails of biotinylated reporter antibodies for each multiplex (such as GDF-15), were then added robotically, and after thorough mixing, were incubated for an additional hour at RT. Multiplexes were developed using an excess of streptavidinphycoerythrin solution which was thoroughly mixed into each multiplex and incubated for 1 hour at RT. The volume of each multiplexed reaction was reduced by vacuum filtration and then increased by dilution into matrix buffer for analysis. Analysis was performed in Luminex 100 and 200 instruments and the resulting data stream was interpreted using proprietary data analysis software developed at RBM. For each multiplex, both calibrators and controls were included on each microtiter plate. Eight-point calibrators were run in the first and last column of each plate and 3-level quality controls were included in duplicate. Testing results were determined first for the high, medium and low controls for each multiplex to ensure proper assay performance. Unknown values for each of the analytes localized in a specific multiplex were determined using 4 and 5 parameter, weighted and non-weighted curve fitting algorithms included in the data analysis package[40]. Only an identification number (i.e. no other information) was provided with the samples. As previously reported, after masked review of the reported results, 237 biomarkers from 8,401 participants were deemed suitable for further analysis[13]. A subset of 4390 of these individuals who consented to genetic analyses were also genotyped as described below.

Example 1: Identifying Biomarkers Related to Metformin Use

The 237 available biomarkers were analyzed to identify those that were statistically independent determinants of the use of metformin using unadjusted logistic regression models and forward selection. Of the 31 significant biomarkers identified using this approach, 1 biomarker (growth differentiation factor 15-GDF15) had an effect size that was more than 3-fold greater than any of the others. All remaining analyses therefore focused on this 1 biomarker as described in detail below.

A total of 2317/8401 (27.6%) participants with measured biomarkers were taking metformin. As noted in Table 1, compared to people not taking metformin, those on metformin were more likely to: a) be women, younger, and heavier; b) have diabetes, hypertension, and albuminuria; c) have better renal function; and d) be on ACE inhibitors or angiotensin receptor blockers. They were less likely to have had a prior cardiovascular event or be on beta blockers or antiplatelet agents.

TABLE 1

Characteristics of Biomarker Study Participants Taking Metformin

|  | All | Baseline Metformin | No Metformin | P |
|---|---|---|---|---|
| N | 8401 | 2317 | 6084 |  |
| Male | 5553 (66.1) | 1431 (61.8) | 4122 (67.8) | <0.001 |
| Mean Age (years) | 63.7 (7.9) | 62.6 (7.6) | 64.1 (8.0) | <0.001 |
| Region |  |  |  | <0.001 |
| N. America or Australia | 1425 (17.0) | 479 (20.7) | 946 (15.5) |  |
| S. America | 2772 (33.0) | 734 (31.7) | 2038 (33.5) |  |
| Europe | 3822 (45.5) | 998 (43.1) | 2824 (46.4) |  |
| India | 382 (4.5) | 106 (4.6) | 276 (4.5) |  |
| Current Smoking | 1050 (12.5) | 267 (11.5) | 783 (12.9) | 0.1 |
| Prior diabetes | 6840 (81.4) | 2298 (99.2) | 4542 (74.7) | <0.001 |
| Diabetes Duration | 5.3 (5.8) | 5.7 (5.5) | 5.1 (5.9) | <0.001 |
| Hypertension | 6638 (79.0) | 1927 (83.2) | 4711 (77.4) | <0.001 |
| Prior Cardiovascular Event | 4991 (59.4) | 1227 (53.0) | 3764 (61.9) | <0.001 |
| Mean BMI | 30.1 (5.3) | 31.1 (5.6) | 29.7 (5.1) | <0.001 |
| Mean eGFR (ml/min/1.73 m2) | 77.5 (21.9) | 79.8 (21.6) | 76.6 (22.0) | <0.001 |
| Mean HbA1c (%) | 6.5 (0.9) | 6.6 (0.9) | 6.5 (1.0) | <0.001 |
| Mean FPG (mmol/L) | 7.3 (2.0) | 7.4 (2.0) | 7.3 (2.0) | 0.007 |
| Reported/Measured Albuminuria | 2656 (31.6) | 837 (36.1) | 1819 (29.9) | <0.001 |
| Baseline CV Medications |  |  |  |  |
| Statins | 4616 (55.0) | 1234 (53.3) | 3382 (55.6) | 0.054 |
| ACE-I or ARB | 5793 (69.0) | 1696 (73.2) | 4097 (67.4) | <0.001 |
| Beta blockers | 4526 (53.9) | 1132 (48.9) | 3394 (55.8) | <0.001 |
| Antiplatelet Drugs | 1120 (13.3) | 260 (11.2) | 860 (14.1) | <0.001 |
| Outcomes During Follow-up |  |  |  |  |
| Composite CV Outcome | 1405 (16.7) | 346 (14.9) | 1059 (17.4) | 0.007 |
| Expanded Composite CV Outcome | 2435 (29.0) | 622 (26.8) | 1813 (29.8) | 0.008 |
| Death | 1340 (16.0) | 331 (14.3) | 1009 (16.6) | 0.01 |

After adjusting for factors associated with the propensity to prescribe metformin including age, sex, weight, prior cardiovascular event, a prior diagnosis of diabetes, serum creatinine, HbA1c, and the fasting plasma glucose, the forward selection approach identified 26 biomarkers that were independently associated with metformin use (i.e. the p value for each biomarker was <0.00021). With the exception of GDF15, the odds of metformin use for every 1 standard deviation increase in the level of these biomarkers ranged from 0.71 to 1.24 (Table 2).

TABLE 2

Independent Biomarker Determinants of Metformin Use at Baseline*

| Biomarker | Odds Ratio | Lower CI | Upper CI | P Value |
|---|---|---|---|---|
| Growth Differentiation Factor 15 | 3.75 | 3.418 | 4.114 | <0.00E−15 |
| Epithelial-Derived Neutrophil-Activating Protein 78 | 1.242 | 1.16 | 1.331 | 6.40E−10 |
| Vascular Endothelial Growth Factor Receptor 2 | 1.215 | 1.133 | 1.303 | 4.48E−08 |
| Galectin-3 | 1.201 | 1.117 | 1.29 | 6.51E−07 |
| Apolipoprotein A-IV | 1.2 | 1.124 | 1.281 | 5.01E−08 |
| CD163 | 1.177 | 1.097 | 1.263 | 5.41E−06 |
| Glucagon-like Peptide 1, total | 1.169 | 1.113 | 1.228 | 5.20E−10 |
| Peptide YY | 1.147 | 1.092 | 1.205 | 4.68E−08 |
| Alpha-2-Macroglobulin | 0.886 | 0.819 | 0.958 | 2.27E−03 |
| Insulin | 0.881 | 0.81 | 0.958 | 2.95E−03 |
| Visceral adipose tissue-derived serpin A12 | 0.881 | 0.827 | 0.94 | 1.12E−04 |
| Myoglobin | 0.87 | 0.809 | 0.935 | 1.55E−04 |
| Alpha-1-Antitrypsin | 0.86 | 0.803 | 0.921 | 1.49E−05 |
| Apolipoprotein D | 0.852 | 0.795 | 0.912 | 4.24E−06 |
| Prostasin | 0.846 | 0.786 | 0.911 | 9.44E−06 |
| Collagen IV | 0.845 | 0.791 | 0.904 | 9.65E−07 |
| Tissue type Plasminogen activator | 0.842 | 0.784 | 0.905 | 2.41E−06 |
| Neuronal Cell Adhesion Molecule | 0.836 | 0.776 | 0.901 | 2.63E−06 |
| Urokinase-type Plasminogen Activator | 0.826 | 0.771 | 0.885 | 6.79E−08 |
| Angiopoietin-2 | 0.811 | 0.755 | 0.87 | 5.95E−09 |
| Tenascin-C | 0.791 | 0.74 | 0.846 | 7.67E−12 |
| Proinsulin, Intact | 0.776 | 0.734 | 0.82 | 0.00E+00 |
| Fas Ligand | 0.764 | 0.684 | 0.855 | 2.31E−06 |
| Ferritin | 0.759 | 0.711 | 0.811 | 1.11E−16 |
| Osteocalcin | 0.752 | 0.7 | 0.808 | 8.88E−15 |
| Tumor necrosis factor receptor 2 | 0.713 | 0.655 | 0.776 | 5.00E−15 |

Conversely, as noted in FIG. 1A, the odds of metformin use for every 1 unit increase in GDF15 level varied from 3.73 (95% CI 3.40, 3.49) to 3.94 (95% CI 3.59, 4.33) depending on the specific clinical variables that were included. To determine the degree to which the other 236 biomarkers affected the observed association between GDF15 and metformin use, logistic regression models that only included GDF15 (i.e. none of the other biomarkers) and the clinical variables were examined. These models consistently showed a smaller odds ratio of approximately 2.6 (FIG. 1 B).

The mean concentration of GDF15 rose with progressively higher doses of metformin (FIG. 2). After accounting for age, sex, weight, a prior cardiovascular event, prior diabetes, creatinine, HbA1c and FPG, every 1 standard deviation higher natural logarithm-transformed GDF15 level (equivalent to a back-transformed increment of 1.52 ng/ml) predicted about a 282 mg higher metformin dose ($P<0.0001$).

This analysis of 237 biomarkers in the serum of people with either impaired glucose tolerance, impaired fasting glucose or early diabetes has clearly identified GDF15 as an important novel biomarker for the use and dose of metformin. Metformin use was also independently (but much less strongly) linked to higher or lower levels of 25 other measured biomarkers (Table 2). The remaining biomarkers were not statistically linked to metformin either because: a) they were truly not linked to metformin; or b) their link to metformin was statistically explained by a link to either GDF15 or 1 or more of the other 25 biomarkers that were linked to metformin. These possibilities were explored by assessing the genetic and biomarker determinants of GDF15. The absence of any relationship between the genetic polymorphism linked to GDF15 levels and other biomarkers suggests that metformin's effect on any of the other biomarkers is unlikely to be mediated through its effect on GDF15.

Metformin is an effective glucose lowering drug and these data clearly show that the GDF15 level is a strong indicator of the use and dose of metformin. These analyses also show that metformin's effect on GDF15 levels is likely to be independent of its effect on glucose levels for several reasons. First, as noted above and in FIG. 1 and Table 2, the observed strong relationship between GDF15 levels and both the use and dose of metformin is independent of the relationship between metformin and markers of glucose metabolism including HbA1c levels, fasting glucose level, insulin levels and proinsulin levels. Second, insulin itself had no effect on hepatocyte secretion of GDF15. Third, the genetic variant linked to higher GDF15 levels is not statistically linked to any other biomarker associated with glucose physiology.

Example 2: Metformin's Effect on GDF15 Production and Secretion in Mouse Hepatocyte Studies To further understand the link between metformin and GDF15 levels, in vitro experiments were conducted using mouse hepatocytes. Primary hepatocytes from 4 different C57Bl6 wild-type male mice were isolated by collagenase digestion as previously described[14]. Briefly, cells were plated on 12-well collagen-coated plates overnight in William's Media E containing 10% fetal bovine serum (FBS) and 1% antibiotic-antimycotic. The next morning, cells were washed with phosphate buffer saline, and media was replaced with fresh William's Media E containing 0.1% FBS and either no drug, metformin (concentrations ranging from 250-1000 μM), direct AMPK activator A769662 (10 μM; LC Laboratories, Woburn, Mass.), insulin (10 nM; Life Technologies) or hydrogen peroxide (0.5 mM, EMD Millipore) for 24 hours. Media was then snap frozen and stored at −80° C. for later analyses, and cells were harvested in cell lysis buffer for assessment of total protein or RNA.

GDF15 release into the media was measured using a commercially available ELISA kit (R&D Systems, Minneapolis, Minn.) and expressed per mg of hepatocyte protein. Total RNA was isolated using the Trizol plus RNA Purification kit (Ambion), concentrated with Speedvac (Thermo), and then quantified using Quant-IT RiboGreen (LifeTech). Total RNA was then reverse transcribed and amplified using the Illumina TotalPrep RNA Amplification Kit (LifeTech) according to the manufacturer's protocol. Samples were hybridized to the Illumina Mouse Ref-8 v2.0 complementary DNA BeadChip and scanned on the iScan System (Illumina). The raw sample probe profile and control probe profile were exported from GenomeStudio version 1.9.0 (Illumina). The expression values were adjusted for background effect using the negative control probes[15] and normalized using quantile-normalization and ln transformed[16]. A total of 12381 RNA transcript probes that had a detection P-value <0.05 in >50% of the samples were analyzed.

As the liver is the primary organ in which metformin accumulates[18], its effects were tested in isolated mouse hepatocytes. Metformin (0.5 mM) but not vehicle increased GDF15 protein in the hepatocyte media (FIG. 3, Panel A). Moreover, the increased GDF15 protein secretion was accompanied by a 1.6 fold increase in GDF15 mRNA (FIG. 3, Panel B; P=0.003). Notably, GDF15 secretion was unaffected by either the direct AMPK activator A769662[19,20], or factors shown to alter GDF15 expression in other cell lines including insulin[21] and hydrogen peroxide[22] (FIG. 4A).

The fact that the metformin-GDF15 relationship is only slightly attenuated after adjustment for glucose and HbA1c levels illustrates that GDF15 reflects a non-glycemic effect of metformin.

Example 3: Metformin's Effect on GDF15 Production and Secretion in Mouse in In Vivo Studies Next the effects of metformin on serum GDF15 were investigated in vivo by treating mice both acutely and chronically with metformin. For the acute experiments, 12 (i.e. 6 per group) 20-week old male C57bl6 mice (Jackson Laboratories) were fasted for 12 hours then allowed to feed ad libitum for 2 hours prior to injection with either metformin (250 mg/kg in 10 μl/g body weight saline) or vehicle (10 μl/g body weight saline) intraperitoneally. Blood was collected 90 minutes later by tail vein bleed, and serum was assayed for GDF15 levels using the Elisa described above (R&D Systems, Minneapolis, Minn.). The durability of this effect was then assessed in chronic treatment experiments by measuring serum GDF15 levels in 8-week old obese, male C57bl6 mice fed a high-fat diet (HFD; 60% kcal from fat) for 6 weeks[17]. Eight such mice (i.e. 4 per group) then had either metformin (2.5 g/kg diet) or no drug added to the HFD for an additional 6 weeks. Fed bloods were sampled by tail vein bleed from the animals at the end of the treatment period and serum GDF15 measured as above. Animal experiments were all approved by the McMaster University Animal Ethics Committee.

Compared to an injection of saline, metformin (250 mg/kg) significantly increased (P<0.05) the 90 minute serum levels of GDF 15 (FIG. 5, Panel A). The durability of this response was assessed in obese, insulin-resistant mice treated with a high-fat diet supplemented with metformin (delivered as 2.5 g/kg metformin in a 60% high-fat diet—a dose which elicits clinically relevant concentrations of serum metformin and improves glucose homeostasis)[17,18] for 6 weeks. As noted in FIG. 5 (Panel B), metformin significantly increased serum GDF 15 levels compared to untreated controls (P<0.05).

Example 4: Genotyping of Participants

Samples were genotyped on Illumina's HumanCore Exome chip. Standard quality control measures were assessed. SNPs were excluded on the basis of low call rates (<99%), deviation from Hardy-Weinberg ($p<10^{-7}$), and low minor allele frequency (MAF<0.01). Samples with low call rates (<99%), cryptic relatedness and non-concordance between their genetic and reported sex or ethnicity were also removed. After quality control, the sample consisted of 4,390 participants and 284,024 SNPs. A GWAS was completed for each biomarker in ORIGIN using the 284,024 typed SNPs. Linear regression of each SNP with each biomarker was performed using the PLINK software (version 1.07), with biomarker concentration as the dependent variable. The regression models were first computed in each ethnic group separately (African, European/Caucasian and Latin American), adjusting for age, sex, and principal components 1-5. The results were then meta-analyzed across these groups to ensure a relatively consistent trend across ethnic groups, reduce the number of false positives, and minimize the risk of confounding caused by population stratification.

Two approaches were used to explore the link between GDF15 and other biomarkers that may change in concert with GDF15. First, a genetic polymorphism within the intron of the GDF15 gene was shown to be linked to higher GDF15 levels (rs1227731; 0.378 increase in concentration per allele, P=4.01e-40). Second, the relationship between this polymorphism and each of 236 biomarker levels was assessed using 236 linear regression models in the 4390 participants who consented to genetic analyses. None of the other biomarkers were linked to this polymorphism at a P value below 0.00021 before or after adjustment for metformin use.

Example 5: Statistical Analyses

Statistical analyses were conducted using SAS Version 9.2 for UNIX (SAS Institute Inc., Cary, N.C.) or R (Version 3.0.1), and analyses of data were based on natural logarithm-transformed GDF15 levels. Regression models were used to analyze the human data and Student's t tests or Tukey's test were used to analyze the hepatocyte and mouse study data.

The GDF15 biomarker was identified by scrutinizing the results of five different regression models that forced in age, sex, and clinical characteristics known to be linked to the propensity of physicians to prescribe metformin (i.e. weight, prior cardiovascular disease, prior diabetes, creatinine, HbA1c and fasting plasma glucose). These models used a forward selection approach to identify independent biomarker determinants of metformin use from all 237 biomarkers based on a Bonferroni-corrected P-value for significance of 237/0.05 (i.e. 0.00021). After GDF15 was identified as a very strong determinant of metformin use, these multivariable regression analyses were then rerun to determine whether inclusion of those biomarkers attenuated or amplified the relationship between GDF15 and metformin use. The mean concentration of GDF15 in people taking different doses of metformin was then calculated, and the relationship between metformin dose and the GDF15 level was estimated using linear regression after accounting for the independent variables noted above. Finally, a similar forward selection approach was used to identify biomarkers independently linked to GDF15.

The invention claimed is:

1. A method for identifying a patient suffering from diabetes who will benefit from metformin treatment, said method comprising:
   (a) administering metformin to a patient having diabetes;
   (b) obtaining a sample from the patient;
   (c) determining the level of GDF15 or a functional variant thereof in the sample; and
   (d) comparing the level of GDF15 or functional variant thereof after the administration in step (a) to the level of GDF15 or functional variant in the patient before the administration or to a reference value, wherein an increased level of GDF15 or functional variant thereof after the administration in step (a) indicates that the patient responds to the metformin administration,
   wherein the functional variant of GDF15 comprises a sequence having at least 80% sequence identity to SEQ ID NO: 1.

2. The method of claim 1, wherein the diabetes is diabetes I or II.

3. The method of claim 1, wherein metformin is administered in step (a) in an amount of 500-2000 mg, wherein the amount administered is sufficient to induce a response in a patient responding to metformin treatment.

4. The method of claim 1, wherein metformin is administered in step (a) in an amount of 500, 550, 600, 650, 700, 750, 800, 850, 900, 950, 1000, 1100, 1200, 1300, 1400, 1500, 1600, 1700, 1800, 1900, or 2000 mg, wherein the amount administered is sufficient to induce a response in a patient responding to metformin treatment.

5. The method of claim 1, wherein the level of GDF15 increases after the administration in step (a) by a level of at least 25%, at least 50%, at least 75%, or at least 100% as compared to the level of GDF15 in the patient prior to administration or as compared to a reference value.

6. The method of claim 1, wherein the GDF15 comprises an amino acid sequence comprising SEQ ID NO:1.

7. The method of claim 1, wherein determining the level of GDF15 or a functional variant thereof comprises ELISA, Western Blot, immunoprecipitation, HPLC, microarrays, mass spectroscopy, sequencing, or immune-detection assay.

8. The method of claim 1, wherein determining the level of GDF15 or a functional variant thereof comprises using a monoclonal antibody specific for GDF15.

9. The method of claim 8, wherein the GDF15 comprises an amino acid sequence comprising SEQ ID NO:1.

10. The method of claim 1, wherein determining the level of GDF15 or a functional variant thereof occurs within hours or days after the metformin administration of step (a).

11. The method of claim 1, wherein the reference value is a reference value that is representative of the level of GDF15 or functional variant thereof in a subject who has not obtained metformin administration.

12. The method of claim 1, wherein the metformin is administered in a composition comprising metformin and at least one pharmaceutically acceptable carrier, adjuvant, and excipient.

* * * * *